US006994966B2

(12) United States Patent
Dukler et al.

(10) Patent No.: US 6,994,966 B2
(45) Date of Patent: Feb. 7, 2006

(54) COMBINATORIAL COMPLEX CARBOHYDRATE LIBRARIES AND METHODS FOR THE MANUFACTURE AND USES THEREOF

(75) Inventors: Avinoam Dukler, Modi'in (IL); Nir Dotan, Shoham (IL)

(73) Assignee: Glycominds Ltd., Lod (IL)

( * ) Notice: Subject to any disclaimer, the term of this patent is extended or adjusted under 35 U.S.C. 154(b) by 0 days.

(21) Appl. No.: 09/860,559

(22) Filed: May 21, 2001

(65) Prior Publication Data

US 2002/0094541 A1 Jul. 18, 2002

Related U.S. Application Data

(60) Division of application No. 09/783,083, filed on Feb. 15, 2001, which is a continuation-in-part of application No. PCT/IL00/00099, filed on Feb. 17, 2000.

(51) Int. Cl.
*G12Q 1/68* (2006.01)

(52) U.S. Cl. .................. 435/6; 536/1.11; 536/123.1
(58) Field of Classification Search .................. 435/6, 435/41, 72, DIG. 38, 45, 46, 49, DIG. 46, 435/DIG. 45, DIG. 49, DIG. 7; 536/1.11, 536/123.1
See application file for complete search history.

(56) References Cited

U.S. PATENT DOCUMENTS

| | | | |
|---|---|---|---|
| 4,833,071 A | | 5/1989 | Wang et al. |
| 5,180,674 A | | 1/1993 | Roth |
| 5,288,637 A | | 2/1994 | Feygenson et al. |
| 5,424,186 A | * | 6/1995 | Fodor et al. .................. 435/6 |
| 5,565,324 A | | 10/1996 | Still et al. |
| 5,700,916 A | | 12/1997 | Kahne et al. |
| 5,770,358 A | * | 6/1998 | Dower et al. .................. 435/6 |
| 5,780,603 A | | 7/1998 | Hindsgaul |
| 5,919,626 A | | 7/1999 | Shi et al. |
| 5,965,719 A | | 10/1999 | Hindsgaul |

FOREIGN PATENT DOCUMENTS

| | | |
|---|---|---|
| WO | WO 97/35202 * | 9/1997 |
| WO | PCT 99/61583 | 2/1999 |
| WO | 99/61583 | 2/1999 |
| WO | WO 02/084249 | 4/2002 |

OTHER PUBLICATIONS

Lubineau, A., & Bonnaffe, D., "Access to molecular diversity in glycosaminoglycans: Combinatorial synthesis of eight chondroitin sulfate disaccharides" Eur. J. Org. Chem. 1999, 10, 2523–2532.*
Anderson, H.; Lamb, M.; Mendelson, R.; Ocana, A. M.; Stephen, A. M.; O'Brien, H. T. "The Carbohydrate Controversy Persists" Carbohydrate News, Issue 1, 1995, 1–7.*
Nicolaou, K. C.; Watanabe, N.; Li, J.; Pastor, J.; Winnssinger, N. "Solid–Phase Synthesis of Oligosaccharides: Construction of a Dodecasaccharide" Angew Chem. Int. Ed. 1998, 37(11), 1559–16561.*
Seitz, O.; Wong, C. H. "Chemoenzymatic Solution– and Solid–Phase Synthesis of O–Glycopeptides of the Mucin Domain of MAdCAM–1. A general Route to O–LacNAc, O–Sialyl–LacNAc, and O–Sialyl–Lewis–X Peptides" J. Am. Chem. Soc., 1997, 119, 8766–8776.*
Seifert, J. and Unverzagt, C. "Synthesis of three Biantennary N–Glycans containing the a–1,6 Core–Fucosyl Motif" Tetrahedron Letters, 1997, 38(45), 7857–7860.*
Sears, P.; Wong, C.–H. 'Strategies for Creating the Diversity of Oligosaccharides' In: Handbook of Combinatorial Chemistry Edited by K. C. Nicolaou et al. Weinheim: Wiley–VCH, 2002, vol. 2, p. 713.*
Nicolaou et al "Solid–Phase Synthesis of Oligosaccharides: Construction of a Dodecasaccharide" Angew. Chem. Int. Ed., 1998, 37(11), 1559–1561.*
Schuster et al "Solid–Phase Chemical–Enzymatic Synthesis of Glycopeptides and Oligosaccharides" J. Am. Chem. Soc., 1994, 116, 1135–1136.*
Liang et al "Parallel Synthesis and Screening of a Solid Phase Carbohydrate Library" Science, 1996, 274, 1520–1522.*
Seitz et al "Chemoenzymatic Solution– and Solid–Phase Synthesis of O–Glycopeptides of the Mucin Domain of MadCAM–1. A general Rout to O–LacNAc, O–Sialyl–LacNAc, and O–Sialyl–Lewis–X Peptides" J. Am. Chem. Soc., 1997, 119, 8766–8776.*
Seifert et al, "Synthesis of three Biantennary N–Glycans containing the (alpha)–1,6 Core–Fucosyl Motif" Tetrahedron Letters, 1997, 38(45), 7857–7860.*
Bierhuizen et al, "Expression of the Developmental 1 Antigen by a Cloned Human cDNA Encoding a Member of a Beta–1,6–N–Acetylglucosaminyltransferase Gene Family", Genes Dev., 7(3):468–478, 1993 (abstract only).
Kahne, D., "Combinatorial Approaches to Carbohydrates", Current Opinion in Chemical Biology, 1: 130–135, (1997) (abstract only).
Liang et al, "Parallel Synthesis and Screening of a Solid Phase Carbohydrate Library", Science, vol. 274, pp 1520–1522, 1996.
Kanie et al, "A Strategy of "Random Glycosylation" for the Production of Oligosaccharide Libraries", Angew, Chem. Int. Engl., No. 23/24, 2720–2722, 1995.

(Continued)

Primary Examiner—Bennett Celsa
Assistant Examiner—Jon D. Epperson

(57) ABSTRACT

The present invention provides methods of utilizing a complex carbohydrate library which includes a plurality of complex carbohydrate structures each being attached to a specific site of a solid support such as a platform for screening and isolating complex carbohydrate structures capable of specifically and uniquely binding with an entity such as a polypeptide.

20 Claims, 15 Drawing Sheets

OTHER PUBLICATIONS

Wang et al, "Combinatorial Carbohydrate Chemistry", *Glycoimmunology* 2, Ed by Axford, Plenum Press, N.Y. 1998, pp 219–236.

Seitz et al, "Chemoenzymatic Solution– and Solid–Phase Synthesis of O–Glycopeptides of the Mucin Domain of MAdCAM–1. A General Route to O–LacNAc, O–Sialyl-LacNAc, and O–Sialyl–Lewis–X Peptides", *J.Am.Chem. Soc.*, 119, pp 8766–8775, 1997.

Seifert et al, Synthesis of Three Biantennary N–Glycans Containing the α–1,6 Core–Fucosyl Motif, *Tetrahydron Letters*, 38(45):7857–7860, 1997.

Köpper, Sabine, "Polymer–Supported Enzymic Synthesis on a Preparative Scale", *Carbohydrate Research*, vol. 265, pp 161–166, 1994.

Koeller et al, "Synthesis of Complex Carbohydrate and Glycoconjugates: Enzyme–Based and Programmable One-Pot Strategies", *Chem. Rev.*, 100, 4465–4493, 2000.

Amados et al "A Family of Human β3–Galactosyltransferases", *J. Biological Chem.*, 273(21), 12770–12778, 1998.

Johnson et al, "Reassessment of the Acceptor Specificity and General Properties of the Lewis Blood–Group Gene Associated α–3/4–fucosyltransferase Purified from Human Milk", *Glycoconjugate J.*, 9:251–264, 1992.

Fukui et al, "Oligosaccharide Microarrays for High–Throughput Detection and Specificity Assignments of Carbohydrate–Protein Interactions", *Nature Biotechnology*, pub. Online www.nature.com/naturebiotechnology Sep. 3, 2002.

Wang et al, "Carbohydrate Microarrays for the Recognition of Cross–Reactive Molecular Markers of Microbes and Host Cells", *Nature Biotechnology*, vol. 20, pp 275–281, 2002.

Houseman et al, "Carbohydrate Arrays for the Evaluation of Protein Binding and Enzymatic Modification", *Chemistry & Biology*, vol. 9, pp443–454, 2002.

Schuster et al, "Solid–Phase Chemical–Enzymatic Synthesis of Glycopeptides and Oligosacchararides", *J. Am. Chem. Soc.*, 116:1135–1136, 1994.

Crout et al, "Glycosidases and Glycosyl Transferases in Glycoside and Oligosaccaride Synthesis", *Current Opinion In Chemical Biology*, 2:98–111, 1998.

Morgan et al, "Unravelling the Biochemical Basis of Blood Group ABO and Lewis Antigenic Specificity", *Glycoconjugate J.*, 17:501–530, 2000.

Dove, Alan, "The Bitterswaeet Promise of Glycobiology", *Nature Biotechnology*, 19(10):913–917, 2001.

Yan, et al, "Polymer–Supported and Chemoenzymatic Synthesis of the *Neisseria Meningitidis* Pentasacharide: A Methodilogical Comparison", *Carbohydrate Research*, 328:3–16, 2000.

* cited by examiner

| | Complex carbohydrate formation |
|---|---|
| ER | S |
| Step 1 | →3)-β GalpNAc-S |
| Step 2 D5 | →3)-β-D Galp-(1→3)-β GalpNAc-S |
| Step 3 H1 | →4)-β GlcpNAc-(1→3)-β-D Galp-(1→3)-β GalpNAc-S |
| Step 4 D7 | →β-D Galp-(1→4)-β D GlcpNAc-(1→3)-β-D Galp-(1→3)-β GalpNAc-S |
| Step 5 H3 | →β-D Galp-(1→4)-β D GlcpNAc-(1→3)-β-D Galp-(1→3)-β GalpNAc-S |
| Step 6 D7 | →3)-β-D Galp-(1→4)-β-D GlcpNAc-(1→3)-β-D Galp-(1→3)-β-D GlcpNAc-(1→3)-β-D Galp-(1→3)-β GalpNAc-S |
| Step 7 D3 | →6)-β-D Galp-(1→4)-β-D GlcpNAc-(1→3)-β-D Galp-(1→3)-β GalpNAc-S<br>-β-D Galp-(1→3)- |
| Step 8 H14 | β-D Galp-(1→3)-β-D Galp-(1→4)-β-D GlcpNAc-(1→3)-β-D Galp-(1→3)-β GalpNAc-S<br>[-β-D-GlcpNAc-(1→6)]<br>-β-D-GlcpNAc-(1→4)- -β-D Galp-(1→4)-<br>[-β-D-GlcpNAc-(1→3)] -β-D GlcpNAc-(1→3)- |
| Step 9 B2 | -β-D-GlcpNAc-(1→6)<br>-β-D-GlcpNAc-(1→4)-β-D-Galp-(1→4)- -β-D Galp-(1→4)-<br>-β-D-GlcpNAc-(1→3) -β D GlcpNAc-(1→3)-β-D Galp-(1→3)-β GalpNAc-S |
| Step 10 D7 | -β-D-GlcpNAc-(1→6)]<br>-β-D Galp-(1→4)- -β D GlcpNAc-(1→3)-β-D Galp-(1→3)-β GalpNAc-S<br>-β-D-GlcpNAc-(1→3)]<br>-α-L Fucp-(1→3)<br>-α-L Fucp-(1→3) |

Fig. 4

—○— No blocking
—◦— BSA blocking
—▽— Acetic Anhydride blocking
—▼— Acetic Anhydride blocking + BSA blocking

COMBINATORIAL COMPLEX CARBOHYDRATE LIBRARIES AND METHODS FOR THE MANUFACTURE AND USES THEREOF This is a divisional application of U.S. patent application Ser. No. 09/783,083, filed Feb. 15, 2001, which is a continuation-in-part of PCT/IL00/00099, filed Feb. 17, 2000, which claims priority from U.S. patent application Ser. No. 09/251,298, filed Feb. 17, 1999, now abandoned.

FIELD AND BACKGROUND OF THE INVENTION

The present invention relates to combinatorial complex carbohydrate libraries and methods for the manufacture and use thereof and, more particularly, to such libraries prepared on a solid support via stepwise enzymatic synthesis, to thereby provide a combinatorial array of complex carbohydrate structures. The combinatorial complex carbohydrate libraries synthesized according to the present invention can be exploited in a variety of ways, including, but not limited to, (i) identification of complex carbohydrate drugs; (ii) identification of complex carbohydrate associated receptors or proteins as potential new carbohydrate related targets for drug therapy; (iii) identification of biologically-active complex carbohydrates; (iv) identification of specific complex structural carbohydrate elements as potential new targets for drug therapy; (v) identification of the active sites of known complex carbohydrate structures; (vi) identification of new glyco-markers in complex carbohydrate structures; and (vii) detection of antibodies formed against a cancer-related glyco-epitope or other disease related glyco-antigens.

DRUG DISCOVERY

Modern pharmaceutical research and development was instated with the transition from folklore based medicine to the discovery and isolation of medicaments using modern chemistry. Since the 1950s drug discovery focused on testing large numbers of candidate compounds on a variety of animal models in an effort to identify pharmaceutical active compounds. As such, discovery of new drug candidates necessitated screening of diverse sources of compounds for potential therapeutic activities. These sources included, for example, known chemicals and drugs for which novel therapeutic activities were searched, fermentation broths and compounds excreted and/or extracted from plant or marine organisms, etc. (Granellin, 1992).

During the 1970s and 1980s, advances in the fields of biochemistry, molecular biology, cellular biology and structural (and functional) biology have led to a better understanding of the biochemical and molecular processes leading to the development and the progression of various diseases. This, in turn, has led to the development of protein-based primary screening assays, which replaced the more cumbersome and time consuming methods of screening for drug candidates in animal models (Nicholls, 1991).

In addition, advances in X-ray crystallography and computational chemistry, shed new light on the physical processes governing molecular recognition and interaction events of receptors and their ligands, leading to the development of what is known as the "rational drug design" approach (Hendrickson, 1991).

Understanding the three dimensional structure of peptides and proteins, and having the ability to manipulate such structures both virtually through molecular modeling and physically through molecular cloning techniques led researchers to the development of new drug candidates.

Unfortunately, due to the need for very highly skilled personnel and dedicated and complex equipment, "rational drug design" has failed to provide researchers with the drug design tool they had hoped for (Jacobs, 1994).

As such, in the early 1990's, the leading biotechnology and pharmaceutical firms turned to robotics and automation in an attempt to supplement the "rational drug design" approach. Automation enabled a "shotgun" approach to drug discovery, allowing for rapid screening of hundreds of thousands of compounds for desired biological activities. The new approach incorporated (i) combinatorics as a source of novel compounds; (ii) genomics, as a source of novel targets; and (iii) high throughput screening (HTS), as a method to cross screen various compounds/targets. As a result, the "shotgun" approach enabled researchers to disregard the technical hurdles associated with the previous approach and to focus on issues such as, "what to make?" or "how much diversity is required to produce a positive result?" (Hogan Jr., 1997).

COMBINATORIAL LIBRARIES

In the search for novel drug candidates, researchers looked to complement existing natural compounds which have been extensively screened, with a novel and diversified group of molecules not found in nature. As such, combinatorial libraries of newly synthesized novel compounds comprising nucleic or amino acid sequences were synthesized and screened for potential drug candidates.

Combinatorial libraries of such novel compounds or of novel targets can be categorized into three main categories.

The first category relates to the matrix or platform on which the library is displayed and/or constructed (Blondelle, 1996). As such, combinatorial libraries can be provided (i) on a surface of a chemical solid support, such as microparticles, beads or a flat platform; (ii) displayed by a biological source (e.g., bacteria or phage); and (iii) contained within a solution. In addition, three dimensional structures of various computer generated combinatorial molecules can be screened via computational methods (Gaasterland, 1998).

Combinatorial libraries can be further categorized according to the type of molecules represented in the library, which can include, (i) small chemical molecules; (ii) nucleic acids (DNA, RNA, etc.); (iii) peptides or proteins; and (iv) carbohydrates.

The third category of combinatorial libraries relates to the method by which the compounds or targets are synthesized, such synthesis is typically effected by: (i) in situ chemical synthesis (Borman, 1996); (ii) in vivo synthesis via molecular cloning (Kenan, 1994); (iii) in vitro biosynthesis by purified enzymes or extracts from microorganisms (Michels, 1998); and (iv) in silico by dedicated computer algorithms (Sansom, 1997).

Combinatorial libraries typified by any of the above synthesis methods can be further characterized by: (i) split or parallel modes of synthesis; (ii) molecules size and complexity; (iii) technology of screening; and (iv) rank of automation in preparation/screening.

In the split synthesis method, a combinatorial library which is synthesized, for example, on the surface of microparticles or beads, is divided into groups in which a unique first synthesis building block is attached to the beads. Groups of beads are then combined and separated to form new groups of unique diversity, the next building block is then added, and the process is repeated until the desired complexity is achieved. In the parallel synthesis method each of the compounds of the combinatorial library is synthesized separately, in a solution or immobilized to a matrix, requiring a unique and independent synthesis regimen for each of the compounds of the library.

The complexity of molecules in a combinatorial library depends upon the diversity of the primary building blocks and possible combinations thereof. Furthermore, several additional parameters can also determine the complexity of a combinatorial library. These parameters include (i) the molecular size of the final synthesis product (e.g., oligomer or small chemical molecule); (ii) the number of bonds that are created in each synthesis step (e.g., one bond vs. several specific bonds at a time); (iii) the number of distinct synthesis steps employed; and (iv) the structural complexity of the final product (e.g., linear vs. branched molecules).

Combinatorial libraries can be synthesized of several types of primary molecules, including, but not limited to, nucleic and amino acids and carbohydrates. Due to their inherent single bond type complexity, synthesizing nucleic and amino acid combinatorial libraries typically necessitates only one type of synthesis reaction. On the other hand, due to their inherent bond type complexity, synthesizing complex carbohydrate combinatorial libraries necessitates a plurality of distinct synthesis reactions.

Thus, the simplistic and repetition of both nucleic and amino acid polymers, allows for a relative simple synthesis method for combinatorial library of such constituents. On the other hand, since oligosaccharides are structurally much more complex, combinatorial libraries of complex carbohydrates are difficult to synthesize. As a result, the combinatorial carbohydrate libraries synthesized to date are of a very low complexity and typically include complex carbohydrate molecules consisting of no more than three building block constituents.

The evolution of nucleic and amino acid combinatorial libraries, has necessitated the utilization of screening techniques which capitalize on the unique nature of such libraries, such that rapid screening of diversified libraries can be effected.

For example, in order to identify specific interactions between a "probe" and a library constituent, a library can be constructed such that the identity and location of every single constituent is known or controlled at the synthesis stage. Such libraries are known as addressable libraries. By using the process of photolithography, light-directed—spatially addressable, parallel synthesizable libraries of peptides or oligonucleotides can be produced (Ramsay, 1997). In addition, microfabricated array of closed reaction chambers with micro-fluid systems are used for "Lab on a chip" oligonucleotides or chemical addressable library synthesis, (U.S. Pat. Nos. 5,643,738; 5,681,484; and 5,585,069, which are incorporated herein be reference). Using such an addressable technology enables the determination, during synthesis, of the nature and location of the library constituents.

In comparison, libraries that are synthesized employing the "one bead-one molecule" approach, in which the diversity is created by a split-and-pool synthesis, are screened by using probes conjugated to detectable moiety, e.g., a fluorescent molecule or an enzyme, such that beads interacting with a labeled probe can be identified, isolated and analyzed for composition (Schullek, 1997).

Since such screening methods are time consuming, tagged libraries approach has evolved mainly for the use with libraries created by the split-and-pool method. To accelerate the analysis of the isolated molecule of interest, the tagged libraries approach combines library members synthesis with parallel orthogonal synthesis of tagged building block standards (Janda, 1994; Chabala, 1995) or radio frequency tagged memory devices (Borman, 1996).

In order to screen large arrays, robotics and miniaturization equipment are utilized in high throughput screening (HTS) assays. In the past, HTS assays were basically upscaled laboratory assays. As such, and depending on the diversity of the screened molecules, the adaptation of a relatively simple assay to HTS involved miniaturization and automation of liquid handling, such that a large number of independent molecules can be screened relatively rapidly. Presently, more integrative approaches to HTS are developed and implemented. These approaches are referred to as 'Ultra Technologies' (UT, Sittampalam, 1997) or 'New Technologies' (NT, Burbaum, 1997). Such HTS methodologies vary between the split-and-pool or parallel synthesis methods. In the split-and-pool synthesis method the microparticles are used both for synthesis and for screening by pre treatment with assay reagents (Stinson, 1998). Improving the parallel synthesis methods necessitated additional miniaturization of the support matrix (Cargill, 1997). For example, if $10^6$ compounds are tested against 200 probes each year, this translates to $2\times10^8$ assays. If such assays are employed at a well volume of 100 $\mu$l each, containing 10 $\mu$l of the test compound of an approximal molecular weight of 500 g/mol, would require roughly two million microtiter plates of 96 wells, 20,000 liters of each target solution and 100 grams of each of the compounds.

Accordingly, new technologies for the miniaturization of the support matrix have been proposed. Such technologies are divided into open and closed vessel formats. The open vessel technology maintains compatibility with the standard 96-well plates and follows a geometric series of $N=n^2\times96$, where N is the number of wells, and n is an integer describing the possible packing density of a rectilinear array. Following this reasoning, the balance point between a microliter volume limitation and a suitable packing density is achieved by a plate with 1536 wells (n=4) having a well volume of 1–2 $\mu$l.

Screening of larger arrays requires further reduction of well volume to nanoliter amounts which further necessitates the use of the closed vessel format to prevent evaporation. Using fabrication techniques pioneered by the semiconductor industry, synthesis and analysis of nanoliter reaction volumes can be effected, such that a single four square-inch silicon wafer can support $10^5$ separate synthesis and bioassay reactions (Cheng, 1998).

Preparation methods of combinatorial libraries of small chemically synthesized organic molecules, such as nucleic acids (DNA, RNA and anti-sense RNA), peptides and biomimetics of peptide, such as peptoids and semi peptoids, etc., are now well established in the art and as such the technologies in most of the above categories and divisions (see Table 1 below) have been demonstrated.

TABLE 1

Combinatorial libraries categorization

| Category | Small chemical molecules | Nucleic Acids | Amino Acids | ates |
|---|---|---|---|---|
| Platform | | | | |
| Solution | + | + | + | + |

TABLE 1-continued

Combinatorial libraries categorization

| Category | Small chemical molecules | Nucleic Acids | Amino Acids | ates |
|---|---|---|---|---|
| Chemical support | + | + | + | + |
| Biological support | + | + | + | − |
| Computer | + | + | + | − |
| Synthesis | | | | |
| chemically synthesized | + | + | + | + |
| in vivo via molecular biology | − | − | + | − |
| in vitro via enzymatic synthesis | + | + | + | − |
| in silico via computer algorithm | + | + | + | − |
| Mode of combinatorial | | | | |
| Split-and-pool | + | + | + | + |
| Parallel | + | + | + | − |
| Complexity | | | | |
| Low Molecular Weight | + | + | + | + |
| Oligomer (H.M.W.) | − | + | + | + |
| One bond at a time | + | + | + | + |
| Several bonds a time | + | − | − | − |
| One reaction type | + | + | + | + |
| Several reaction types | + | − | − | − |
| Linear oligomer | − | + | + | + |
| One Branch in molecule | + | − | − | + |
| Highly Branched molecules | + | − | − | − |
| Screening methods | | | | |
| Isolation and analysis | + | + | + | + |
| Encoded | + | + | + | + |
| Spatially Addressable | + | + | + | − |
| Automation | | | | |
| a) Microparticles libraries | | | | |
| Pre treatment of the beads with the screening assay | + | + | + | + |
| Radio frequency tags | + | + | + | − |
| b) Addressable arrays | | | | |
| 96 well-based | + | + | + | − |
| HTS-NT | + | + | + | − | legend:
+: available;
−: non available.

In spite of the abundance of carbohydrates in nature and their important role in many biological processes, highly diversified and complex carbohydrate libraries have not been demonstrated (Borman, 1996). Moreover, although solid phase chemical synthesis of glycosidic bond products was proposed almost 30 years ago (Frechest, 1971, 1972; Guthrie, 1971), chemical synthesis of carbohydrate combinatorial libraries has only been demonstrated in recent years, and due to the limitations of chemical synthesis as further detailed hereinunder, such libraries constitute rather simple arrays of soluble untagged trisaccharide constituents.

Hindsgaul and co-workers demonstrated a 'random glycosylation' chemical approach to library synthesis which involves coupling a protected glycosyl donor with a sugar acceptor containing 3–5 free hydroxyls, to produce a mixture of 6 to 8 distinct carbohydrate products (Kanie, 1995). According to this method, following a glycosylation step the protecting groups are removed, and the coupled products are then separated from the starting monosaccharide building blocks via reverse phase chromatography.

Boons and co-workers reported a somewhat more direct chemical synthesis approach. To ensure the formation of regiospecific glycosidic linkages, they synthesized ten protected disaccharide acceptors containing one free hydroxyl group each. Each protected acceptor was separately reacted with a glycosyl donor to form 32 defined disaccharides. The disaccharide products were then mixed, a deprotection procedure was employed and the mixture was split into four subgroups. Each subgroup was then reacted with a different donor to give four libraries, each containing 64 trisaccharides. Finally, the products were separated by a tedious procedure of size-exclusion chromatography (Boons, 1996).

Chemical synthesis of a combinatorial carbohydrate library on a solid support was demonstrated by Kahne and co-workers (Liang, 1996). U.S. Pat. No. 5,700,916 teaches in this respect a carbohydrate library consisting of 1300 tagged di- and trisaccharide. This library was synthesized using the split-and-pool approach by coupling 12 different glycosyl donors to six different polymer-bound acceptors employing glycosylation methods incorporating anomeric sulfoxide as a glycosyl donor.

Chemical methods of preparing combinatorial carbohydrate libraries were also described by several other research groups (Rademann, 1996; Rodebaugh, 1997; Liang 1997, reviewed by Kahne, 1997; Arya, 1997, WO 97/34623; WO 97/35202; WO 98/08799; WO 98/40410; and U.S. Pat. No. 5,780,603). The above methods disclose chemically prepared carbohydrate libraries in which the carbohydrate constituents are attached to a non-sugar moiety via a glycosidic bond, or alternatively carbohydrate constituents of low structural complexity such as long uniform polyvalent chains or di-tetrasaccharides with 0–1 branching.

More recently, a synthetic oligosaccharide-mimetic was demonstrated to be capable of replacing the glycosidic bonds with amide bonds, thereby forming "carbopeptoids" (Nicolaou, 1995) and "glycotides" (McDevitt, 1996), or with phosphodiester bonds, thereby forming "carbonucleotides" (Nicolaou, 1995). Although these saccharide-mimetic forms are structurally more complex than previously synthesized carbohydrates, their complexity level is far from that of naturally occurring complex carbohydrates (for example, see FIG. 1).

Wong and co-workers (Wong, 1998) chemically synthesized core building blocks with four different selectively removable protecting groups, to yield a pentasaccharide-mimetic with four orthogonal glycosidic bonds.

Although carbohydrate libraries of limited complexity have been synthesized using various chemical methods, a combinatorial library of complex carbohydrates with a high rank of structural complexity resembling natural complex carbohydrates (e.g., highly branched structures) has not yet been produced. Furthermore, synthesizing such libraries using an addressable parallel synthesis approach which would enable rapid screening of library constituents has never been proposed or discussed by the prior art (see Table 1 above).

This is possibly due to the fact that chemical synthesis methods are still molded by the classical selective protection/deprotection strategies, making the length of the synthesized molecule the major contributor to the complexity thereof (Grout, 1998). It was calculated that to encompass all the possible linear and branched isomers of a hexamer oligosaccharide, more than $10^{12}$ distinct structural forms would be needed (Laine, 1994). Synthesis of such an array would be impractical by a chemical synthesis method utilizing selective protection-deprotection groups. In such a method the formation of mixtures of anomers which disable or terminate directed carbohydrate specific chain formation is unavoidable, and as such controlling the formation of such anomeric centers generated during synthesis, is impossible.

In order to synthesize combinatorial libraries of complex carbohydrates with high order of complexity and diversity one must seek alternative, non-chemical, methods of synthesis.

Enzymes are high fidelity biocatalists which are in prevalent use in the synthesis of organic compounds. As such, enzymes can be employed in a carbohydrate synthesis method which avoids the above mentioned limitations inherent to the prior art chemical synthesis methods. Enzymatic synthesis of glycosidic bonds displays high stereo- and regioselectivity, and as such, the employment of enzymes in the synthesis of complex carbohydrates abolishes the need for protected monomers and negates the problems inherent to the incorporation of such protected building blocks (Grout, 1998).

Nature employs four types of enzymes for in vivo biosynthesis of glycosidic bonds (see Table 2 below). The basic common division segregates these enzymes according to the Leloir pathway (Leloir, 1971) and the non-Leloir pathway. Leloir pathway enzymes are responsible for the biosynthesis of most N- and O-linked glycoproteins and other glycoconjugates in mammalian systems. The N-linked pathway involves an initial biosynthesis of a dolichol pyrophosphoryl oligosaccharide intermediate in the endoplasmic reticulum by mannosyl and N-Acetylglucosyl transferases. This oligosaccharide structure undergoes further glucosylation and is then transferred via an oligosaccharidetransferase to an aspargine residues of a growing peptide chain (Kornfeld, 1985). Prior to transport into the Golgi apparatus (GA), the glucose and some mannose residues are removed by glycosidases to reveal a core pentasaccharide. Additional monosaccharides are then added sequentially by glycosyltransfrases in the GA, in a process known as O-linked glycosylation, which is initiated in the GA by the addition of a monosaccharide to serine or threonine via a glycosidic bond and continues by the sequential addition of monosaccharides (Kornfeld, 1985). Glycosyltransferases of the Leloir pathway utilize only eight nucleoside sugars as monosaccharide donors for the synthesis of most oligosaccharides (see Table 3 below).

TABLE 2

Enzyme types used for in vitro synthesis of glycosidic bonds

| Enzyme type | Leaving group | Reference |
|---|---|---|
| Phosphorylase | —O—PO₃ | Hassid, 1950 |
| Glycosidase | —OR; F or —OH | Nilsson, 1988 |
| Transglycosidase | —O-Sugar or - - O—R | Schenkman, 1991 |
| Glycosyltransferase | —O-UDP; —O-GDP; —O-CMP | Hunez, 1980 |

TABLE 3

Glycosyltransferases of the Leloir pathway

| Enzyme | Donor |
|---|---|
| Glucosyltransferase | Uridinediphosphate-Glucose (UDP-Glc) |
| N-Actylglucosaminyltransferase | Uridinediphosphate-N-acetyl-glucoseamine (UDP-GlcNAc) |
| Galactosyltransferase | Uridinediphosphate-Galctose (UDP-Gal) |

TABLE 3-continued

Glycosyltransferases of the Leloir pathway

| Enzyme | Donor |
|---|---|
| N-Actylgalctosaminyltransferase | Uridinediphosphate-N-acetyl-galctoseamine (UDP-GalNAc) |
| Mannosyltransferase | Guanidinediphosphate-Mannose (GDP-Man) |
| Fucosyltransferase | Guanidinediphosphate-Fucose (GDP-Fuc) |
| Glucoronic acid transferase | Uridinediphosphate-Glucoronic acid (UDP-GlcUA) |
| Sialyltransferase | Cytosinediphosphate-N-acetyl-neuraminic acid (CMP-NeuAc) |

The non-Leloir pathway employs additional monosaccharides, such as anionic or sulfated sugars which are also founds in mammalian cells. A very diverse pool of yet additional monosaccharides which are not utilized by either pathway (e.g., rhamnose and arabinose; see Table 4 below) are also present in microorganisms, plants and invertebrates (Oths, 1990; Mengling, 1998).

TABLE 4

Monosaccharide presents only in microorganisms and plants (Gleeson, 1988)

| Monosaccharide found in microorganisms and in plants, but not in animals | Monosaccharide found in microorganisms, plants and in animals |
|---|---|
| Arabinose | Glucose |
| Apiose | Galactose |
| Fructose | Mannose |
| Galacturonic acid | Fucose |
| Rhamnose | Xylose |
| Aceric Acid (3-C-carboxy-5-deoxyl-xylose) | N-Acetylglucosamine |
| | N-Acetylgalactosamine |
| | Glucuronic acid |

Two main strategies have been proposed for in vitro enzyme catalyzed synthesis of oligosaccharide. According to the first strategy, glycosidases or glycosyl hydrolases are employed in a reverse hydrolysis reaction (WO 87/05936; WO 98/40512; and U.S. Pat. No. 5,532,147, Nilsson, 1988 and 1996; Watt, 1997), while according to the second strategy, glycosyltransferases are employed in a sequential synthesis method (Hunez, 1980; Toone, 1989). Due to the high yields and stereo- and regioselective specificity displayed by the second strategy it is considered to be the preferred approach (David, 1991; Wong, 1992). The second strategy, which is extensively discussed in the prior art (see, for example, Grout, 1998; Watt, 1997; Ichikawa, 1997; Wong, 1996; U.S. Pat. No. 5,583,042; and WO 96/32492), was exploited for the synthesis of a very narrow range of oligosaccharide molecules, ranging from 2 to 5 units in size utilizing seven of the eight Leloir monosaccharide species formed with only 0–1 branching bonds.

In nature, the use in combinations of all four types of enzymes (see Table 2 above) produces a complex array of oligosaccharides. On the other hand, very few descriptions of combined methods of enzymatic in vitro glycosidic bond synthesis were recorded.

Such methods can incorporate, in combination, a glycosidase and a glycosyltransferase (β-galactosidase and a (2,6) sialyltransferase) to produce a narrow range of oligosaccharide products (Herrmann, 1993; Nilsson 1988). Alternatively, a transglycosidase can also be used in combination with the above enzymes (e.g., trans-sialidase from *Trypanosoma cruzi*, Schenkman, 1991). Utilization of phosphorylase to transfer a sugar 1-phosphate donor to 2-keto-sugars has also been described as early as the 1950s (Hassid, 1950) but this strategy was not further pursued.

Enzymatic synthesis of complex carbohydrates on solid support was first proposed in the 1980s by Zehavi et al. (1983 and 1984). Zehavi and co-workers attached a glycosyl unit to 4-hydroxymethyl-3-nitrobenzoate to create a photo-labile linker. This saccharide-linker was coupled to an amino functionalized water-compatible support, such as polyacrylamide-gel polymer or polyvinyl alcohol, via an amide linkage (Zehavi, 1984). The polymer-bound glycoside was then galactosylated using 1,4 galactosyltransferase.

By combining chemical synthesis steps along with an enzymatic sugar chain elongation steps, the solid-phase chemo-enzymatic synthesis of the Lewis X glycopetide antigen (Halcomb, 1994; Seitz, 1997), as well as synthesis of a sialylated unodecasaccharide-aspargine conjugate in which the α-2,6 sialyl residue was enzymatically added to a chemically synthesized decasaccharide (Unverzagt, 1996) has been effected. In addition, enzymatic synthesis of a sialylated Lewis X antigen has also been accomplished on an activated silica support (Schuster, 1994). This glycopeptide was created in relatively high yields by three repetitive enzymatic glycosylation steps which resulted in four attached saccharide units on the peptide. An excellent yield was also reported for the synthesis of a glycopeptide via enzymatic glycosylation of a polyethyleneglycol-polyacrylamide copolymer solid support (Meldal, 1994).

To date, the discovery of new carbohydrate-derived pharmaceutical agents still lags far behind that of other classes of molecules, such as proteins. This lag is mostly attributed to the unavailability of an efficient and comprehensive synthesis method applicable for producing diverse and complex carbohydrate species. Since complex carbohydrates are both difficult to synthesize and to analyze, it is not feasible to employ the above described prior art methods for such tasks.

Despite these limitations, three aspects of carbohydrate medicinal chemistry and biochemistry were extensively studied: (i) specific interference with biosynthesis of bacterial cell-wall (Mengling, 1998); (ii) unique markers to malignant tumors (Orntoft, 1995; Kobata, 1998); and (iii) participation of cell-surface oligosaccharide markers in cell-to-cell communication, cell adhesion, cell infection and cellular differentiation (Simon, 1996).

These aspects of carbohydrate medicinal chemistry and biochemistry were studied using chemically synthesized complex carbohydrate species. Synthetic complex carbohydrates have proven to be an important tool for the developing glyco-therapeutic field, but the limitations inherent to the chemical synthesis process and as such to diverse combinatorial libraries produced thereof, impedes significant progress in this field.

For example, the CarbBank database (Complex Carbohydrate Structure Database-CCSD) includes 48,956 records (22,048 unique structures) which were derived from published articles and were compiled by the Georgia University project-Complex Carbohydrate Research Center (CCRC). These carbohydrates are grouped according to their complexity in FIG. 2. More than 58% of the entries are branched molecular structures that are practically impossible to synthesize using present day chemical synthesis methods. FIG. 3 is a histogram representing the distribution, in percentages, of the number of sugar residues present in the complex carbohydrates found in the CarbBank database. Although 44% of all the complex carbohydrates in the database posses 6 or more residues, chemical or enzymatic synthesis of such complex carbohydrates has not been extensively practiced, in particular not in context of a library.

Difficulties are further compounded when one wishes to construct a combinatorial library of such entities, necessitating parallel synthesis of a multitude of complex carbohydrates. As such, using present day chemical synthesis methods to synthesize combinatorial arrays of addressable complex carbohydrate entities is of a paramount challenge.

There is thus a widely recognized need for, and it would be highly advantageous to have, methods for synthesizing and screening complex carbohydrate combinatorial libraries of substantial structural complexity and diversity.

SUMMARY OF THE INVENTION

According to one aspect of the present invention there is provided a combinatorial complex carbohydrate library comprising a plurality of addressable complex carbohydrate structures.

According to another aspect of the present invention there is provided a method of producing an addressable combinatorial complex carbohydrate library, the method comprising the steps of (a) providing a solid support having a plurality of locations; and (b) enzymatically synthesizing a plurality of complex carbohydrate structures, each of the plurality of complex carbohydrate structures being attached to at least one addressed location of the plurality of locations, thereby producing the addressable combinatorial complex carbohydrate library.

According to further features in preferred embodiments of the invention described below, each of the addressable complex carbohydrate structures is attached to a solid support.

According to still further features in the described preferred embodiments attaching each of the addressable complex carbohydrate structures to the solid support is effected by a linker.

According to still further features in the described preferred embodiments the linker is cleavable, preferably under conditions that are harmless to carbohydrates.

According to still further features in the described preferred embodiments the linker is selected so as to allow attaching thereto a p-Nitrophenyl, amine or squaric acid derivative of a sugar.

According to still further features in the described preferred embodiments the linker includes at least two contiguous covalent bonds.

According to still further features in the described preferred embodiments the linker is selected from the group consisting of an amino acid, a peptide, a non-glycosylated protein, a lipid, a ceramide, dolicol phosphate, a cyclodextrin, an oligosaccharide, a monosaccharide, an alkyl chain and a nucleic acid.

According to still further features in the described preferred embodiments the linker is of a length of at least 20 Angstrom.

According to still further features in the described preferred embodiments the solid support is selected from the group consisting of addressable microparticles, addressable beads and a flat platform.

According to still further features in the described preferred embodiments the flat platform is selected from the group consisting of a microtiterplate, a membrane and a chip.

According to still further features in the described preferred embodiments the microtiterplate is an addressable microfabricated array of closed reaction chambers supplemented with micro-fluid systems. The reaction chambers are preferably of a density of 4–25 per square cm, each having a volume of 50–1000 nanoliter.

According to still further features in the described preferred embodiments the solid support is a chip and further wherein different complex carbohydrate structures of the plurality of addressable complex carbohydrate structures are arranged in patches spaced not more than 2.25 mm center to center According to still further features in the described preferred embodiments the solid support is of a substance selected from the group consisting of polystyrene cross-linked with divinylbenzene, polyethylene glycol-polystyrene block copolymer, polyamides, polyacrylamide, polymethacrylamide, silica, glass, quartz, plastic and cellulose.

According to still further features in the described preferred embodiments at least one of the plurality of addressable complex carbohydrate structures includes at least two contiguous saccharide units of a single species.

According to still features in the described preferred embodiments at least one of the plurality of addressable complex carbohydrate structures includes at least one branch.

According to still further features in the described preferred embodiments at least one of the at least one branch is formed of identical core and branching saccharide units.

According to still further features in the described preferred embodiments at least one of the plurality of addressable complex carbohydrate structures includes at least 5 saccharide units.

According to still further features in the described preferred embodiments the plurality of addressable complex carbohydrate structures are a representation including non-natural complex carbohydrates.

According to still further features in the described preferred embodiments the plurality of addressable complex carbohydrate structures are a representation including natural complex carbohydrates.

According to still further features in the described preferred embodiments the natural complex carbohydrates are derived from a human source.

According to still further features in the described preferred embodiments the human source is selected from the group consisting of a tissue, cells and body fluids.

According to still further features in the described preferred embodiments the plurality of addressable complex carbohydrate structures are a representation of domains of at least one natural complex carbohydrate.

According to yet another aspect of the present invention there is provided a method of identifying a complex carbohydrate capable of binding an entity, the method comprising the steps of (a) producing an addressable combinatorial complex carbohydrate library by (i) providing a solid support having a plurality of locations; and (ii) enzymatically synthesizing a plurality of complex carbohydrate structures, each of the plurality of complex carbohydrate structures being attached to at least one addressed location of the plurality of locations, thereby producing the addressable combinatorial complex carbohydrate library; and (b) screening the addressable combinatorial complex carbohydrate library with the entity for identifying the complex carbohydrate capable of binding the entity.

According to further features in preferred embodiments of the invention described below, the entity is a candidate for a biologically active material, the method serves for identifying a complex carbohydrate which is a target for the candidate for a biologically active material.

According to still further features in the described preferred embodiments the entity is a ligand known to bind a specific natural complex carbohydrate and further wherein the addressable combinatorial complex carbohydrate library is a representation of domains of the specific natural complex carbohydrate, the method serves for identifying a specific domain of the domains which binds the ligand.

According to still further features in the described preferred embodiments the entity is a potential drug.

According to still another aspect of the present invention there is provided a method of diagnosing a disorder characterized by a self or non-self complex carbohydrate structures and elicitation of antibodies there against, the method comprising the steps of (a) producing an addressable combinatorial complex carbohydrate library representing the self or non-self complex carbohydrates by (i) providing a solid support having a plurality of locations; and (ii) enzymatically synthesizing a plurality of complex carbohydrate structures, each of the plurality of complex carbohydrate structures being attached to at least one addressed location of the plurality of locations, thereby producing the addressable combinatorial complex carbohydrate library; and (b) reacting the addressable combinatorial complex carbohydrate library with antibodies derived from a patient suspected of having the disorder to thereby generate a pattern of the locations to which the antibodies bind, such that by comparing the pattern with a known pattern characterizing a healthy individual, a diagnosis of the disorder is obtainable.

The present invention successfully addresses the shortcomings of the presently known configurations by providing a combinatorial complex carbohydrate libraries and methods for their manufacture and screening.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 4 is a table representing the stepwise enzymatic synthesis of the complex carbohydrate structure of FIG. 1. In each step, the enzymatic reaction (ER) is listed (see Table 7 for details) and the added monosaccharide unit is marked by a gray background. "S" represents the solid support onto which the complex carbohydrate is immobilized and the synthesis reaction occurs.

DESCRIPTION OF THE PREFERRED EMBODIMENTS

Figures 1, 2, 3:
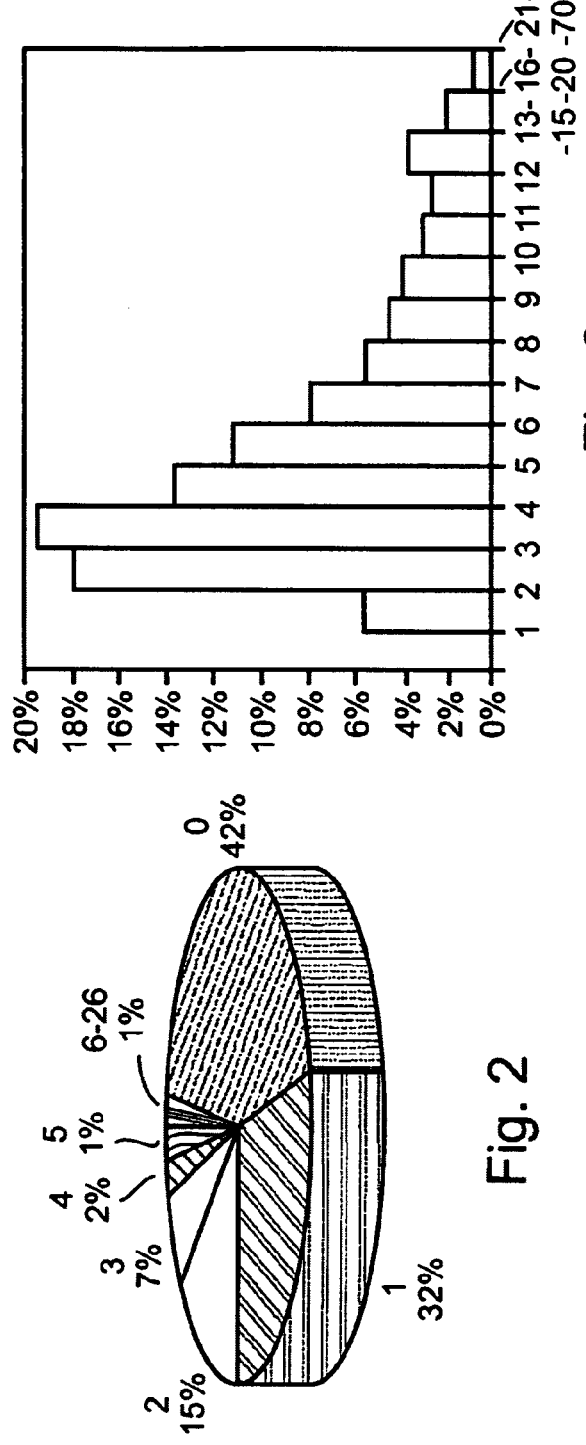
FIG. 1 is a formula of a complex carbohydrate of 14 monosaccharide units of five different types with three branching points. This complexity, which can be effected by the method of the present invention cannot be effected by any chemical or enzymatic synthesis methods currently known in the art. This Figure shows the monosaccharide types by name, the anomers (reactive centers) and bond types, as well as the branching points.
FIG. 2 represents a statistical study on the occurrence of branching in the complex carbohydrate records of the CCSD database. The CCSD database includes 48,956 records which were derived from published articles and were compiled by the Georgia University Project-Complex Carbohydrate Research Center-CCRC. Each slice of the pie shown represents, in percentage, the number of branches (0–26) occurring in the complex carbohydrates of the database. Statistical analysis was performed using CarbBank 3.2.009.
FIG. 3 is a histogram representing the distribution, in percentages, of the number of sugar residues present in the complex carbohydrates found in the CarbBank database. Although 44% of all the complex carbohydrates in the database posses 6 or more residues, chemical or enzymatic synthesis of such complex carbohydrates has not been extensively practiced, in particular not in context of a library.

The present invention is of combinatorial complex carbohydrate libraries and of methods for the synthesis thereof, which can be used for (i) identification of complex carbohydrate drugs; (ii) identification of complex carbohydrate associated receptors or proteins as potential new carbohydrate related targets for drug therapy; (iii) identification of biologically-active complex carbohydrates; (iv) identification of specific complex structural carbohydrate elements as potential new targets for drug therapy; (v) identification of the active sites of known complex carbohydrate structures; (vi) identification of new glyco-markers in complex carbohydrate structures; and (vii) detection of antibodies formed against a cancer-related glyco-marker or other disease related glyco-antigens.

The principles and operation of the combinatorial complex carbohydrate libraries and the methods for the synthesis thereof according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Enzymes for synthesis of complex carbohydrate libraries:

The enzymatic synthesis of complex carbohydrate combinatorial libraries according to the present invention is effected by glycosyltransferases, glycosidases and transglycosidases. These enzymes can be obtained from different sources using different strategies as describe herein below.

Enzymes derived from natural sources: To date, more than two hundred different kinds of glycosyltransferases, transglycosidases and glycosidases active on a large number of substrates and donors have been extensively characterized. These enzymes are found in mammalians cells, plant cells, invertebrate cells and microorganisms, (for references see Palcic, 1994 and Nilsson, 1996 which are incorporated by reference as if fully set forth herein).

Recombinant enzymes: The coding sequences of many glycosyltransferases and transglycosides have been cloned, and the acceptor substrate specificity of each of the recombinant enzymes encoded thereby have been characterized. Table 5 below lists some of the cloned glycosyltransferases and their respective acceptor substrate specificity. Enzymes for which the coding sequences have been cloned can be produced in sufficient quantities using standard recombinant DNA techniques. Since most of these enzymes require post translational modifications for functionality, expression is preferably effected in insect cell cultures (Toki, 1997; Tan, 1995). In addition, in the case of soluble enzymes for which the catalytic domain(s) have been characterized, expression can be effected for the domain sequence only, providing it retains the catalytic activity and substrate specificity of the holoenzyme (Vries, 1997). Other possible expression systems for soluble glycosyltransferases also include secretion from mammalians tissue-cultures (see for example U.S. Pat. No. 5,032,519, which is incorporated by reference as if fully set forth herein).

TABLE 5

Partial list of cloned glycosyltransferases and their acceptors.

| Enzyme | Acceptor | E.C. number | Reference |
| --- | --- | --- | --- |
| α2,3 sialyl transferase | D-Gal-β(1,3)-D-GalNAc-R | 2.4.99.4 | Chang 1995, Gillespieet 1992, Kurosawa 1995 |
| β2,6 sialyl transferase | D-Gal-β(1,4)-D-GlcNAc-R | 2.4.99.1 | Grundmann 1990, Kurosawa 1994, Hamamoto 1993 |
| α2,3 sialyl transferase | D-Gal-β(1,4)-D-GlcNAc-R | 2.4.99.6 | Kitagawa and Paulson 1993, Wen 1992 |
| α2,8 sialyl transferase | D-NeuAC-α(2,3)-D-Gal-β-R | 2.4.99.8 | Nara 1994 |
| α1,2 fucosyl transferase | D-Gal-β-R | 2.4.1.69 | Larsen 1990, Hitoshi 1995 |
| α1,3 fucosyl transferase | [D-Gal-β(1,4)]-D-GlcNAc-R | 2.4.1.152 | Kudo 1998 |
| α1,6 fucosyl transferase | [D-Man-β(1,4)-D-GlcNAc-β(1,4)]-D-GlcNAc-R | 2.4.1.68 | Voynow 1991, Uozumi 1996, Yanagidani 1997 |
| β1,4 mannosyl transferase | D-GlcNAc-β(1,4)-D-GlcNAc-R | none | Albright and Robbins 1990 |
| α1,2 mannosyl transferase | D-Man-α(1,2)-Man-R | 2.4.1.131 | Romero 1997 |
| α1,3 mannosyl transferase | D-Man-α(1,2)-Man-α(1,2)-Man-R | none | Yip 1994 |
| α1,3 galactosyl transferase | D-Gal-β(1,4)-D-GlcNAc-R. | 2.4.1.151 | Joziasse 1989, Larsen 1989, Strahan 1995 |
| β1,4 galactosyl transferase | D-GlcNAc-R | 2.4.1.38 | Masibay and Qasba 1989 |

TABLE 5-continued

Partial list of cloned glycosyltransferases and their acceptors.

| Enzyme | Acceptor | E.C. number | Reference |
| --- | --- | --- | --- |
| α1,3 N-Acetylgalactose aminyltransferase | [L-Fuc-α(1,2)]D-Gal-R | 2.4.1.40 | Yamamoto 1990, |
| β1,4 N-Acetylgalactose aminyltransferase | [D-NeuAC-α(2,3)]D-Gal-β(1,4)-D-Glc-R | 2.4.1.92 | Hidari 1994, Nagata 1992 |
| N-Acetylgalactose aminyltransferase | Ser/Thr | 2.4.1.41 | Meurer 1995, Hagen 1993 |
| β1,3 glucoronosyl transferase | D-Gal-β(1,3)-D-Gal-β(1,4)-D-Xly-β-R | 2.4.1.135 | Kitagawa 1998 |
| β1,6 N-Acetylglucose aminyltransferase | D-Gal-β(1,4)-D-GlcNAc | 2.4.1.150 | Bierhuizen, 1993 |
| β1,6 N-Acetylglucos aminyltransferase | D-GalNAc-β(3,1)-D-Gal(R) | 2.4.1.102 | Bierhuizen 1992 |
| β1,2 N-Acetylglucos aminyltransferase | D-Man-α(1,3)[R1]D-man-β(1,4)-R2 | 2.4.1.101 | Kumar 1990, Pownall 1992, Sarkar 1991, Fukada 1994 |
| β1,4 N-Acetylglucos aminyltransferase | D-Man-α(1,3)[R1]-D-Man-β(1,4)-R2 | 2.4.1.145 | Minowa 1998 |
| β1,2 N-Acetylglucos aminyltransferase | D-Man-α(1,6)[RI]D-man-β(1,4)-R2 | 2.4.1.143 | Tan 1995 |

Methods for identifying and cloning new enzymes: In addition to the presently available natural and recombinant glycosyltransferase, the identification and isolation of novel glycosyltransferases can be undertaken. Glycosyltransferases which are useful for complex carbohydrate library synthesis, can be identified and isolated from cell types which posses the complex carbohydrate structures typically synthesized by these desired glycosyltransferases. Affinity chromatography techniques with an immobilized acceptor as a ligand are well known in the art and enable a simple one-step separation of a desired glycosyltransferase (see in this respect U.S. Pat. No. 5,288,637, which is incorporated herein by reference). Once a glycosyltransferase is identified and isolated, it can be partially sequenced and the gene encoding therefor cloned. Technologies for cloning glycosyltransferases genes are well-established, and many examples and strategies for cloning glycosyltransferase genes are reviewed in the prior art (see, for example, Schachter, 1994 and WO 95/02683, which are incorporated by reference as if fully set forth herein).

Another possible source for novel glycosyltransferase sequences resides within the DNA and Protein databases. With the rapid accumulation of new DNA and protein sequence data, sequence alignment techniques can be used for the identification of new glycosyltransferases. For example, 110 distinct cDNAs and genes from animal, yeast, plants and bacteria, whose protein products contain the characteristic "signature sequence" of the UDP glycosyltransferase gene super family were identified (Mackenzie, 1997). Using these signature sequences or motifs, one skilled in the art can screen relevant databases for novel glycosyltransferases. For example, three new arabinosyltransferase genes were identified in the completely sequenced genome of Mycobacterium tuberculosis via sequence homology comparison to arabinosyltransferase genes from Mycobacterium smegmatis (Cole, 1998).

Utilizing enzymes modified by directed evolution: Enzymes with modified affinities or altered substrate donor or acceptor specificities could also be employed in the synthesis of certain complex carbohydrates. For example, the synthesis of complex carbohydrate structures composed of identical repeating monosaccharide units connected in the same regio-specific orientation, such as, D-man-α(1,2)-D-Man-α(1,2)-D-man-α(1,2)-R, requires the use of an α-1,2 mannosyltransferase with an acceptor specificity to α-1,2 mannose. Employing the native enzyme in the presence of GDP-Mannose and the acceptor D-man-α(1,2)-R immobilized onto a solid support, would result in an uncontrolled polymerization reaction which would create long polymer chains of the oligo-mannose, [D-Man-α(1,2)]$_n$-R. In order to synthesize an oligo-mannose with a defined number of mannose units (three in the above example), a controlled stepwise process is required. The ability to control undesired polymerization can be achieved by using a modified glycosyl donor, and a unique glycosyltransferase with a modified donor specificity. Such a modified enzyme, would be employed for the addition of a modified GDP-Man to immobilized acceptor D-manα(1,2)-R. The modification of the mannoside moiety of the GDP-Man will then prevent addition of the next mannose moiety since the acceptor to this manosidetransferase is D-man-α(1,2)-R and not D-(modified man)-α(1,2)-D-man-α(1,2)-R. Following this reaction, any excess of the modified donor and the enzyme is washed out and the modifying group is removed, thereby enabling the subsequent repeat of the same enzymatic step. This controlled process is continued until the desired number of mannose molecules are assembled into the newly formed carbohydrate. To this effect, the modifying group can be a chemical residue attached to the donor at any position, but position 1. This modifying group can then be selectively removed by either an enzymatic or chemical reaction, such that the modifying group is released without imposing damage to the complex carbohydrate molecule.

Table 6 below lists some of the presently available saccharide modifying groups, classified by their method of removal (Kunz, 1997, which is incorporated by reference as if fully set forth herein, and references cited therein). Additional monosaccharide can also be used as modifying groups and as such, removal thereof can be effected by using specific glycosidases that will not affect the existing complex carbohydrate structure (Peieto, 1995).

TABLE 6

Available saccharide modifying groups classified by their cleavage (Kunz and Schultz, 1997; and references cited therein)

| Cleavage principle | Cleavage reagents | Modifying group |
| --- | --- | --- |
| Hydrogenolysis | H$_2$/Palladium | benzyloxycarbonyl<br>benzyl ether<br>benzyl ester<br>methoxybenzyl ether |
| Acidolysis | Trifluoroacetic acid<br>formic acid<br>HCl/ether | tert-butyloxycarbonyl<br>tert-butyl ether<br>tert-butyl ester<br>methoxybenzyl ether |
| Base promoted cleavage | Morpholine, piperidine<br>NaOMe/MeOH<br>NH$_2$NH$_2$/MeOH | 9-fluorenylmethoxy carbonyl<br>O-acetyl |
| Reductive cleavage | Zn/acetic acid | 2,2,2-trichloroethoxycarbonyl |
| Oxidative cleavage | Ceric ammonium nitrate | methoxybenzyl ether |
| Metal complex catalyzed cleavage | [(Ph$_3$P)$_4$Pd$^0$]/nucleophile | allyl ester |
| Photolysis | hv | O-nitrobenzyl |

TABLE 6-continued

Available saccharide modifying groups classified by their cleavage (Kunz and Schultz, 1997; and references cited therein)

| Cleavage principle | Cleavage reagents | Modifying group |
| --- | --- | --- |
| Enzymatic cleavage | lipase, esterase, protease | alkyl and alkoxyalkylesters |

Thus, enzymes having modified donor and/or acceptor specificities can be prepared using the directed evolution approach. With the recent progress in the field of protein engineering, many examples of enzymes with engineered specificity obtained via directed evolution were described (for reviews of this field see: Kuchner, 1997; Harris, 1998, which are incorporated herein by reference). A directed evolution of an enzyme specificity is achieved by random sequential generation of region directed or site directed mutagenesis of the gene or genes encoding the enzyme, followed by selection or screening for clones exhibiting desired specificity and activity. For example, Moore and co-workers performed seven rounds of DNA shuffling to change the substrate specificity of paranitrobenzyl-esterase to a novel antibiotic substrate (Moore, 1996). Zhang and co-workers performed directed evolution of a fucosidase from galactosidase by DNA shuffling (Zhang, 1997). Shan and co-workers engineered an unnatural nucleotide specificity for the Rous Sarcoma Virus tyrosine kinase (Shan, 1997). Paulson and co-workers performed mutation of the sialyltransferase S-sialyl motif that alters the kinetics of the donor and acceptor substrates (Datta, 1998).

Parallel Addressable Enzymatic Synthesis of Combinatorial Complex Carbohydrate Libraries The following sections detail a step by step enzymatic preparation of a combinatorial complex carbohydrate library in accordance with the teachings of the present invention.

Enzymatic combinatorial complex carbohydrate library design: Enzymatic combinatorial complex carbohydrate library design includes, according to the present invention, determination of the complex carbohydrate constituents included within a specific library in accordance with an envisaged application thereof.

Determination of the complex carbohydrate members included within a

For example, in order to utilize an enzymatic combinatorial complex carbohydrate library of the present invention for identification of complex carbohydrates functional as drug targets, the complex carbohydrate members of the library are preferably derivatives or modificants of complex carbohydrates present in human cells. Screening such a library against other molecules derived from other sources, such as specific human cells or pathogens thereof, enables the identification of novel complex carbohydrates that function as receptors for these molecules, functioning in vivo as pathogen receptors, or involved in cell to cell recognition processes.

Similarly, in order to utilize an enzymatic combinatorial complex carbohydrate library of the present invention for identification of potential drugs, the complex carbohydrate members of the library are preferably synthesized similar or identical to natural complex carbohydrates present in human cells. Screening such a library with drug candidates derived from various natural and synthetic sources, enables the identification of drug candidates which bind to one or more of the complex carbohydrate structures of the library.

Another specific library according to the present invention contains complex carbohydrates dedicated for the identification of novel drug candidates. In this case, a library of maximized complex carbohydrate diversity which represents, among others, complex carbohydrate structures not found in nature, is generated. Such a library is thereafter screened for potential binding of pathogens or pathogen derived molecules. Alternatively, such a library is thereafter screened for potential binding of other disease inflicting molecules.

To identify active site domains within a known complex carbohydrate, a library in accordance with the present invention representing all of the possible domains of the complex carbohydrate is prepared. Screening this library for binding or bioactivity enables one to identify the active site domains of the known complex carbohydrate.

To detect antibodies generated against, for example, cancer-related glyco-epitopes (markers), organ transplantation related glyco-markers, or other glyco-markers in blood serum, a complex carbohydrate library of specific combinations of glyco-markers is prepared and screened. For example, one specific library can represent the glyco-markers of several cancer conditions. This library is thereafter screened against antibodies derived from human serum to identify the presence of antibodies against one or more of these glyco-markers.

To map glyco-markers related to, for example, cancer or organ transplantation, a complex carbohydrate library of specific combinations of carbohydrate members which are structural variations of the glyco-markers normally associated with such conditions is prepared and screened.

Other enzymatic combinatorial complex carbohydrate libraries, dedicated at other applications are envisaged and are within the broad scope of the present invention as claimed.

Enzymatic modules (EMs) construction: EMs construction includes evaluation of the required enzymatic reactions (ERs), glycosyl donors and acceptors and enzymes that are required for the synthesis of each complex carbohydrate of a library. EMs construction further includes optimization and process development of the required ERs with considerations given to reaction time, temperature and reagent concentrations. EMs construction further includes determination of the specific order in which the ERs should be utilized for every EM.

To enable the synthesis reactions employed, a specific sequence of enzymatic reactions (ERs) is determined for each complex carbohydrate constituent of a given library. For complex carbohydrates that have a linear non-branched structure, the ERs sequence follows that of the monosaccharide sequence of such linear non-branched structures in a stepwise fashion. For complex carbohydrates possessing branched structure(s) and/or repetitive monosaccharide units arranged in a linear assembly, unique synthesis processes should be designed employing unique EMs.

The following example provides the rational for selecting particular ERs to provide an EM tailored for the synthesis of a distinct complex carbohydrate. The final complex carbohydrate structure is described by FIG. 1 and the design process is described by FIG. 4 and Table 7. Such an EM is designed, according to the present invention, for each complex carbohydrate present in a given library. As further detailed hereinunder, consideration is given to efficiency when practically effecting each of the EMs while constructing a library according to the present invention.

TABLE 7

A partial list of ERs including their donors, acceptors and indexes

| index | extension | α/β | Pos. | acceptor | donor | E.C. |
|---|---|---|---|---|---|---|
| A1 |  | α | 3 | D-Gal-β(1,3)-D-GalNAc-R | CMP-NeuAC | 2.4.99.4 |
| A2 |  | α | 6 | D-Gal-β(1,4)-D-GlcNAc | CMP-NeuAC | 2.4.99.1 |
| A3 |  | α | 3 | D-Gal-β(1,4)-D-GlcNAc-R | CMP-NeuAC | 2.4.99.6 |
| A4 |  | α | 6 | D-GalNAc-α-R | CMP-NeuAC | 2.4.99.3 |
| A5 | [NeuAc-α(2,3)-D-Gal-β(1,4)] | α | 6 | D-GalNAc-α-R | CMP-NeuAC | 2.4.99.7 |
| A6 |  | α | 8 | D-NeuAc-α(2,3)-D-Gal-β-R | CMP-NeuAC | 2.4.99.8 |
| A7 |  | α | 8 | D-NeuAC-α(2,8)-D-NeuAC-R | CMP-NeuAC(modified) | none |
| B1 |  | α | 2 | D-Gal-β-R | GDP-L-Fuc | 2.4.1.69 |
| B2 | [D-Gal-β(1,4)] | α | 3 | D-GlcNAc-R | GDP-L-Fuc | 2.4.1.152 |
| B3 | [D-Man-β(1,4)-D-GlcNAc-β(1,4)] | α | 6 | D-GlcNAc-R | GDP-L-Fuc | 2.4.1.68 |
| B4 |  | α | 6 | D-GlcNAc-R | GDP-L-Fuc | none |
| B5 | [D-GlcNac-β-(1,4)] | α | 6 | D-GlcNAc-R | GDP-L-Fuc | none |
| B6 | [D-Gal-β(1,3)] | α | 4 | D-GlcNAc-R | GDP-L-Fuc | none |
| B7 | [D-Gal-β(1,4)] | α | 3 | D-Glc-R | GDP-L-Fuc | none |
| B8 |  | α | 3 | D-Glc-R | GDP-L-Fuc | none |
| B9 |  | α | 4 | D-GlcNAc-β-R | GDP-L-Fuc | none |
| B10 |  | α | 3 | D-GlcNAc-β-R | GDP-L-Fuc | none |
| B11 |  | α | 4 | D-GlcNAc-β(1,3)-Gal-R | GDP-L-Fuc | none |
| B12 |  | α | 3 | D-GlcNAc-β(1,6)-Gal-R | GDP-L-Fuc | none |
| C1 |  | β | 4 | D-GlcNAc-β(1,4)-D-GlcNAc-R | GDP-Man | none |
| C2 |  | α | 3 | D-Man-α(1,2)-Man-α(1,2)-Man-R | GDP-Man | none |
| C3 |  | α | 2 | D-Man-α(1,2)-Man-R | GDP-Man | 2.4.1.131 |
| C4 |  | α | 3 | D-Man-β(1,4)D-GlcNAc-β(1,4)-D-GlcNAc-R | GDP-Man | none |
| C5 | [D-Man-α(1,3)] | α | 6 | D-Man-β(1,4)D-GlcNAc-R | GDP-Man | none |
| C6 |  | β |  | dolicol phosphate | GDP-Man | 2.4.1.83 |
| C7 |  | α | 6 | D-Man-α(1,0)-R | GDP-Man | none |
| C8 |  | α | 3 | D-Man-α(1,0)-R | GDP-Man | none |
| C9 |  | α | 4 | D-GlcNAc-β(1,4)-R | GDP-Man | none |
| C10 |  | α | 3 | D-Man-β(1,4)D-GlcNAc-β(1-0)-R | GDP-Man | none |
| D1 |  | β |  | ceramide | UDP-Gal | 2.4.1.45 |
| D2 |  | β | 6 | D-Gal-β(1,4)-D-Gal-β(1,4)-D-Glc-ceramide | UDP-Gal | 2.4.1.154 |
| D3 |  | α | 3 | D-Gal-β(1,4)-D-GlcNAc-R. | UDP-Gal | 2.4.1.151 |

TABLE 7-continued

A partial list of ERs including their donors, acceptors and indexes

| index | extension | α/β | Pos. | acceptor | donor | E.C. |
|---|---|---|---|---|---|---|
| D4 | | β | 3 | D-Gal-β(1,4)-D-Xly-β-P | UDP-Gal | 2.4.1.134 |
| D5 | | β | 3 | D-GalNAc-R | UDP-Gal | 2.4.1.122 |
| D6 | [L-Fuc-α(1,2)] | α | 3 | D-Gal-R | UDP-Gal | 2.4.1.37 |
| D7 | | β | 4 | D-GlcNAc-R | UDP-Gal | 2.4.1.38 |
| D8 | | β | 4 | D-Xly-β-P | UDP-Gal | 2.4.1.133 |
| D9 | | β | 4 | D-Glc-R | UDP-Gal | 2.4.1.38 |
| D10 | | β | 3 | D-GlcNAc-R | UDP-Gal | none |
| D11 | | β | 3 | D-GlcNAc-β(1,3)-Gal-R | UDP-Gal | none |
| D12 | | β | 4 | D-GlcNAc-β(1,6)-Gal-R | UDP-Gal | none |
| E1 | | β | 3 | D-Gal-(1,4)-D-Gal-(1,4)-D-Glc-ceramide | UDP-GalNAc | 2.4.1.79 |
| E2 | [D-NeuAC-a(2,3)]- | β | 4 | D-Gal-β(1,4)-D-Glc-ceramide | UDP-GalNAc | 2.4.1.92 |
| E3 | [L-Fuc-α(1,2)] | α | 3 | D-Gal-R | UDP-GalNAc | 2.4.1.40 |
| E4 | | | | Ser/Thr | UDP-GalNAc | 2.4.1.41 |
| F1 | | | | sphingosine | UDP-Glc | 2.4.1.80 |
| G1 | | β | 3 | D-Gal-β(1,3)-D-Gal-β(1,4)-D-Xly-β-P | UDP-GlcA | 2.4.1.135 |
| H1 | | β | 3 | D-Gal-β(1,3)-D-GalNAc-R | UDP-GlcNAc | 2.4.1.146 |
| H2 | | β | 6 | D-Gal-β(1,4)-D-GlcNAc | UDP-GlcNAc | 2.4.1.150 |
| H3 | | β | 3 | D-Gal-β(1,4)-D-GlcNAc-β(1,X)R. | UDP-GlcNAc | 2.4.1.149 |
| H4 | [Gal-β(1,3)] | β | 6 | D-GalNAc-R | UDP-GlcNAc | 2.4.1.102 |
| H5 | | β | 3 | D-GalNAc-R | UDP-GlcNAc | 2.4.1.147 |
| H6 | [GlcNAc-β(1,3)] | β | 6 | D-GalNAc-R | UDP-GlcNAc | 2.4.1.148 |
| H7 | [D-Man-α(1,3)] | α | 2 | D-Man-α(1,2)-D-Man-α(1,2)-D-Man | UDP-GlcNAc | 2.4.1.138 |
| H8 | | β | 2 | D-Man-α(1,3)[R1]D-man-β(1,4)-R2 | UDP-GlcNAc | 2.4.1.101 |
| H9 | | β | 4 | D-Man-α(1,3)[R1]-D-Man-β(1,4)-R2 | UDP-GlcNAc | 2.4.1.145 |
| H10 | | β | 2 | D-Man-α(1,6)[R1]D-man-β(1,4)-R2 | UDP-GlcNAc | 2.4.1 143 |
| H11 | | β | 6 | D-Man-α(1,6)[R1]-D-Man-β(1,4)-R2 | UDP-GlcNAc | 2.4.1.155 |
| H12 | [D-GlcNAc-β(1,2)][D-GlcNAc-β(1,6)] | β | 4 | D-Man-α(1,6)R | UDP-GlcNAc | none |
| H13 | [D-Man-α(1,3)][D-Man-β(1,6)] | β | 4 | D-Man-β(1,4)R | UDP-GlcNAc | 2.4.1.144 |
| H14 | [D-GlcNAc-β(1,3)] | β | 6 | D-Gal-β(1,4)-D-GlcNAc | UDP-GlcNAc | none |
| H15 | | β | 3 | D-Gal-β(1,4)-D-Glc | UDP-GlcNAc | none |
| H16 | [D-GlcNAc-β(1,3)] | β | 6 | D-Gal-β(1,4)-D-Glc | UDP-GlcNAc | none |
| H17 | | β | 4 | D-GlcNAc-R | UDP-GlcNAc | none |
| H18 | | β | 4 | D-Man-(1,0)R | UDP-GlcNAc | none |
| H19 | [D-GlcNAc-β(1,4)] | β | 2 | D-Man-(1,0)R | UDP-GlcNAc | none |
| H20 | | β | 3 | D-Gal-β(1,4)-D-GlcNAc | UDP-GlcNAc | none |
| H21 | | β | 6 | D-Gal-R | UDP-GlcNAc | none |
| H22 | | β | 3 | D-Gal-R | UDP-GlcNAc | none |
| H23 | [D-GlcNAc-β(1,6)] | β | 3 | D-Gal-R | UDP-GlcNAc | none |
| H24 | [D-GlcNAc-β(1,6)] | β | 3 | D-Gal-R | UDP-GlcNAc-(4,1)α-Fuc | none |
| I1 | | α | 3 | D-Glc-β-Ser | UDP-Xyl | none |
| I2 | | α | 2 | D-Man-β(1,4)D-GlcNAc-β(1,4)-D-GlcNAc-R | UDP-Xyl | none |
| I3 | | α | 3 | D-Xyl-α(1,3)-D-Glc-β-Ser | UDP-Xyl | none |

The first step in the synthesis of the complex carbohydrate shown in FIG. 1 is effected, as shown in FIG. 4, by attachment of a first building block, GalNAc, onto a solid support (S) via an appropriate linker which is further described herein below.

The second step (D5, see Table 7 and FIG. 4 for details) in the synthesis of the complex carbohydrate shown in FIG. 1 involves transferring Gal from UDP-Gal to GalNAc-S by a β(1,3)-galactosyltransferases (E.C. 2.4.1.122).

The third step (H1, see Table 7 and FIG. 4 for details) in the synthesis of the complex carbohydrate shown in FIG. 1 involves the utilization of β(1,3)N-acetylglucosaminyltransferase (E.C. 2.4.1.146) to transfer an acetylglucoseamine group from UDP-GlcNAc to Gal-β (1,3)-GalNAc-S.

Then, a galactose unit is added to the acceptor (see FIG. 4), rather then a fucose unit because the specificity of the enzymes β(1,3)-fucosyltransferase (E.C. 2.4.1.152) to the acceptor Gal-β(1,4)-GlcNAc-R rather than to the naked GlcNac.

Thus, in the fourth step (D7, see Table 7 and FIG. 4 for details) in the synthesis of the complex carbohydrate shown in FIG. 1 galactose is added to GlcNAc-R using the enzyme β(1,4)galactosyltransferase (E.C. 2.4.1.38).

Following the fourth synthesis step described above, the synthesis process complicates since the galactose units branch into two antennas (branches). Since the structure of these antennas is identical at the branching point, yet different towards their non-reducing ends, an identical stepwise synthesis process that simultaneously forms the identical parts of the two antennas would not enable the subsequent synthesis of a unique reducing end for each of the antennas. Therefor, the synthesis of the two unique portions of each of the antennas proceeds in an independent stepwise fashion. In any case, in the example given, the β(1,3) branch has to be synthesized first because this antenna requires fucosylation. If the synthesis process would initiate with the other branch, directed fucosylation to the desired branch could not have been effected.

Thus, the fifth step (H3, see Table 7 and FIG. 4 for details) in the synthesis of the complex carbohydrate shown in FIG. 1 is effected using β (1,3)N-acetylglucosaminyltransferase (E.C. 2.4.1.149) to transfer acetylglucosamine from UDP-GlcNAc to Gal-β(1,4)-GlcNAc-R.

In the sixth step (D7, see Table 7 and FIG. 4 for details) in the synthesis of the complex carbohydrate shown in FIG. 1, a galactose unit is added to GlcNAc-R using a β(1,4) galactosyltransferase (E.C. 2.4.1.38).

In the seventh step (D3, see Table 7 and FIG. 4 for details) in the synthesis of the complex carbohydrate shown in FIG. 1, an additional galactose residue is added to Gal-α(1,4)-GlcNAc-R using α(1,3)galactosyltransferase (E.C. 2.4.1.151).

In the eighth step (H14, see Table 7 and FIG. 4 for details) in the synthesis of the complex carbohydrate shown in FIG. 1, branching is effected by using β(1,6)N-acetylglucosaminyltransferase on the Gal[GlcNAc-β(1,3)]β(1,4)-GlcNAc-R acceptor substrate.

The ninth step (B2, see Table 7 and FIG. 4 for details) in the synthesis of the complex carbohydrates shown in FIG. 1 involves two of the four GlcNAc monomers and is effected by α(1,3)fucosyltransferase (E.C. 2.4.1.152) which transfers fucose to Gal-β(1,4)-GlcNAc-R.

The tenth step (D7, see Table 7 and FIG. 4 for details) in the synthesis of the complex carbohydrate shown in FIG. 1 effects further elongation of the second antenna using an β(1,4)galactosyltransferase (E.C. 2.4.1.38) on the GlcNAc-R acceptor substrate.

In the eleventh step (A3, see Table 7 and FIG. 4 for details) in the synthesis of the complex carbohydrate shown in FIG. 1, a sialic acid monomer is appended to the Gal-β(1,4)GlcNAc-R of the antenna in an α(1,6) orientation using an α(2,3)Sialyltransferases (E.C. 2.4.99.6)

The twelfth step (A6, see Table 7 and FIG. 4 for details) in the synthesis of the complex carbohydrate shown in FIG. 1 effects further elongation of this antenna using an α(2,8) Sialyltransferases (E.C. 2.4.99.8), thereby adding another NeuAC unit to the NeuAC-α(2,3)-Gal-R substrate acceptor.

Further elongation of this antenna requires the use of a (2,8) polysialyltransferases with specificity to the NeuAC-α(2,8)-NeuAC-R substrate acceptor. Unfortunately, an enzymatic reaction with such an enzyme will cause uncontrollable polymerization of multiple sialic acid monomers rather than the required addition of only a single sialic acid monomer. Achieving a controllable addition of a single sialic acid monomer in each ER step necessitates the use of an enzyme with a modified donor specificity. As such, instead of using CMP-NeuAC as a donor substrate, this modified enzyme incorporates a modifying group to the glycan end. The presence of this modifying group prevents the unwanted polymerization of multiple monomers of sialic acid, since this enzyme cannot append sialic acid to the acceptor NeuAC(modified)-α(2,8)-NeuAC-R. In the last step of this ER the modifying group is removed.

Thus, in the final step (A7, see Table 7 and FIG. 4 for details) in the synthesis of the complex carbohydrate shown in FIG. 1, the modified enzyme α(2,8) polysialyltransferasease is employed along with the modified donor CMP-NeuAC and the acceptor NeuAC(modified)-α(2,8)-NeuAC-R, to thereby generate the complex carbohydrate shown in FIG. 1.

Table 8 below outlines the stepwise synthesis of the complex carbohydrate shown in FIG. 1, as outlined in FIG. 4.

TABLE 8

| EM | First immobilized monosaccharide | ERs sequence (the ERs details are shown in Table 7 and FIG. 4): |
|---|---|---|
| EM₁ | GalNAc-S | D5, H1, D7, H3, D7, D3, H14, B2, D7, A3, A6, A7 |

ERs selection for providing a desired EM is generated using a computer algorithm taking into account the complex carbohydrate structure and the available ERs. Such an algorithm can readily be programmed by one ordinarily skilled in the art, based on the donor-acceptor specificities of the various glycosyltransferases glycosidases and transglycosylases available.

Automated synthesis and screening: The EMs used in the construction of a combinatorial complex carbohydrate library according to the present invention are executed to produce a combinatorial complex carbohydrate library bound to a solid support using automated technology. Screening to identify bio-active complex carbohydrates cross reactive to a probe of interest is also executed, according to preferred embodiments of the invention, via automated technology.

The different structural characteristics of every single complex carbohydrate of a specific library dictates a multitude of unique synthesis protocols. As such, the libraries described by the present invention are preferably generated by a parallel synthesis method, wherein consideration is preferably given to ensure a minimal number of steps executed. Consider, for example, a robotics system permitting parallel addressable distribution of reagents from reagent containers. In this case, a minimal number of steps implies that each of the reagent containers is detailed a minimal number of times. Thus, consideration is given to a sequence of synthesis steps that will ensure completion of the synthesis of all of the complex carbohydrates of the library with a minimal number of times each reagent container is detailed. A dedicated algorithm can be readily developed by one ordinarily skilled in the art to design automated library synthesis protocol which will comply with the above requirements. In fact, a similar algorithm has already been developed for the parallel addressable synthesis of oligonucleotides (Pease, 1994) and peptides (Fodor, 1991) on microchips, both are incorporated by reference as if fully set forth herein).

Technologies enabling automated high-throughput parallel addressable synthesis have developed immensely in the past few years. Automated synthesizers that can control and perform many different solid phase synthesis protocols at the same time are commonly available nowadays (Rivero, 1997). These technologies can be classified according to the type of solid phase substrate that is utilized for the synthesis, the means of the introduction and removal of reagents, and the design of the reaction chambers.

Technologies enabling automated high-throughput solid phase parallel synthesis can be used in accordance with the present invention. Such technologies include, for example, (i) opened reactor systems (e.g., conventional microtiterplates); (ii) closed reactor systems or semi-closed reactor systems (e.g., lab-on-chip); (iii) reaction block systems; (iv) synthesis on polymeric pins; (v) synthesis on polymeric sheets; and (vi) synthesis on a microchip. For a comprehensive review of these technologies and systems see Cargil, 1997, which is incorporated by reference as if fully set forth herein.

Solid phase support: The libraries according to the present invention are preferably synthesized on a solid phase support. As such, the first building block is provided with a suitable functional group for binding such a support. Suitable binding groups include hydroxyls, carbonyl, carboxyl, amines, halides, thiols, esters, boronates, siloxy, aza, oxo, oxiren, or any unsaturated group.

Several solid matrix supports are most suitable for generating carbohydrate libraries according to the present invention, such as, but not limited to, polysterene cross-linked with divinylbenzene (Merrifield, 1963), polyethylene glycol-polystyrene block copolymer (PEG-PS, Bayer, 1991), polyamides (Dryland, 1986), polyacrylamide (Ashardy, 1979), polymethacrylamide (Hsiau, 1997) and cellulose (Frank, 1988). Microfabricated silicon-based arrays produced by standard semi-conductor processing techniques (Fodor, 1991; Sosnowski, 1997; Cheng, 1998, U.S. Pat. Nos. 5,643,738; 5,681,484; and 5,585,069) may also serve as a solid phase support.

Linking the first saccharide building block to the solid phase support: The first saccharide building block is preferably covalently attached to the solid phase matrix via a single atom (e.g., the solid phase functional group) or a linker. The general properties of a linker include: having bi-functional groups enabling attachment to both the solid support and to the initial building block, and as such to define a structure (Atherton, 1989). In a preferred embodiment, the linker is designed cleavable, so as to allow removal of the synthesized oligosaccharide from the matrix post synthesis. This allows for analysis thereof using, for example, mass spectroscopy or any other suitable method. Since enzyme accessibility to the immobilized saccharides is of great importance, the linker length and flexibility are crucial for high yield. As such, linkers suitable for synthesis according to the present invention can include, for example, amino acids, peptides, non-glycosylated proteins, lipids, lipid A, ceramides, dolicol phosphates, cyclodextrins, oligosaccharides, monosaccharides, alkyl chains, nucleic acids, or other spacer molecules. These linkers can be cleavable or non-cleavable and be composed of simple, complex, cyclic or branched entities.

Figure 5A:
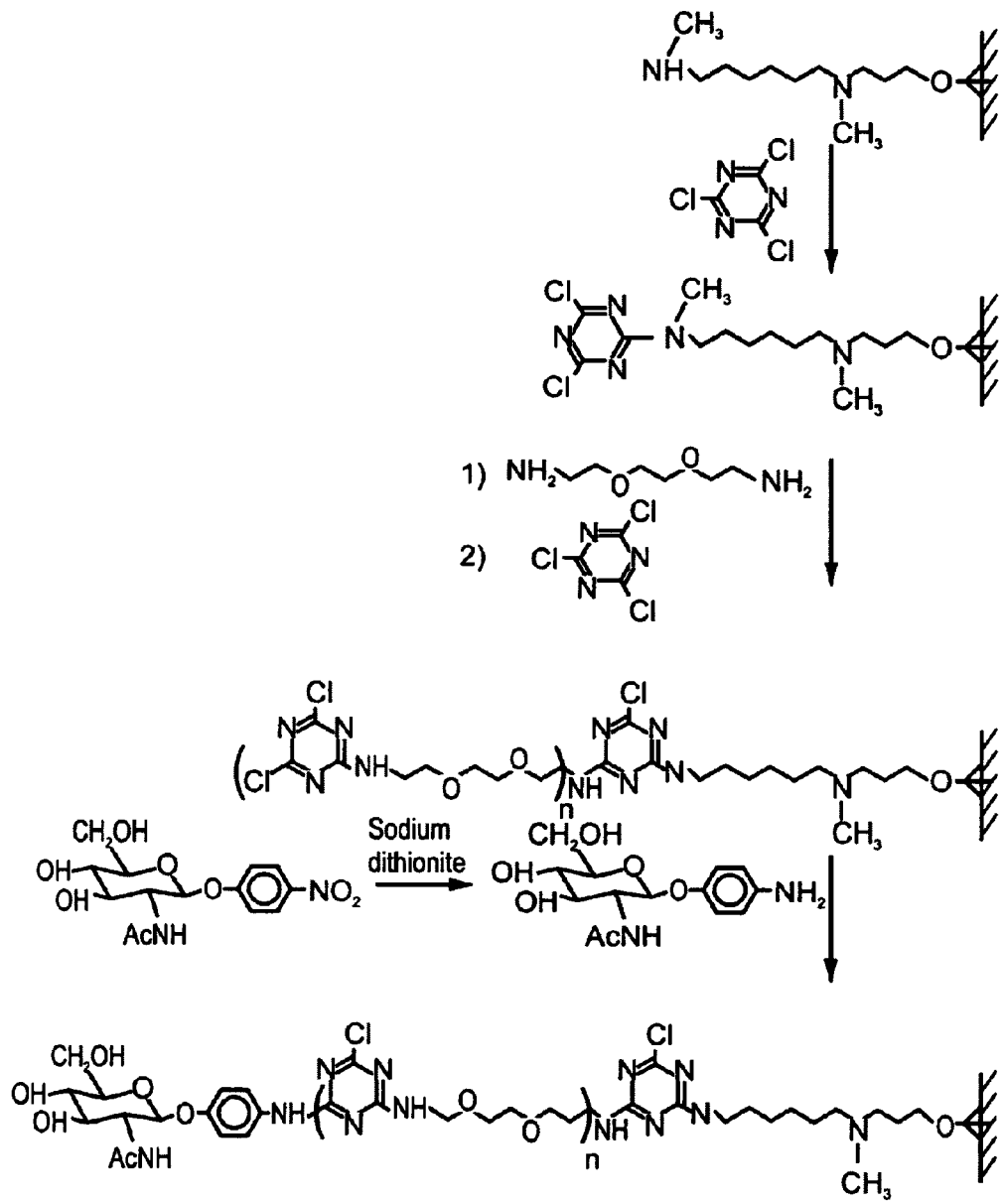
FIG. 5a depicts the synthesis and elongation cycles of a cleavable linker that enables covalent immobilization of a p-Nitrophenyl or amine derivative of a sugar (for example, p-Nitrophenyl-β-D-GlcNAc) to a Covalink NH microtiterplate, which immobilization constitutes a first step in the synthesis of a complex carbohydrate library according to the teachings of the present invention.
Figure 5B:
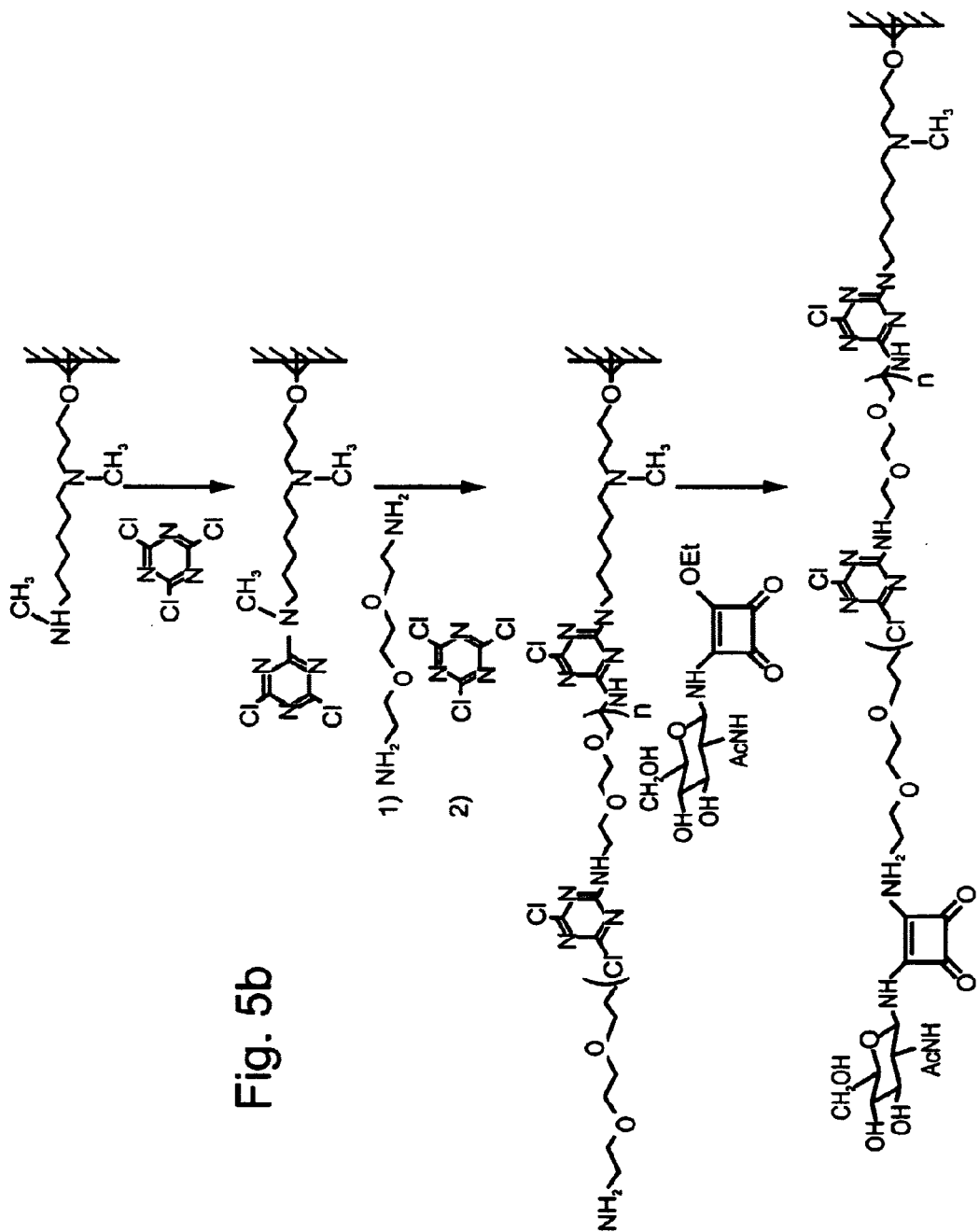
FIG. 5b depicts the synthesis and elongation cycles of a cleavable linker that enables covalent immobilization of a Squaric acid derivative of a sugar (for example, Squaric-β-D-GlcNAc) to a Covalink NH microtiterplate, which immobilization constitutes a first step in synthesis of a complex carbohydrate library according to the teachings of the present invention.

According to presently preferred embodiments of the present invention the linker is between 3.5 nm and 8 nm in length. It is preferably selected sufficiently hydrophilic so as to stay in solution and to avoid none specific interaction with proteins. It is synthesized by elongation cycles using bi-functional building blocks molecules that can form bonds between each other. The starting point can be any functional group which is attached or attachable to the solid support that can react with a bi-functional building block. Because the linker can be ended by any one of the bi-functional building blocks, there are, as shown in FIGS. 5a and 5b, two possible ways to connect the first monosaccharide to the linker. The linker is preferably selected cleavable under mild conditions that do not damage carbohydrates.

Presently preferred cleavable linkers which comply with all of the above preferred criteria are constructed as described under Example 11 and shown in FIGS. 5a and 5b.

Library arrangement: The preferred arrangement of the library constituents according to the present invention is in an array synthesized on a solid phase support in various geometric forms and layouts, such as: two dimensional arrays, multi layer arrays, three dimensional arrays (e.g., stacked microtiters), and arrays which are displayed on spherical disks or cone shapes. Alternatively, the library constituents can be attached to polymer beads in reaction chambers (opened or closed) and arrayed on a two dimensional or a three dimensional support. Any arrangement that enables easy automatic addressable operation of the EMs collection may be used in accordance with the present invention. Attention is preferably given to the spatial distribution of complex carbohydrates of a library to ensure shortest distances among most similar carbohydrates, so as to ensure efficiency of the automated synthesis process. Microfluid systems can and are preferably employed (U.S. Pat. Nos. 5,643,738; 5,681,484; and 5,585,069).

Automated library screening: There are numerous screening technologies and procedures currently employed in the art that can be applied to screen the complex carbohydrate libraries of the present invention. For reviews see Broach, 1996 and Burbaum, 1997, which are incorporated by reference as if fully set forth herein. As such, technologies suitable for high-throughput screening of binding or bioactivities can be based on the following: (i) radioactive detection methods; (ii) fluorescence detection methods; (iii) ELISA based detection methods; and (iv) cell-based assay systems via reporter genes.

Radiolabeled probes that bind to complex carbohydrates of a given library can be detected, for example, by a Scintillation Proximity Assay (SPA, Cook, 1996). The main advantages to SPA are that (i) it does not require removal of free radiolabeled molecules; and (ii) it is readily automated. Additional methods, such as, fluorescence can also be employed either via direct fluorescence detection of a fluorescently labeled bound molecule or, for example, by either the Homogenous Time-Resolved Fluorescence (HTRF, Mathis, 1995) or the Fluorescence Polarization Assay (PFA) technologies (Checovich, 1995). The main advantages of these latter technologies lie in the ability to use "mix and measure" protocols without the addition of further complicating steps. In addition, many variations of the Enzyme-Linked Immunosorbent Assays (ELISA) detection method can also be employed with accordance to this invention.

The bioactivity and binding capabilities of each of the complex carbohydrates of a library according to the present invention can be evaluated by using cell-based assay systems. Cell-based assay systems for high-throughput screening have been extensively studied, and guidelines for selecting appropriate screening systems have been introduced (Rose, 1996). Assay systems using mammalians and insect cells, as well as yeast and bacterial cells, have been thoroughly described (Broach, 1996; Rose, 1996; Suto, 1997).

One of the most common methods for detecting interactions between molecules expressed in cells and ligands capable of binding such cells is to employ a reporter gene. This involves splicing the transcriptional control elements of a target gene with a coding sequence of a reporter gene into a vector and introducing the vector into a suitable cell line in order to establish a detection system that responds to modulation of the target, in this case by an addressable library derived complex carbohydrate. Common examples of reporter genes are enzymes such as alkaline phosphatase, chloramphenicol acetyltransferase, firefly and bacterial luciferases, and β-galactosidase. Low levels of activity for these enzymes can be detected using colorimetric, chemiluminescent or bioluminescent detection methods. Non enzymatic reporter genes such as green, red shifted and blue fluorescent protein (Phillips, 1997) can be employed as well.

Thus, according to one aspect of the present invention there is provided a combinatorial complex carbohydrate library. The combinatorial complex carbohydrate library according to the present invention includes a plurality of addressable complex carbohydrate structures.

According to another aspect of the present invention there is provided a method of producing an addressable combinatorial complex carbohydrate library. The method according to this aspect of the present invention is effected by enzymatically synthesizing a plurality of complex carbohydrate structures, each of which is attached to at least one addressed location of a plurality of locations of a solid support, resulting in an addressable combinatorial complex carbohydrate library.

As used herein in the specification and in the claims section below the terms "addressable" and "addressed" refer to both location and identity. Thus, the location and identity (composition) of a complex carbohydrate structure of a library according to the present invention are both known in advance and that carbohydrate structure is therefore addressable. It is understood that the phrase "a complex carbohydrate structure" refers to a plurality of complex carbohydrate molecules all having the same structure and localized at a specific and addressable location on the solid support.

The addressable complex carbohydrate structures of a library according to the present invention are preferably attached to the solid support via a linker (spacer). The linker according to preferred embodiments of the invention includes at least two contiguous covalent bonds and it is of a length of at least 20 Angstroms. Suitable linkers include, but are not limited to, an amino acid, a peptide, a non-glycosylated protein, a lipid, a ceramide, dolicol phosphate, a cyclodextrin, an oligosaccharide, a monosaccharide, an alkyl chain, and a nucleic acid (e.g., an oligonucleotide).

The solid support onto which complex carbohydrate structures of a library according to the present invention are attached can include addressable microparticles or beads, or a flat platform. The addressable microparticles or beads are arranged, for example, within wells of a microtiter plate. Alternatively, a microtiterplate, a membrane or a chip (e.g., silicone chip) serve as the flat platform solid support according to the present invention.

According to a presently preferred embodiment of the invention the solid support is a chip and different complex carbohydrate structures of the plurality of addressable complex carbohydrate structures are formed in patches spaced not more than 2.25 mm from one another (center to center) over the surface of the chip, thereby providing a density of at least 20 different addressable complex carbohydrate structures per square centimeter.

The substance of which the solid support is made can be, for example, polysterene cross-linked with divinylbenzene, polyethylene glycol-polystyrene block copolymer, polyamides, polyacrylamide, polymethacrylamide, cellulose, glass, quartz, plastic or silica.

According to a preferred embodiment of the present invention at least one, preferably at least three, more preferably at least ten, more preferably, at least 100, more preferably at least 1000 of the plurality of addressable complex carbohydrate structures of a library of the present invention includes at least two, three, four or at least five or more contiguous saccharide units of a single species. As further detailed hereinabove and resolved such a structure is not trivial due to uncontrolled polymerization.

According to another preferred embodiment of the present invention at least one, preferably at least three, more preferably at least ten, more preferably, at least 100, more preferably at least 1000 of the plurality of addressable complex carbohydrate structures of a library of the present invention includes at least one, two, three, four or at least five or more branches.

According to yet another preferred embodiment of the present invention at least one, two, three or at least four of the branches are formed of identical core and branching saccharide units. As further detailed hereinabove and resolved such a structure is not trivial especially if the antennas attached to each of the branches differ in saccharide units composition.

According to still further features in the described preferred embodiments at least one, preferably at least three, more preferably at least ten, more preferably, at leas 100, more preferably at least 1000, of the plurality of addressable complex carbohydrate structures includes at least 4 preferably at least 5, more preferably at least 7, more preferably at least 9, more preferably at least 10, more preferably at least 12, more preferably at least 15, 20, 25 or at least 30, more preferably at least 50 or more saccharide units.

Depending on its intended use, as further detailed hereinunder, the plurality of addressable complex carbohydrate structures of a library according to the present invention can be a representation including non-natural or natural complex carbohydrates, e.g., which are derived from a human source, such as tissue, cells or body fluids of a human-being. Alternatively, the plurality of addressable complex carbohydrate structures can be a representation of domains (fragments) of at least one natural complex carbohydrate. Such a library, as further detailed herein, can be employed to identify an active site of the natural complex carbohydrate.

According to yet another aspect of the present invention there is provided a method of identifying a complex carbohydrate capable of binding an entity. The method according to this aspect of the present invention is effected by providing an addressable combinatorial complex carbohydrate library according to any of the embodiments herein described and screening the addressable combinatorial complex carbohydrate library with the entity for identifying the complex carbohydrate capable of binding the entity.

As further exemplified hereinunder, any entity can be used to screen an addressable combinatorial complex carbohydrate library according to the present invention. For example, the entity can be a candidate for a biologically active material, such as a drug candidate derived from a natural or synthetic origin. In this case the method according to this aspect of the invention serves for identifying a complex carbohydrate which is a target for the candidate for the biologically active material. Alternatively, the entity can be a ligand known to bind a specific natural complex carbohydrate. In this case, the addressable combinatorial complex carbohydrate library can be a representation of domains of the specific natural complex carbohydrate, whereas the method serves in this case for identifying a specific domain of the domains which binds the ligand to thereby identify the active site of the natural complex carbohydrate.

According to still another aspect of the present invention there is provided a method of diagnosing a disorder characterized by self or non-self complex carbohydrate structures and elicitation of antibodies there against. The method according to this aspect of the present invention is effected by providing an addressable combinatorial complex carbohydrate library representing the self and/or the non-self complex carbohydrates by employing any of the methods described herein for synthesizing such a library. The addressable combinatorial complex carbohydrate library is thereafter reacted with antibodies derived from a patient suspected of having the disorder to thereby generate a pattern of the locations to which the antibodies bind, such that by comparing that pattern with a known pattern characterizing a healthy individual, a diagnosis of the disorder is obtainable.

Disorders known to be associated with production or introduction of self and/or non-self complex carbohydrate structures include, but are not limited to, tumorogenesis, metastasis, pregnancy, vascular disease, heart disease, neurodegenerative disease, autoimmune disease and organ transplantation. Neurodegenerative diseases include, but are not limited to, Parkinson's disease, Alzheimer's disease, basal ganglia degenerative diseases, motoneuron diseases, Scrapie, spongyform encephalopathy and Creutzfeldt-Jakob's disease, infertility, allergies, embryogenesis, apoptosis and neurodegenerative disorders.

Outlined below are some strategies employed while screening specific libraries generated by the method according to the present invention.

Thus, in order to identify complex carbohydrate receptors, associated proteins, lectins and/or drug targets, an enzymatically combinatorial complex carbohydrates array composed of known complex carbohydrate structures from human cells or novel carbohydrate structures generated from reduction mapping is screened against a variety of labeled probes from sources such as, labeled human tissue homogenates, labeled receptors, labeled proteins encoded by EST collections, labeled recombinant proteins, phage display libraries, labeled cells from either human tissues, pathogens or solutions containing mixtures of labeled protein molecules from human tissue sources or from pathogenic cells. The objective of such screening is to identify the labeled molecules from the above mentioned sources which bind specifically to a complex carbohydrate of the library. Following isolation and characterization, these molecules can be tested further as potential candidates for drug therapy or targets for drug therapy. These strategies can also be employed to identify new receptors, lectins or any proteins or molecules that binds to specific complex carbohydrate constituents of the library.

To identify lead compounds which bind a specific complex carbohydrate, an enzymatic combinatorial complex carbohydrate library composed of known complex carbohydrate structures of human cells or novel carbohydrate structures generated from reduction mapping of normal and/or pathogenized cells or pathogens are screened against a diverse group of labeled molecules. The objective of this screening is to gain a clearer understanding of the specific interactions between the complex carbohydrate found in or on these cells and the respective ligand thereof. The isolated and characterized ligands can then be utilized as modulators of important biological activities, such as cell-to-cell communication, cell recognition, cell development and tumor cell metastasis.

For the identification of novel bio-active complex carbohydrates, a complex carbohydrate library, according to the present invention, is prepared composed of a diverse array of complex carbohydrate structures, including such structures not normally found in nature. This complex carbohydrate library is then screened against cell-based assay systems, or against defined human or microbial labeled target molecules, such as lectins or receptors. Such screening leads to the identification of new complex carbohydrate based drug candidates. Alternatively, such screening leads to the identification of a disease associated complex carbohydrate. Such disease associated complex carbohydrate can be used to elicit antibodies thereto, the antibodies can thereafter be used to identify and isolate a glycoprotein harboring the disease associated carbohydrate, to thereby identify new protein and genes associated with that disease.

To identify an active site of a known or novel complex carbohydrate, a library according to the present invention is prepared composed of all the possible domain fragments of this particular complex carbohydrate. As such, these domain fragments can then be screened with a labeled receptor which normally binds the complex carbohydrate including such domains. The binding specificity to each of the domain fragments can then be assessed to enable the isolation of the domain fragment of a particular complex carbohydrate responsible for the binding activity, i.e., the active site. This objective can be performed in parallel for a number of well characterized complex carbohydrate—receptor pairs.

The present invention also enables mapping of antibodies against self or non-self glyco-markers found in the blood serum of a patient. As such, a complex carbohydrate library according to the present invention is synthesized to include a diverse array of glyco markers present in the blood serum of a patient. This library is then screened against labeled pools of serum antibodies from this patient and a resulting generated antibody profile can be implemented as a pre-diagnostic tool for cancer and organ transplantation compatibility.

Specific arrays of glyco-antigens can also be used for the identification of new glyco-markers related to cancer, cardiovascular diseases or organ transplantation. Such glyco-antigen arrays are screened according to the present invention against labeled serum antibodies from a diverse population. The antibody profile of a diseased individual can then be compared with the profile of the healthy population. This comparison produces a unique profile of antibodies associated with the immune response to a disease state and as such, a particular complex carbohydrate reacting with an antibody of the unique profile turns into a diagnostic marker for that particular disease.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

The following examples detail the structure of complex carbohydrates synthesized using a collection of specifically selected enzymes. Generally, the nomenclature used herein and the laboratory procedures in biochemistry described below are those well known and commonly employed in the art. As such, it will be appreciated that the following synthesis procedures could be practiced with ease by one ordinarily skilled in the art.

In view of the findings that sugar residues of glycoproteins play an important role in the control of cellular function and cellular recognition, investigation of carbohydrate function in pathological states has led to the assignment of some complex carbohydrates as tumor specific markers (Orntoft, 1995). Dramatic changes in glycosylation of proteins occur in almost every carcinoma (Hakomori, 1989), which often reflects changes in the biosynthesis pathways.

For example, blocking the glycosylation biosynthesis pathway leads to an overproduction of structures which are typically found in small amounts in normal cells. Furthermore, alterations in glycosylation pathways can lead to the utilization of alternate pathways which, in turn, lead to the formation of new complex carbohydrate structures not normally present in or on cells. Such regulation of glycosylation pathways in the cell can often be attributed to glycosyltransferase activities.

The altered carbohydrate structures of glycoproteins of various tumor tissues are considered to be the basis for abnormal behavior of tumor cells, which behavior includes metastasis and invasion of the tumor cells into healthy tissues (Kobata, 1998).

Tumor markers are significant for the diagnosis and treatment of malignant cells. Potential markers can be any specific epitopes presented by the tumor cells, such as, peptides, glycopeptides, glycolipids or any combinations thereof. These unique epitopes can be specifically identified by monoclonal antibodies and as such unique glycosylation patterns were and are intensively investigated as potential tumor markers for cancer immunotherapy and diagnostics (Ronin, 1998).

The present invention enables to use tumor markers not only for immunotherapy or diagnostics but also as potential targets for drug therapy. To this end, a combinatorial array including both Tumor Specific Complex Carbohydrates (TSCC) and normal carbohydrate structures would enable isolation of new drug candidates by identifying molecules that bind specifically and uniquely to complex carbohydrate structures associated with a tumorous conditions.

Example 1

Lung cancer is a disease of almost epidemic proportion. Approximately 157,000 new cases causing 142,000 deaths were recorded in 1990 (Faber, 1991). Squamous Lung Carcinoma (SLC) which is of the Non-Small Cell Lung Cancer (NSCLC) type, accounts for approximately 35% of all lung cancers. It is closely correlated with smoking and diagnosed most frequently in males. Squamous carcinoma originates in the central or hilar region of the lung and may cavitate when found in a peripheral location. It is classified as a severe and malignant form of cancer. Although poorly differentiated, SLC displays unique complex carbohydrate antigens associated with both membrane bound glycoproteins and mucine-like molecules which are released into circulatory system and serve as serum markers (Martensson, 1988).

The following tables describe the components and enzyme modules (EMs) necessary for the synthesis of a complex carbohydrate library for screening and isolation of chemical compounds, proteins or other molecules which specifically bind SLC markers. Such molecules may serve as potential new drug candidates or drugs useful for the prevention of squamous lung cancer metastasis.

Tables 9–10 present complex carbohydrates of abnormal structures of SLC carbohydrate chains released into the circulatory system (marked A1, A2, A3, A8, A9 and A10), all the possible fragments derived from such SLC carbohydrate chains (associated with A1, A2, A3, A8, A9 and A10 by a1, a2, a3, a8, a8 and a10, respectively), normal blood antigens (marked A4, A5, A6, A7, A11 and A12) and all possible normal blood antigen fragments derived therefrom (associated with A4, A5, A6, A7, A11 and A12 by a4, a5, a6, a7, a11 and a12, respectively).

TABLE 9

| Source | Carbohydrates | EM |
|---|---|---|
| A1 SLC | β-D-Galp-(1→4)—⎤<br>                      β-D-GlcpNAc-(1→6)—⎤<br>α-L-Fucp-(1→3)——⎦         β-D-Galp-(1→4)-D-Glc<br>β-D-Galp-(1→3)-β-D-GlcpNAc-(1→3)——⎦ | 1 |
| A2 SLC | β-D-Galp-(1→4)—⎤<br>             β-D-GlcpNAc-(1→6)—⎤<br>α-L-Fucp-(1→3)——⎦<br>                              β-D-Galp-(1→4)-D-Glc<br>α-L-Fucp-(1→4)—⎤<br>             β-D-GlcpNAc-(1→3)——⎦<br>β-D-Galp-(1→3)——⎦ | 2 |
| A3 SLC | α-L-Fucp-(1→4)—⎤<br>         β-D-GlcpNAc-(1→3)-β-D-Galp-(1→4)—⎤<br>β-D-Galp-(1→3)——⎦                     β-D-GlcpNAc-(1→6)—⎤<br>                          α-L-Fucp-(1→3)——⎦      β-D-Galp-(1→4)-D-Glc<br>                        β-D-Galp-(1→3)-β-D-GlcpNAc-(1→3)——⎦ | 3 |
| A4 Normal blood HI antigen | α-L-Fucp-(1→2)-β-D-Galp-(1→3)-β-D-GlcpNAc-(1→3)-β-D-Galp-(1→4)-β-D-Glcp-(1→1)-Ceramide | 4 |
| A5 Normal blood HII antigen | α-L-Fucp-(1→2)-β-D-Galp-(1→4)-β-D-GlcpNAc-(1→3)-β-D-Galp-(1→4)-β-D-Glcp-(1→1)-Ceramide | 5 |
| A6;a7 Normal Lewis a antigen | α-L-Fucp-(1→4)—⎤<br>         β-D-GlcpNAc-(1→3)-β-D-Galp-(1→4)-β-D-Glcp-(1→1)-Ceramide<br>β-D-Galp-(1→3)——⎦ | 6 |
| A7 Normal Lewis b antigen | α-L-Fucp-(1→4)—⎤<br>                β-D-GlcpNAc-(1→3)-β-D-Galp-(1→4)-β-D-Glcp-(1→1)-Ceramide<br>α-L-Fucp-(1→2)-β-D-Galp-(1→3)——⎦ | 7 |

TABLE 9-continued

| Source | Carbohydrates | EM |
|---|---|---|
| A8 SLC | α-L-Fucp-(1→4)—┐<br>               β-D-GlcpNAc-(1→3)-β-D-Galp-(1→4)—┐<br>β-D-Galp-(1→3)—┘                             D-Glc<br>                         α-L-Fucp-(1→3)—┘ | 8 |
| A9 SLC | β-D-Galp-(1→3)-β-D-GlcpNAc-(1→3)-β-D-Galp-(1→4)—┐<br>                                          β-D-GlcpNAc-(1→3)-β-D-Galp-(1→4)-D-Glc<br>                      α-L-Fucp-(1→3)—┘ | 9 |
| A10 SLC | α-L-Fucp-(1→4)—┐<br>               β-D-GlcpNAc-(1→3)-β-D-Galp-(1→4)—┐<br>β-D-Galp-(1→3)—┘                  β-D-GlcpNAc-(1→3)-β-D-Galp-(1→4)-D-Glc<br>                      α-L-Fucp-(1→3)—┘ | 10 |
| A11 Normal Lewis x antigen | β-D-Galp-(1→4)—┐<br>              β-D-GlcpNAc-(1→3)-β-D-Galp-(1→4)-β-D-Glcp-(1→1)-Ceramide<br>α-L-Fucp-(1→3)—┘ | 11 |
| A12 Normal Lewis x antigen | α-L-Fucp-(1→2)-β-D-Galp-(1→4)—┐<br>                              β-D-GlcpNAc-(1→3)-β-D-Galp-(1→4)-β-D-Glcp-(1→1)-Ceramide<br>              α-L-Fucp-(1→3)—┘ | 12 |

TABLE 10

| Source | Carbohydrates sub fragments | EM |
|---|---|---|
| a1;a2;a3;a8;a9;a10 | β-D-Galp-(1→4)-D-Glc | 13 |
| a8 | α-L-Fucp-(1→3)-D-Glc | 14 |
| a1;a2;a3;a4;a6;a7;a8;a9;a10 | β-D-Galp-(1→3)-β-D-GlcpNAc-(1→ | 15 |
| a1;a2;a3;a9;a10 | β-D-Galp-(1→4)-β-D-GlcpNAc-(1→ | 16 |
| a1;a2;a3 | β-D-GlcpNAc-(1→6)-β-D-Galp-(1→ | 17 |
| a1;a2;a3;a4;a5;a6;<br>a7;a8;a9;a10;a11;a12 | β-D-GlcpNAc-(1→3)-β-D-Galp-(1→ | 18 |
| a4;a5;a7 | α-L-Fucp-(1→2)-β-D-Galp-(1→ | 19 |
| a2;a3;a6;a7;a8;a10 | α-L-Fucp-(1→4)-β-D-GlcpNAc-(1→ | 20 |
| a1;a2;a3;a9;a10;a11;a12 | α-L-Fucp-(1→3)-β-D-GlcpNAc-(1→ | 21 |
| a1;a2;a3 | β-D-GlcpNAc-(1→6)-β-D-Galp-(1→4)-D-Glc | 22 |
| a1;a2;a3;a9;a10 | β-D-GlcpNAc-(1→3)-β-D-Galp-(1→4)-D-Glc | 23 |
| a1;a2;a3;a4;a6;a7;a8;a9;a10 | β-D-Galp-(1→3)-β-D-GlcpNAc-(1→3)-β-D-Galp-(1→ | 24 |
| a1;a2;a3 | β-D-Galp-(1→4)-β-D-GlcpNAc-(1→6)-β-D-Galp-(1→ | 25 |
| 5;a9;a10;a11;a12 | β-D-Galp-(1→4)-β-D-GlcpNAc-(1→3)-β-D-Galp-(1→ | 26 |
| a1;a2;a3 | α-L-Fucp-(1→3)-β-D-GlcpNAc-(1→6)-β-D-Galp-(1→ | 27 |
| a2;a3;a6;a7;a8 | α-L-Fucp-(1→4)-β-D-GlcpNAc-(1→3)-β-D-Galp-(1→ | 28 |
| a4;a7 | α-L-Fucp-(1→2)-β-D-Galp-(1→3)-β-D-GlcpNAc-(1→ | 29 |
| a5 | α-L-Fucp-(1→2)-β-D-Galp-(1→4)-β-D-GlcpNAc-(1→ | 30 |
| a9;a10;a11;a12 | α-L-Fucp-(1→3)-β-D-GlcpNAc-(1→3)-β-D-Galp-(1→ | 31 |
| a9;a10 | α-L-Fucp-(1→3)-β-D-GlcpNAc-(1→3)-β-D-Galp-(1→4)-D-Glc | 32 |
| a2 | α-L-Fucp-(1→4)-β-D-GlcpNAc-(1→3)-β-D-Galp-(1→4)-D-Glc | 33 |
| a1;a2;a3; | α-L-Fucp-(1→3)-β-D-GlcpNAc-(1→6)-β-D-Galp-(1→4)-D-Glc | 34 |
| a9;a10 | α-D-Galp-(1→4)-β-D-GlcpNAc-(1→3)-β-D-Galp-(1→4)-D-Glc | 35 |
| a1;a2;a3 | α-D-Galp-(1→4)-β-D-GlcpNAc-(1→6)-β-D-Galp-(1→4)-D-Glc | 36 |
| a1;a2;a3;a8 | α-D-Galp-(1→3)-β-D-GlcpNAc-(1→3)-β-D-Galp-(1→4)-D-Glc | 37 |
| a4;a7 | α-L-Fucp-(1→2)-β-D-Galp-(1→3)-β-D-GlcpNAc-(1→3)-β-D-Galp-(1→ | 38 |
| a5;a12 | α-L-Fucp-(1→2)-β-D-Galp-(1→4)-β-D-GlcpNAc-(1→3)-β-D-Galp-(1→ | 39 |
| a9;a10 | β-D-GlcpNAc-(1→3)-β-D-Galp-(1→4)-β-D-GlcpNAc-(1→3)-β-D-Galp-(1→ | 40 |
| a9;a10 | β-D-GlcpNAc-(1→3)-β-D-Galp-(1→4)-β-D-GlcpNAc-(1→3)-β-D-Galp-(1→4)-D-Glc | 41 |
| a3 | β-D-GlcpNAc-(1→3)-β-D-Galp-(1→4)-β-D-GlcpNAc-(1→6)-β-D-Galp-(1→4)-D-Glc | 42 |
| a3 | α-L-Fucp-(1→4)-β-D-GlcpNAc-(1→3)-β-D-Galp-(1→4)-β-D-GlcpNAc-(1→6)-β-D-Galp-(1→ | 43 |
| a3 | β-D-Galp-(1→3)-β-D-GlcpNAc-(1→3)-β-D-Galp-(1→4)-β-D-GlcpNAc-(1→6)-β-D-Galp-(1→ | 44 |
| a9,a10 | β-D-Galp-(1→3)-β-D-GlcpNAc-(1→3)-β-D-Galp-(1→4)-β-D-GlcpNAc-(1→3)-β-D-Galp-(1→ | 45 |

TABLE 10-continued

| Source | Carbohydrates sub fragments | EM |
| --- | --- | --- |
| a3 | β-D-Galp-(1→3)-β-D-GlcpNAc-(1→3)-β-D-Galp-(1→4)-β-D-GlcpNAc-(1→6)-β-D-Galp-(1→4)-D-Glc | 46 |
| a10 | *see below | 47 |
| a3 | α-L-Fucp-(1→4)-β-D-GlcpNAc-(1→3)-β-D-Galp-(1→4)-β-D-GlcpNAc-(1→6)-β-D-Galp-(1→4)-D-Glc | 48 |
| a9 | β-D-Galp-(1→3)-β-D-GlcpNAc-(1→3)-β-D-Galp-(1→4)-β-D-GlcpNAc-(1→3)-β-D-Galp-(1→4)-D-Glc | 49 |
| a8 | β-D-Galp-(1→4)—┐<br>　　　　　　　D-Glc<br>α-L-Fucp-(1→3)—┘ | 50 |
| a1;a2;a3;9;a10;a11;a12 | β-D-Galp-(1→4)—┐<br>　　　　　　　β-D-GlcpNAc-(1→<br>α-L-Fucp-(1→3)—┘ | 51 |
| a1;a2;a3 | β-D-GlcpNAc-(1→6)—┐<br>　　　　　　　β-D-Galp-(1→<br>β-D-GlcpNAc-(1→3)—┘ | 52 |
| a2;a6;a7;a8;a10 | α-L-Fucp-(1→4)—┐<br>　　　　　　　β-D-GlcpNAc-(1→<br>β-D-Galp-(1→3)—┘ | 53 |
| a2 | β-D-GlcpNAc-(1→6)—┐<br>　　　　　　　β-D-Galp-(1→<br>α-L-Fucp-(1→4)-β-D-GlcpNAc-(1→3)—┘ | 54 |
| 9;a10;a11;a12 | β-D-Galp-(1→4)—┐<br>　　　　　　　β-D-GlcpNAc-(1→3)-β-D-Galp-(1→<br>α-L-Fucp-(1→3)—┘ | 55 |
| a12 | α-L-Fucp-(1→2)-β-D-Galp-(1→4)—┐<br>　　　　　　　β-D-GlcpNAc-(1→<br>α-L-Fucp-(1→3)—┘ | 56 |
| a2;a3;a6;a7;a8;a10 | α-L-Fucp-(1→4)—┐<br>　　　　　　　β-D-GlcpNAc-(1→3)-β-D-Galp-(1→<br>β-D-Galp-(1→3)—┘ | 57 |
| a7 | α-L-Fucp-(1→4)—┐<br>　　　　　　　β-D-GlcpNAc-(1→<br>α-L-Fucp-(1→2)-β-D-Galp-(1→3)—┘ | 58 |
| a3;a9;a10 | β-D-GlcpNAc-(1→3)-b-D-Galp-(1→4)—┐<br>　　　　　　　β-D-GlcpNAc-(1→<br>α-L-Fucp-(1→3)—┘ | 59 |
| a1;a2;a3 | β-D-GlcpNAc-(1→6)—┐<br>　　　　　　　β-D-Galp-(1→4)-D-Glc<br>β-D-GlcpNAc-(1→3)—┘ | 60 |

TABLE 10-continued

| Source | Carbohydrates sub fragments | EM |
|---|---|---|
| a1;a2;a3 | α-L-Fucp-(1→3)-β-D-GlcpNAc-(1→6)⎤<br>　　　　　　　　　　　　　　β-D-Galp-(1→<br>β-D-GlcpNAc-(1→3)⎦ | 61 |
| a1;a2;a3 | β-D-Galp-(1→4)⎤<br>　　　　β-D-GlcpNAc-(1→6)-β-D-Galp-(1→<br>α-L-Fucp-(1→3)⎦ | 62 |
| a1;a2;a3 | β-D-GlcpNAc-(1→6)⎤<br>　　　　　　　　β-D-Galp-(1→<br>β-D-Galp-(1→3)-β-D-GlcpNAc-(1→3)⎦ | 63 |
| a1;a2;a3 | β-D-Galp-(1→4)⎤<br>　　　　β-D-GlcpNAc-(1→6)-β-D-Galp-(1→<br>α-L-Fucp-(1→3)⎦ | 64 |
| a1;a2;a3 | β-D-GlcpNAc-(1→6)⎤<br>　　　　　　　　β-D-Galp-(1→4)-D-Glc<br>β-D-Galp-(1→3)-β-D-GlcpNAc-(1→3)⎦ | 65 |
| a1;a2;a3 | β-D-Galp-(1→4)⎤<br>　　　　β-D-GlcpNAc-(1→6)-β-D-Galp-(1→4)-D-Glc<br>α-L-Fucp-(1→3)⎦ | 66 |
| a1;a2;a3 | α-L-Fucp-(1→3)–β-D-GlcpNAc-(1→6)⎤<br>　　　　　　　　　　　　　　β-D-Galp-(1→4)-D-Glc<br>β-D-GlcpNAc-(1→3)⎦ | 67 |
| a1;a2;a3 | β-D-Galp-(1→4)-β-D-GlcpNAc-(1→6)⎤<br>　　　　　　　　　　　　　　β-D-Galp-(1→4)-D-Glc<br>β-D-GlcpNAc-(1→3)⎦ | 68 |
| a1;a2;a3 | α-L-Fucp-(1→3)-β-D-GlcpNAc-(1→6)⎤<br>　　　　　　　　　　　　　　β-D-Galp-(1→<br>β-D-Galp-(1→3)-β-D-GlcpNAc-(1→3)⎦ | 69 |
| a1;a2 | β-D-Galp-(1→4)-β-D-GlcpNAc-(1→6)⎤<br>　　　　　　　　　　　　　　β-D-Galp-(1→<br>β-D-Galp-(1→3)-β-D-GlcpNAc-(1→3)⎦ | 70 |
| a2 | β-D-GlcpNAc-(1→6)⎤<br>　　　　　　　　β-D-Galp-(1→4)-D-Glc<br>α-L-Fucp-(1→4)-β-D-GlcpNAc-(1→3)⎦ | 71 |
| a2;a8;a9 | α-L-Fucp-(1→4)⎤<br>　　　　β-D-GlcpNAc-(1→3)-β-D-Galp-(1→4)-D-Glc<br>β-D-Galp-(1→3)⎦ | 72 |

TABLE 10-continued

| Source | Carbohydrates sub fragments | EM |
|---|---|---|
| a2 | β-D-GlcpNAc-(1→6)—┐<br>α-L-Fucp-(1→4)—┐            β-D-Galp-(1→<br>        β-D-GlcpNAc-(1→3)—┘<br>β-D-Galp-(1→3)—┘ | 73 |
| a2 | β-D-Galp-(1→4)-β-D-GlcpNAc-(1→6)—┐<br>                      β-D-Galp-(1→<br>α-L-Fucp-(1→4)-β-D-GlcpNAc-(1→3)—┘ | 74 |
| a2 | α-L-Fucp-(1→3)-β-D-GlcpNAc-(1→6)—┐<br>                      β-D-Galp-(1→<br>α-L-Fucp-(1→4)-β-D-GlcpNAc-(1→3)—┘ | 75 |
| a8 | β-D-Galp-(1→3)-β-D-GlcpNAc-(1→3)-β-D-Galp-(1→4)—┐<br>                                        D-Glc<br>                     α-L-Fucp-(1→3)—┘ | 76 |
| a8 | α-L-Fucp-(1→4)-β-D-GlcpNAc-(1→3)-β-D-Galp-(1→4)—┐<br>                                        D-Glc<br>                     α-L-Fucp-(1→3)—┘ | 77 |
| a12 | α-L-Fucp-(1→2)-β-D-Galp-(1→4)—┐<br>                      β-D-GlcpNAc-(1→3)-β-D-Galp-(1→<br>          α-L-Fucp-(1→3)—┘ | 78 |
| a9;a10 | β-D-GlcpNAc-(1→3)-β-D-Galp-(1→4)—┐<br>                      β-D-GlcpNAc-(1→3)-β-D-Galp-(1→<br>         α-L-Fucp-(1→3)—┘ | 79 |
| a9;a10 | β-D-Galp-(1→4)—┐<br>         β-D-GlcpNAc-(1→3)-β-D-Galp-(1→4)-D-Glc<br>α-L-Fucp-(1→3)—┘ | 80 |
| a7 | α-L-Fucp-(1→4)—┐<br>          β-D-GlcpNAc-(1→3)-β-D-Galp-(1→<br>α-L-Fucp-(1→2)-β-D-Galp-(1→3)—┘ | 81 |
| a10 | α-L-Fucp-(1→4)—┐<br>          β-D-GlcpNAc-(1→3)-β-D-Galp-(1→4)-β-D-GlcpNAc-(1→<br>β-D-Galp-(1→3)—┘ | 82 |
| a3;a9;a10 | β-D-Galp-(1→3)-β-D-GlcpNAc-(1→3)-β-D-Galp-(1→4)—┐<br>                                        β-D-GlcpNAc-(1→<br>                     α-L-Fucp-(1→3)—┘ | 83 |
| a1;a2;a3 | α-L-Fucp-(1→3)-β-D-GlcpNAc-(1→6)—┐<br>                      β-D-Galp-(1→4)-D-Glc<br>β-D-Galp-(1→3)-β-D-GlcpNAc-(1→3)—┘ | 84 |

TABLE 10-continued

| Source | Carbohydrates sub fragments | EM |
|---|---|---|
| a1;a2;a3 | β-D-Galp-(1→4)-β-D-GlcpNAc-(1→6)—┐<br>　　　　　　　　　　　　　　　β-D-Galp-(1→4)-D-Glc<br>β-D-Galp-(1→3)-β-D-GlcpNAc-(1→3)—┘ | 85 |
| a1;a2;a3 | β-D-Galp-(1→4)—┐<br>　　　　β-D-GlcpNAc-(1→6)—┐<br>α-L-Fucp-(1→3)—┘　　　　β-D-Galp-(1→4)-D-Glc<br>　　　　β-D-GlcpNAc-(1→3)—┘ | 86 |
| a1;a2;a3 | β-D-Galp-(1→4)—┐<br>　　　　β-D-GlcpNAc-(1→6)—┐<br>α-L-Fucp-(1→3)—┘　　　　β-D-Galp-(1→<br>β-D-Galp-(1→3)-β-D-GlcpNAc-(1→3)—┘ | 87 |
| a2 | 　　　　β-D-GlcpNAc-(1→6)—┐<br>α-L-Fucp-(1→4)—┐　　　β-D-Galp-(1→4)-D-Glc<br>　　　　β-D-GlcpNAc-(1→3)—┘<br>β-D-Galp-(1→3)—┘ | 88 |
| a2 | β-D-Galp-(1→4)-β-D-GlcpNAc-(1→6)—┐<br>　　　　　　　　　　　　　　　β-D-Galp-(1→4)-D-Glc<br>α-L-Fucp-(1→4)-β-D-GlcpNAc-(1→3)—┘ | 89 |
| a2 | α-L-Fucp-(1→3)-β-D-GlcpNAc-(1→6)—┐<br>　　　　　　　　　　　　　　　β-D-Galp-(1→4)-D-Glc<br>α-L-Fucp-(1→4)-β-D-GlcpNAc-(1→3)—┘ | 90 |
| a2 | α-L-Fucp-(1→3)-β-D-GlcpNAc-(1→6)—┐<br>α-L-Fucp-(1→4)—┐　　　β-D-Galp-(1→<br>　　　　β-D-GlcpNAc-(1→3)—┘<br>β-D-Galp-(1→3)—┘ | 91 |
| a2 | β-D-Galp-(1→4)-β-D-GlcpNAc-(1→6)—┐<br>α-L-Fucp-(1→4)—┐　　　β-D-Galp-(1→<br>　　　　β-D-GlcpNAc-(1→3)—┘<br>β-D-Galp-(1→3)—┘ | 92 |
| a2 | β-D-Galp-(1→4)—┐<br>　　　　β-D-GlcpNAc-(1→6)—┐<br>α-L-Fucp-(1→3)—┘　　　β-D-Galp-(1→<br>α-L-Fucp-(1→4)-β-D-GlcpNAc-(1→3)—┘ | 93 |
| a3;a10 | α-L-Fucp-(1→4)—┐<br>　　　β-D-GlcpNAc-(1→3)-β-D-Galp-(1→4)—┐<br>β-D-Galp-(1→3)—┘　　　　　　β-D-GlcpNAc-(1→<br>　　　　　　　　　　α-L-Fucp-(1→3)—┘ | 94 |

TABLE 10-continued

| Source | Carbohydrates sub fragments | EM |
|---|---|---|
| a3 | α-L-Fucp-(1→4)—┐<br>                β-D-GlcpNAc-(1→3)-β-D-Galp-(1→4)-β-D-GlcpNAc-(1→6)-β-D-Galp-(1→<br>β-D-Galp-(1→3)—┘ | 95 |
| a3 | β-D-Galp-(1→3)-β-D-GlcpNAc-(1→3)-β-D-Galp-(1→4)—┐<br>                β-D-GlcpNAc-(1→6)-β-D-Galp-(1→<br>      α-L-Fucp-(1→3)—┘ | 96 |
| a3 | α-L-Fucp-(1→4)-β-D-GlcpNAc-(1→3)-β-D-Galp-(1→4)—┐<br>                β-D-GlcpNAc-(1→6)-β-D-Galp-(1→<br>      α-L-Fucp-(1→3)—┘ | 97 |
| a9;a10 | β-D-GlcpNAc-(1→3)-β-D-Galp-(1→4)—┐<br>                β-D-GlcpNAc-(1→3)-β-D-Galp-(1→4)-D-Glc<br>      α-L-Fucp-(1→3)—┘ | 98 |
| a9;a10 | β-D-Galp-(1→3)-β-D-GlcpNAc-(1→3)-β-D-Galp-(1→4)—┐<br>                β-D-GlcpNAc-(1→3)-β-D-Galp-(1→<br>      α-L-Fucp-(1→3)—┘ | 99 |
| a2 | α-L-Fucp-(1→3)-β-D-GlcpNAc-(1→6)—┐<br>α-L-Fucp-(1→4)—┐      β-D-Galp-(1→4)-D-Glc<br>      β-D-GlcpNAc-(1→3)—┘<br>β-D-Galp-(1→3)—┘ | 100 |
| a2 | β-D-Galp-(1→4)-β-D-GlcpNAc-(1→6)—┐<br>α-L-Fucp-(1→4)—┐      β-D-Galp-(1→4)-D-Glc<br>      β-D-GlcpNAc-(1→3)—┘<br>β-D-Galp-(1→3)—┘ | 101 |
| a2 | β-D-Galp-(1→4)—┐<br>      β-D-GlcpNAc-(1→6)—┐<br>α-L-Fucp-(1→3)—┘    β-D-Galp-(1→4)-D-Glc<br>α-L-Fucp-(1→4)-β-D-GlcpNAc-(1→3)—┘ | 102 |
| a10 | α-L-Fucp-(1→4)-β-D-GlcpNAc-(1→3)-β-D-Galp-(1→4)—┐<br>                β-D-GlcpNAc-(1→3)-β-D-Galp-(1→4)-D-Glc<br>      α-L-Fucp-(1→3)—┘ | 103 |
| a3 | α-L-Fucp-(1→4)—┐<br>                β-D-GlcpNAc-(1→3)-β-D-Galp-(1→4)-β-D-GlcpNAc-(1→6)-β-D-Galp-(1→4)-D-Glc<br>β-D-Galp-(1→3)—┘ | 104 |
| a3 | β-D-Galp-(1→3)-β-D-GlcpNAc-(1→3)-β-D-Galp-(1→4)—┐<br>                β-D-GlcpNAc-(1→6)-β-D-Galp-(1→4)-D-Glc<br>      α-L-Fucp-(1→3)—┘ | 105 |

TABLE 10-continued

| Source | Carbohydrates sub fragments | EM |
|---|---|---|
| a3 | α-L-Fucp-(1→4)-β-D-GlcpNAc-(1→3)-β-D-Galp-(1→4)┐<br>　　　　　　　　　　　　　　　　　　　β-D-GlcpNAc-(1→6)-β-D-Galp-(1→4)-D-Glc<br>　　　　　　　　　α-L-Fucp-(1→3)┘ | 106 |
| a3 | α-L-Fucp-(1→4)┐<br>　　　β-D-GlcpNAc-(1→3)-β-D-Galp-(1→4)┐<br>β-D-Galp-(1→3)┘　　　　　　　　　β-D-GlcpNAc-(1→6)-β-D-Galp-(1→<br>　　　　　　　　　α-L-Fucp-(1→3)┘ | 107 |
| a3 | α-L-Fucp-(1→4)┐<br>　　　β-D-GlcpNAc-(1→3)-β-D-Galp-(1→4)-β-D-GlcpNAc-(1→6)┐<br>β-D-Galp-(1→3)┘　　　　　　　　　　　　　　β-D-Galp-(1→<br>　　　　　　　　　β-D-GlcpNAc-(1→3)┘ | 108 |
| a3 | β-D-GlcpNAc-(1→3)-β-D-Galp-(1→4)┐<br>　　　　　　β-D-GlcpNAc-(1→6)┐<br>　α-L-Fucp-(1→3)┘　　　β-D-Galp-(1→<br>　β-D-Galp-(1→3)-β-D-GlcpNAc-(1→3)┘ | 109 |
| a3 | β-D-Galp-(1→3)-β-D-GlcpNAc-(1→3)-β-D-Galp-(1→4)┐<br>　　　　　　　　　　β-D-GlcpNAc-(1→6)┐<br>　　　α-L-Fucp-(1→3)┘　　　β-D-Galp-(1→<br>　　　　　β-D-GlcpNAc-(1→3)┘ | 110 |
| a3 | α-L-Fucp-(1→4)-β-D-GlcpNAc-(1→3)-β-D-Galp-(1→4)┐<br>　　　　　　　　　　β-D-GlcpNAc-(1→6)┐<br>　　　α-L-Fucp-(1→3)┘　　　β-D-Galp-(1→<br>　　　　　β-D-GlcpNAc-(1→3)┘ | 111 |
| a3 | α-L-Fucp-(1→4)-β-D-GlcpNAc-(1→3)-β-D-Galp-(1→4)-β-D-GlcpNAc-(1→6)┐<br>　　　　　　　　　　　　　　　　　　　　　β-D-Galp-(1→<br>　　β-D-Galp-(1→3)-β-D-GlcpNAc-(1→3)┘ | 112 |
| a10 | α-L-Fucp-(1→4)┐<br>　　　β-D-GlcpNAc-(1→3)-β-D-Galp-(1→4)┐<br>β-D-Galp-(1→3)┘　　　　　　　　　β-D-GlcpNAc-(1→3)-β-D-Galp-(1→<br>　　　　　　　　　α-L-Fucp-(1→3)┘ | 113 |
| a3 | α-L-Fucp-(1→4)┐<br>　　　β-D-GlcpNAc-(1→3)-β-D-Galp-(1→4)┐<br>β-D-Galp-(1→3)┘　　　　　　　　　β-D-GlcpNAc-(1→6)-β-D-Galp-(1→4)-D-Glc<br>　　　　　　　　　α-L-Fucp-(1→3)┘ | 114 |

TABLE 10-continued

| Source | Carbohydrates sub fragments | EM |
|---|---|---|
| a3 | α-L-Fucp-(1→4)—┐<br>　　　　　β-D-GlcpNAc-(1→3)-β-D-Galp-(1→4)-β-D-GlcpNAc-(1→6)—┐<br>β-D-Galp-(1→3)—┘　　　　　　　　　　　　　　　　β-D-Galp-(1→4)-D-Glc<br>　　　　　　　　　　　　　　　　β-D-GlcpNAc-(1→3)—┘ | 115 |
| a3 | β-D-GlcpNAc-(1→3)-β-D-Galp-(1→4)—┐<br>　　　　　　　　β-D-GlcpNAc-(1→6)—┐<br>　　α-L-Fucp-(1→3)—┘　　　β-D-Galp-(1→4)-D-Glc<br>β-D-Galp-(1→3)-β-D-GlcpNAc-(1→3)—┘ | 116 |
| a3 | β-D-Galp-(1→3)-β-D-GlcpNAc-(1→3)-β-D-Galp-(1→4)—┐<br>　　　　　　　　　β-D-GlcpNAc-(1→6)—┐<br>　α-L-Fucp-(1→3)—┘　　β-D-Galp-(1→4)-D-Glc<br>　　　　　β-D-GlcpNAc-(1→3)—┘ | 117 |
| a3 | α-L-Fucp-(1→4)-β-D-GlcpNAc-(1→3)-β-D-Galp-(1→4)—┐<br>　　　　　　　　β-D-GlcpNAc-(1→6)—┐<br>　α-L-Fucp-(1→3)—┘　　β-D-Galp-(1→4)-D-Glc<br>　　　β-D-GlcpNAc-(1→3)—┘ | 118 |
| a3 | α-L-Fucp-(1→4)-β-D-GlcpNAc-(1→3)-β-D-Galp-(1→4)-β-D-GlcpNAc-(1→6)—┐<br>　　　　　　　　　　　　　β-D-Galp-(1→4)-D-Glc<br>β-D-Galp-(1→3)-β-D-GlcpNAc-(1→3)—┘ | 119 |
| a3 | α-L-Fucp-(1→4)—┐<br>　　　β-D-GlcpNAc-(1→3)-β-D-Galp-(1→4)—┐<br>β-D-Galp-(1→3)—┘　　　β-D-GlcpNAc-(1→6)—┐<br>　　　　α-L-Fucp-(1→3)—┘　β-D-Galp-(1→<br>　　　　β-D-GlcpNAc-(1→3)—┘ | 120 |
| a3 | α-L-Fucp-(1→4)—┐<br>　　　β-D-GlcpNAc-(1→3)-β-D-Galp-(1→4)-β-D-GlcpNAc-(1→6)—┐<br>β-D-Galp-(1→3)—┘　　　　　　　　　　　β-D-Galp-(1→<br>　　β-D-Galp-(1→3)-β-D-GlcpNAc-(1→3)—┘ | 121 |
| a3 | α-L-Fucp-(1→4)-β-D-GlcpNAc-(1→3)-β-D-Galp-(1→4)—┐<br>　　　　　　　　β-D-GlcpNAc-(1→6)—┐<br>　α-L-Fucp-(1→3)—┘　　β-D-Galp-(1→<br>β-D-Galp-(1→3)-β-D-GlcpNAc-(1→3)—┘ | 122 |
| a3 | β-D-Galp-(1→3)-β-D-GlcpNAc-(1→3)-β-D-Galp-(1→4)—┐<br>　　　　　　　　　β-D-GlcpNAc-(1→6)—┐<br>　α-L-Fucp-(1→3)—┘　　β-D-Galp-(1→<br>β-D-Galp-(1→3)-β-D-GlcpNAc-(1→3)—┘ | 123 |

TABLE 10-continued

| Source | Carbohydrates sub fragments | EM |
|---|---|---|
| a3 | α-L-Fucp-(1→4)—┐<br>　　　　　　　　β-D-GlcpNAc-(1→3)-β-D-Galp-(1→4)—┐<br>β-D-Galp-(1→3)—┘<br>　　　　　　　　　　　　　　　　β-D-GlcpNAc-(1→6)—┐<br>　　　　　　　　α-L-Fucp-(1→3)—┘　　　　　β-D-Galp-(1→4)-D-Glc<br>　　　　　　　　β-D-GlcpNAc-(1→3)—┘ | 124 |
| a3 | α-L-Fucp-(1→4)-β-D-GlcpNAc-(1→3)-β-D-Galp-(1→4)—┐<br>　　　　　　　　　　　β-D-GlcpNAc-(1→6)—┐<br>　　　α-L-Fucp-(1→3)—┘　　　　β-D-Galp-(1→4)-D-Glc<br>　　　β-D-Galp-(1→3)-β-D-GlcpNAc-(1→3)—┘ | 125 |
| a3 | β-D-Galp-(1→3)-β-D-GlcpNAc-(1→3)-β-D-Galp-(1→4)—┐<br>　　　　　　　　　　　β-D-GlcpNAc-(1→6)—┐<br>　　　α-L-Fucp-(1→3)—┘　　　　β-D-Galp-(1→4)-D-Glc<br>　　　β-D-Galp-(1→3)-β-D-GlcpNAc-(1→3)—┘ | 126 |
| a3 | α-L-Fucp-(1→4)—┐<br>　　　　β-D-GlcpNAc-(1→3)-β-D-Galp-(1→4)-β-D-GlcpNAc-(1→6)—┐<br>β-D-Galp-(1→3)—┘　　　　　　　　　　　　　β-D-Galp-(1→4)-D-GLc<br>　　　　β-D-Galp-(1→3)-β-D-GlcpNAc-(1→3)—┘ | 127 |

*α-L-Fucp-(1→4)-β-D-GlcpNAc-(1→3)-β-D-Galp-(1→4)-β-D-GlcpNAc-(1→3)-β-D-Galp-(1→4)-D-Glc Table 11 includes a list of the EMs required for the synthesis of the complex carbohydrate collection described in Tables 9–10

TABLE 11

| EM | First Immobilized monosaccharide | ERs sequence (the ERs details are found in Table 7): |
|---|---|---|
| 1 | Glc-S | D9, H15, D10, H16, D7, B2 |
| 2 | Glc-S | D9, H15, D10, B6, H16, D7, B2 |
| 3 | Glc-S | D9, H15, D10, H16, D7, B2, H20, D10, B6 |
| 4 | Glc-S | D9, H15, D10, B1 |
| 5 | Glc-S | D9, H15, D7, B1 |
| 6 | Glc-S | D9, H15, D10, B6 |
| 7 | Glc-S | D9, H15, D10, B6, D1 |
| 8 | Glc-S | D9, H15, D10, B6, B7 |
| 9 | Glc-S | D9, H15, D7, H3, B2, D10 |
| 10 | Glc-S | D9, H15, D7, H3, B2, D10, B6 |
| 11 | Glc-S | D9, H15, D7, B2 |
| 12 | Glc-S | D9, H15, D7, B2, B1 |
| 13 | Glc-S | D9 |
| 14 | Glc-S | B8 |
| 15 | GlcNAc-S | D10 |
| 16 | GlcNAc-S | D7 |
| 17 | Gal-S | H21 |
| 18 | Gal-S | H22 |
| 19 | Gal-S | B1 |
| 20 | GlcNAc-S | B9 |
| 21 | GlcNAc-S | B10 |
| 22 | Gal-S | D9, H21 |
| 23 | Gal-S | D9, H22 |
| 24 | Gal-S | H22, D10 |
| 25 | Gal-S | H21, D7 |
| 26 | Gal-S | H22, D7 |
| 27 | Gal-S | H21, B10 |
| 28 | Gal-S | H22, B9 |
| 29 | GlcNAc-S | D10, B1 |
| 30 | GlcNAc-S | D7, B1 |
| 31 | Gal-S | H22, B10 |
| 32 | Glc-S | D9, H22, B10 |
| 33 | Glc-S | D9, H22, B9 |
| 34 | Glc-S | D9, H21, B10 |
| 35 | Glc-S | D9, H22, D7 |
| 36 | Glc-S | D9, H21, D7 |
| 37 | Glc-S | D9, H22, D10 |
| 38 | Gal-S | H22, D10, B1 |
| 39 | Gal-S | H22, D7, B1 |
| 40 | Gal-S | H22, D7, H3 |
| 41 | Glc-S | D9, H15, D7, H3 |
| 42 | Glc-S | D9, H21, D7, H3 |
| 43 | Gal-S | H21, D7, H3, B9 |
| 44 | Gal-S | H21, D7, H3, D10 |
| 45 | Gal-S | H22, D7, H3, D10 |
| 46 | Glc-S | D9, H21, D7, H3, D10 |
| 47 | Glc-S | D9, H22, D7, H3, B9 |
| 48 | Glc-S | D9, H21, D7, H3, B9 |
| 49 | Glc-S | D9, H22, D7, H3, D10 |
| 50 | Glc-S | D9, B7 |
| 51 | GlcNAc-S | D7, B2 |
| 52 | Gal-S | H21, H23 |
| 53 | GlcNAc-S | D10, B6 |
| 54 | Gal-S | H21, H23, B11 |
| 55 | Gal-S | H22, D7, B2 |
| 56 | GlcNAc-S | D7, B2, B1 |
| 57 | Gal-S | H22, D10, B6 |
| 58 | GlcNAc-S | D10, B6, B1 |

TABLE 11-continued

| EM | First Immobilized monosaccharide | ERs sequence (the ERs details are found in Table 7): |
|---|---|---|
| 59 | GlcNAc-S | D7, B2, H22 |
| 60 | Glc-S | D9, H21, H23 |
| 61 | Gal-S | H21, H23, B12 |
| 62 | Gal-S | H21, D7, B2 |
| 63 | Gal-S | H21, H23, D11 |
| 64 | Gal-S | H21, D7, B2 |
| 65 | Glc-S | D9, H21, H23, D11 |
| 66 | Glc-S | D9, H21, D7, B2 |
| 67 | Glc-S | D9, H21, H23, B12 |
| 68 | Glc-S | D9, H21, H23, D12 |
| 69 | Gal-S | H21, H23, B12, D11 |
| 70 | Gal-S | H21, H23, D11, D12 |
| 71 | Glc-S | D9, H21, H23, B11 |
| 72 | Glc-S | D9, H22, D11, B6 |
| 73 | Gal-S | H21, H23, D11, B6 |
| 74 | Gal-S | H21, H23, D12, B11 |
| 75 | Gal-S | H21, H23, B11, B12 |
| 76 | Glc-S | D9, B7, H22, D11 |
| 77 | Glc-S | D9, B7, H22, B11 |
| 78 | Gal-S | H22, D7, B2, B1 |
| 79 | Gal-S | H22, D7, H3, B2 |
| 80 | Glc-S | D9, H22, D7, B2 |
| 81 | Gal-S | H22, D11, B6, B1 |
| 82 | GlcNAc-S | D10, H3, D11, B6 |
| 83 | GlcNAc-S | D7, B2, H3, D11 |
| 84 | Glc-S | D9, H21, H23, D11, B12 |
| 85 | Glc-S | D9, H21, H23, D11, D12 |
| 86 | Glc-S | D9, H21, H23, D12, B2 |
| 87 | Gal-S | H21, H23, D12, B2, D11 |
| 88 | Glc-S | D9, H21, H23, D11, B6 |
| 89 | Glc-S | D9, H21, H23, D12, B11 |
| 90 | Glc-S | D9, H21, H23, B11, B12 |
| 91 | Gal-S | H21, H23, B12, D10, B6 |
| 92 | Gal-S | H21, H23, D12, D10, B6 |
| 93 | Gal-S | H21, H23, B11, D7, B2 |
| 94 | GlcNAc-S | D7, B2, H3, D10, B6 |
| 95 | Gal-S | H21, D12, H3, D10, B6 |
| 96 | Gal-S | H21, D12, B2, H3, D10 |
| 97 | Gal-S | H21, D12, B2, H3, B9 |
| 98 | Glc-S | D9, H15, D7, B2, H22 |
| 99 | Gal-S | H22, D7, B2, H22, D10 |
| 100 | Glc-S | D9, H21, H23, B12, D11, B6 |
| 101 | Glc-S | D9, H21, H23, D12, D11, B6 |
| 102 | Glc-S | D9, H21, H23, D12, B2, B11 |
| 103 | Glc-S | D9, H22, D7, B2, H22, B11 |
| 104 | Glc-S | D9, H21, D7, H3, D10, B6 |
| 105 | Glc-S | D9, H21, D7, B2, H22, D11 |
| 106 | Glc-S | D9, H21, D7, B2, H22, B11 |
| 107 | Gal-S | H21, D7, B2, H22, D11, B6 |
| 108 | Gal-S | H21, D12, H22, D11, B6, H23 |
| 109 | Gal-S | H21, H23, D12, B2, D11, H20 |
| 110 | Gal-S | H21, D12, H20, B2, D11, H23 |
| 111 | Gal-S | H21, D12, H20, B2, B11, H23 |
| 112 | Gal-S | H21, D12, H20, B9, H23, D11 |
| 113 | Gal-S | H22, D7, B2, H22, D11, B6 |
| 114 | Glc-S | D9, H21, D7, B2, H22, D11, B6 |
| 115 | Glc-S | D9, H21, D12, H22, D11, B6, H23 |
| 116 | Glc-S | D9, H21, H23, D12, B2, H3, D11 |
| 117 | Glc-S | D9, H21, D12, B2, H3, D11, H23 |
| 118 | Glc-S | D9, H21, D12, B2, H3, B11, H23 |
| 119 | Glc-S | D9, H21, D12, H3, B11, H23, D11 |
| 120 | Gal-S | H21, D12, B2, H3, D11, B6, H23 |
| 121 | Gal-S | H21, D12, H3, D11, B6, H23, D11 |
| 122 | Gal-S | H21, D12, B2, H3, B9, H23, D11 |
| 123 | Gal-S | H21, D12, B2, H3, D11, H23, D11 |
| 124 | Glc-S | D9, H21, D12, B2, H3, D11, B6, H23 |
| 125 | Glc-S | D9, H21, D12, B2, H3, D11, B6, H23 |
| 126 | Glc-S | D9, H21, D12, B2, H3, D11, H23, D11 |
| 127 | Glc-S | D9, H21, D12, H3, D11, B6, H23, D11 |

Example 2

Human chorionic gonadotropin (hCG) is a glycoprotein hormone produced by the trophoblast cells of the placenta. High levels of hCG are detected in blood and urine samples taken from patients of a variety of trophoblastic diseases. As such, urinary and serum hCG levels have been employed as useful markers for the diagnosis and prognosis of trophoblastic diseases, as well as being markers for pregnancy. A study comparing the complex carbohydrates released from hCGs purified from the urine of pregnant women with those purified from urine taken from patients with trophoblastic disease revealed the existence of several alteration in the sugar chains of hCGs purified from the latter (Mizuochi, 1983; Endo, 1987).

Tables 12–14 present the components and EMs necessary to synthesize a complex carbohydrate library for screening and isolating molecules that specifically bind to the abnormal hCG markers or to their subfragments. Tables 12–13 list complex carbohydrates structures incorporated into an hCG specific arrays. Such structures include abnormal sugar chains represented in the hCGs present in malignant trophoblastic diseases (marked B5, B6, B7 and B8), all the possible fragmented sugar chains of such hCGs present in malignant trophoblastic diseases (associated with B5, B6, B7 and B8 by b5, b6, b7 and b8, respectively), normal sugar chains as typically found in the hCGs present in the urine of pregnant women (marked B1, B2, B3 and B4) and all of their possible fragments (associated with B1, B2, B3 and B4 by b1, b2, b3 and b4, respectively). Table 14 presents the collection of EMs required for the synthesis of the complex carbohydrates of Tables 12–13.

TABLE 12

| Source | Carbohydrate | EM |
|---|---|---|
| B1;b5 Normal | 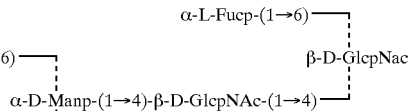 | 1 |

TABLE 12-continued

| Source | Carbohydrate | EM |
|---|---|---|
| B2;b1;b5;b6 Normal | β-D-Galp-(1→4)-β-D-GlcpNac-(1→2)-α-D-Manp-(1→6)⏋<br>　　　　　　　　　　　　　　　　　　　　　　　α-D-Manp-(1→4)-β-D-GlcpNAc-(1→4)-β-D-GlcpNac<br>β-D-Galp-(1→4)-β-D-GlcpNac-(1→2)-α-D-Manp-(1→3)⏌ | 2 |
| B3;b1;b2 Normal | α-D-Manp-(1→6)⏋<br>　　　　　　　　　　　　　　　α-D-Manp-(1→4)-β-D-GlcpNAc-(1→4)-β-D-GlcpN<br>β-D-Galp-(1→4)-β-D-GlcpNac-(1→2)-α-D-Manp-(1→3)⏌ | 3 |
| B4;b1;b5;b7 Normal | 　　　　　　　　　　　　　　　　　　　　　　　　　　α-L-Fuc-(1→6)⏋<br>α-D-Manp-(1→6)⏋　　　　　　　　　　　　　　　　　　　β-D-GlcpNac<br>　　　　　　　　　　α-D-Manp-(1→4)-β-D-GlcpNAc-(1→4)⏌<br>β-D-Galp-(1→4)-β-D-GlcpNac-(1→2)-α-D-Manp-(1→3)⏌ | 4 |
| B5 Abnormal | 　　　　　　　　　　　　　　　　　　　　　　　　　　α-L-Fuc-(1→6)⏋<br>β-D-Galp-(1→4)-β-D-GlcpNac-(1→2)-α-D-Manp-(1→6)⏋　β-D-GlcpNac<br>β-D-Galp-(1→4)-β-D-GlcpNac-(1→4)⏋　α-D-Manp-(1→4)-β-D-GlcpNAc-(1→4)⏌<br>　　　　　　　　　　　　α-D-Manp-(1→3)⏌<br>β-D-Galp-(1→4)-β-D-GlcpNac-(1→2)⏌ | 5 |
| B6 Abnormal | β-D-Galp-(1→4)-β-D-GlcpNac-(1→2)-α-D-Manp-(1→6)⏋<br>β-D-Galp-(1→4)-β-D-GlcpNac-(1→4)⏋　α-D-Manp-(1→4)-β-D-GlcpNAc-(1→4)-β-D-GlcpNac<br>　　　　　　　　　　　　α-D-Manp-(1→3)⏌<br>β-D-Galp-(1→4)-β-D-GlcpNac-(1→2)⏌ | 6 |
| B7;b5 Abnormal | 　　　　　　　　　　　　　　　　　　　　　　　　　　α-L-Fuc-(1→6)⏋<br>α-D-Manp-(1→6)⏋　　　　　　　　　　　　　　　　　　　β-D-GlcpNac<br>β-D-Galp-(1→4)-β-D-GlcpNac-(1→4)⏋　α-D-Manp-(1→4)-β-D-GlcpNAc-(1→4)⏌<br>　　　　　　　　　　　　α-D-Manp-(1→3)⏌<br>β-D-Galp-(1→4)-β-D-GlcpNac-(1→2)⏌ | 7 |
| B8;b5;b6;b7 Abnormal | α-D-Manp-(1→6)⏋<br>β-D-Galp-(1→4)-β-D-GlcpNac-(1→4)⏋　α-D-Manp-(1→4)-β-D-GlcpNAc-(1→4)-β-D-GlcpNac<br>　　　　　　　　　　　　α-D-Manp-(1→3)⏌<br>β-D-Galp-(1→4)-β-D-GlcpNac-(1→2)⏌ | 8 |

TABLE 13

| Source | Carbohydrate sub fragments | EM |
|---|---|---|
| b1;b4;b5;b7 | α-L-Fuc-(1→6)-β-D-GlcpNac | 9 |
| b1;b2;b3;b4;b5;b6;b7;b8 | β-D-GlcpNAc-(1→4)-β-D-GlcpNac | 10 |
| b1;b2;b3;b4;b5;b6;b7;b8 | α-D-Manp-(1→4)-β-D-GlcpNAc-(1→4)-β-D-GlcpNac | 11 |
| b1;b2;b3;b4;b5;b6;b7;b8 | α-D-Manp-(1→6)-α-D-Manp-(1→4)-β-D-GlcpNAc-(1→4)-β-D-GlcpNac | 12 |
| b1;b2;b3;b4;b5;b6;b7;b8 | α-D-Manp-(1→3)-α-D-Manp-(1→4)-β-D-GlcpNAc-(1→4)-β-D-GlcpNac | 13 |
| b1;b2;b5;b6 | β-D-GlcpNac-(1→2)-α-D-Manp-(1→6)-α-D-Manp-(1→4)-β-D-GlcpNAc-(1→4)-β-D-GlcpNac | 14 |
| b1;b2;b3;b4;b5;b6;b7;b8 | β-D-GlcpNac-(1→2)-α-D-Manp-(1→3)-α-D-Manp-(1→4)-β-D-GlcpNAc-(1→4)-β-D-GlcpNac | 15 |
| b5;b6;b7;b8 | β-D-GlcpNac-(1→4)-α-D-Manp-(1→3)-α-D-Manp-(1→4)-β-D-GlcpNAc-(1→4)-β-D-GlcpNac | 16 |
| b1;b2;b5;b6 | β-D-Galp-(1→4)-β-D-GlcpNac-(1→2)-α-D-Manp-(1→6)-α-D-Manp-(1→4)-β-D-GlcpNAc-(1→4)-β-D-GlcpNac | 17 |
| b1;b2;b3;b4;b5;b6;b7;b8 | β-D-Galp-(1→4)-β-D-GlcpNac-(1→2)-α-D-Manp-(1→3)-α-D-Manp-(1→4)-β-D-GlcpNAc-(1→4)-β-D-GlcpNac | 18 |

TABLE 13-continued

| Source | Carbohydrate sub fragments | EM |
|---|---|---|
| b5;b6;b7;b8 | β-D-Galp-(1→4)-β-D-GlcpNac-(1→4)-α-D-Manp-(1→3)-α-D-Manp-(1→4)-β-D-GlcpNAc-(1→4)-β-D-GlcpNac | 19 |
| b5;b6;b7;b8 | β-D-GlcpNac-(1→4)⏋<br>                    α-D-Manp-(1→<br>β-D-GlcpNac-(1→2)⏌ | 20 |
| b1;b4;b5;b7 | α-L-Fuc-(1→6)⏋<br>             β-D-GlcpNac<br>β-D-GlcpNac-(1→4)⏌ | 21 |
| b5;b6;b7;b8 | β-D-Galp-(1→4)-β-D-GlcpNac-(1→4)⏋<br>                                  α-D-Manp-(1→<br>                 β-D-GlcpNac-(1→2)⏌ | 22 |
| b5;b6;b7;b8 | β-D-GlcpNac-(1→4)⏋<br>                          α-D-Manp-(1→<br>β-D-Galp-(1→4)-β-D-GlcpNac-(1→2)⏌ | 23 |
| b1;b4;b5;b7 | α-L-Fuc-(1→6)⏋<br>                          β-D-GlcpNac<br>α-D-Manp-(1→4)-β-D-GlcpNac-(1→4)⏌ | 24 |
| b5;b6;b7;b8 | β-D-Galp-(1→4)-β-D-GlcpNac-(1→4)⏋<br>                                      α-D-Manp-(1→<br>β-D-Galp-(1→4)-β-D-GlcpNac-(1→2)⏌ | 25 |
| b5;b6;b7;b8 | α-D-Manp-(1→6)⏋<br>β-D-GlcpNac-(1→4)⏋  α-D-Manp-(1→<br>  α-D-Manp-(1→3)⏌<br>β-D-GlcpNac-(1→2)⏌ | 26 |
| b5;b6;b7;b8 | β-D-GlcpNac-(1→4)⏋<br>                        α-D-Manp-(1→3)-α-D-Manp-(1→<br>β-D-Galp-(1→4)-β-D-GlcpNac-(1→2)⏌ | 27 |
| b5;b6;b7;b8 | α-D-Manp-(1→6)⏋<br>                                  α-D-Manp-(1→<br>β-D-Galp-(1→4)-β-D-GlcpNac-(1→4)-α-D-Manp-(1→3)⏌ | 28 |
| b1;b4;b5;b7 | α-L-Fuc-(1→6)⏋<br>                                  β-D-GlcpNac<br>α-D-Manp-(1→6)-α-D-Manp-(1→4)-β-D-GlcpNAc-(1→4)⏌ | 29 |
| b1;b4;b5;b7 | α-L-Fuc-(1→6)⏋<br>                                  β-D-GlcpNac<br>α-D-Manp-(1→3)-α-D-Manp-(1→4)-β-D-GlcpNAc-(1→4)⏌ | 30 |
| b5;b6;b7;b8 | β-D-Galp-(1→4)-β-D-GlcpNac-(1→4)⏋<br>                                  α-D-Manp-(1→3)-α-D-Manp-(1→<br>β-D-Galp-(1→4)-β-D-GlcpNac-(1→2)⏌ | 31 |

TABLE 13-continued

| Source | Carbohydrate sub fragments | EM |
|---|---|---|
| b5;b6 | β-D-GlcpNac-(1→2)-α-D-Manp-(1→6)⎤<br>　　　β-D-GlcpNac-(1→4)⎤　　α-D-Manp-(1→<br>　　　　　　α-D-Manp-(1→3)⎦<br>　　　β-D-GlcpNac-(1→2)⎦ | 32 |
| b5;b6;b7;b8 | α-D-Manp-(1→6)⎤<br>　　β-D-GlcpNac-(1→4)⎤　α-D-Manp-(1→<br>　　　　α-D-Manp-(1→3)⎦<br>β-D-Galp-(1→4)-β-D-GlcpNac-(1→2)⎦ | 33 |
| b1;b2;b5;b6 | β-D-GlcpNac-(1→2)-α-D-Manp-(1→6)⎤<br>　　　　　α-D-Manp-(1→<br>β-D-Galp-(1→4)-β-D-GlcpNac-(1→4)-α-D-Manp-(1→3)⎦ | 34 |
| b1;b4;b5;b7 | α-L-Fuc-(1→6)⎤<br>β-D-GlcpNac<br>β-D-GlcpNac-(1→2)-α-D-Manp-(1→3)-α-D-Manp-(1→4)-β-D-GlcpNAc-(1→4)⎦ | 35 |
| b1;b5 | α-L-Fuc-(1→6)⎤<br>β-D-GlcpNac<br>β-D-GlcpNac-(1→2)-α-D-Manp-(1→6)-α-D-Manp-(1→4)-β-D-GlcpNAc-(1→4)⎦ | 36 |
| b5;b6;b7;b8 | α-L-Fuc-(1→6)⎤<br>β-D-GlcpNac<br>β-D-GlcpNac-(1→4)-α-D-Manp-(1→3)-α-D-Manp-(1→4)-β-D-GlcpNAc-(1→4)⎦ | 37 |
| b1;b5 | α-L-Fuc-(1→6)⎤<br>β-D-GlcpNac<br>β-D-Galp-(1→4)-β-D-GlcpNac-(1→2)-α-D-Manp-(1→6)-α-D-Manp-(1→4)-β-D-GlcpNAc-(1→4)⎦ | 38 |
| b1;b4;b5;b7 | α-L-Fuc-(1→6)⎤<br>β-D-GlcpNac<br>β-D-Galp-(1→4)-β-D-GlcpNac-(1→2)-α-D-Manp-(1→3)-α-D-Manp-(1→4)-β-D-GlcpNAc-(1→4)⎦ | 39 |
| b5 | α-L-Fuc-(1→6)⎤<br>β-D-GlcpNac<br>β-D-Galp-(1→4)-β-D-GlcpNac-(1→4)-α-D-Manp-(1→3)-α-D-Manp-(1→4)-β-D-GlcpNAc-(1→4)⎦ | 40 |
| b5;b6;b7;b8 | α-D-Manp-(1→6)⎤<br>　　β-D-Galp-(1→4)-β-D-GlcpNac-(1→4)⎤　α-D-Manp-(1→<br>　　　　α-D-Manp-(1→3)⎦<br>β-D-Galp-(1→4)-β-D-GlcpNac-(1→2)⎦ | 41 |
| b5;b6 | β-D-Galp-(1→4)-β-D-GlcpNac-(1→2)-α-D-Manp-(1→6)⎤<br>　　　β-D-GlcpNac-(1→4)⎤　α-D-Manp-(1→<br>　　　　α-D-Manp-(1→3)⎦<br>　　β-D-GlcpNac-(1→2)⎦ | 42 |

TABLE 13-continued

| Source | Carbohydrate sub fragments | EM |
|---|---|---|
| b5;b6 | β-D-GlcpNac-(1→2)-α-D-Manp-(1→6)─┐<br>β-D-GlcpNac-(1→4)─┐    α-D-Manp-(1→<br>          α-D-Manp-(1→3)─┘<br>β-D-Galp-(1→4)-β-D-GlcpNac-(1→2)─┘ | 43 |
| b5;b6;b7;b8 | β-D-Galp-(1→4)-β-D-GlcpNac-(1→4)─┐<br>      α-D-Manp-(1→3)-α-D-Manp-(1→4)-β-D-GlcpNAc-(1→<br>β-D-Galp-(1→4)-β-D-GlcpNac-(1→2)─┘ | 44 |
| b1;b2;b5;b6 | β-D-Galp-(1→4)-β-D-GlcpNac-(1→2)-α-D-Manp-(1→6)─┐<br>      α-D-Manp-(1→<br>β-D-Galp-(1→4)-β-D-GlcpNac-(1→4)-α-D-Manp-(1→3)─┘ | 45 |
| b5;b6 | β-D-GlcpNac-(1→2)-α-D-Manp-(1→6)─┐<br>β-D-Galp-(1→4)-β-D-GlcpNac-(1→4)─┐  α-D-Manp-(1→<br>         α-D-Manp-(1→3)─┘<br>β-D-Galp-(1→4)-β-D-GlcpNac-(1→2)─┘ | 46 |
| b5;b6 | β-D-Galp-(1→4)-β-D-GlcpNac-(1→2)-α-D-Manp-(1→6)─┐<br>β-D-Galp-(1→4)-β-D-GlcpNac-(1→4)─┐  α-D-Manp-(1→<br>         α-D-Manp-(1→3)─┘<br>β-D-GlcpNac-(1→2)─┘ | 47 |
| b5;b6 | β-D-Galp-(1→4)-β-D-GlcpNac-(1→2)-α-D-Manp-(1→6)─┐<br>β-D-GlcpNac-(1→4)─┐    α-D-Manp-(1→<br>      α-D-Manp-(1→3)─┘<br>β-D-Galp-(1→4)-β-D-GlcpNac-(1→2)─┘ | 48 |
| b1;b2;b5;b6 | β-D-Galp-(1→4)-β-D-GlcpNac-(1→2)-α-D-Manp-(1→6)─┐<br>      α-D-Manp-(1→4)-β-D-GlcpNAc-(1→<br>β-D-Galp-(1→4)-β-D-GlcpNac-(1→4)-α-D-Manp-(1→3)─┘ | 49 |
| b5;b6 | β-D-Galp-(1→4)-β-D-GlcpNac-(1→2)-α-D-Manp-(1→6)─┐<br>β-D-Galp-(1→4)-β-D-GlcpNac-(1→4)─┐  α-D-Manp-(1→<br>         α-D-Manp-(1→3)─┘<br>β-D-Galp-(1→4)-β-D-GlcpNac-(1→2)─┘ | 50 |

Table 14 includes a list of the EMs required for the synthesis of the complex carbohydrate collection described in Tables 12–13.

TABLE 14

| EM | First immobilized monosaccharide | ERs sequence (ERs details describe in Table 7) |
|---|---|---|
| 1 | GlcpNac-S | H17, C1, C4, H8, C5, H10, D7, B3 |
| 2 | GlcpNac-S | H17, C1, C4, H8, C5, H10, D7 |
| 3 | GlcpNac-S | H17, C1, C4, H8, C5, D7, H10 |
| 4 | GlcpNac-S | H17, C1, C4, H8, C5, D7, H10, D7, B3 |
| 5 | GlcpNac-S | H17, C1, C4, H8, H9, C5, H10, D7, B3 |
| 6 | GlcpNac-S | H17, C1, C4, H8, H9, C5, H10, D7 |
| 7 | GlcpNac-S | H17, C1, C4, H8, H9, C5, D7, B3 |
| 8 | GlcpNac-S | H17, C1, C4, H8, H9, C5, D7, B3 |
| 9 | GlcpNac-S | B4 |
| 10 | GlcpNac-S | H17 |
| 11 | GlcpNac-S | H17, C1 |
| 12 | GlcpNac-S | H17, C1, C7 |
| 13 | GlcpNac-S | H17, C1, C4 |
| 14 | GlcpNac-S | H17, C1, C7, H10 |
| 15 | GlcpNac-S | H17, C1, C4, H8 |
| 16 | GlcpNac-S | H17, C1, C4, H9 |

TABLE 14-continued

| EM | First immobilized monosaccharide | ERs sequence (ERs details describe in Table 7) |
|---|---|---|
| 17 | GlcpNac-S | H17, C1, C7, H10, D7 |
| 18 | GlcpNac-S | H17, C1, C4, H8, D7 |
| 19 | GlcpNac-S | H17, C1, C4, H9, D7 |
| 20 | D-Man-α-(1,0)-S | H18, H19 |
| 21 | GlcpNac-S | H17, B5 |
| 22 | D-Man-α-(1,0)-S | H18, D7, H19 |
| 23 | D-Man-α-(1,0)-S | H18, H19, D7 |
| 24 | GlcpNac-S | H17, C1, B3 |
| 25 | D-Man-α-(1,0)-S | H18, H19, D7 |

Example 3

During the latter half of the century it has been demonstrated that many bacterial, fungal and plant polysaccharides posses anti-viral, anti-coagulant, anti-thrombotic, anti-cardiovascular and anti-tumor activities (Witczak, 1997). It was also found that a general structural pattern is common to all of these complex carbohydrates. Most of these complex carbohydrates include one or two repeating monosaccharide units connected with one or two types of glycosidic bonds and decorated with branched points of constant length.

Table 15 summarizes partial examples of such unique structures.

TABLE 15

| Source | Common name | Activity | Monosaccharide content | Configuration | Reference |
|---|---|---|---|---|---|
| *Nothogenia fastigiata* | Xylomannan | antiviral | xylose-mannose | 1,3-linked mannose (98%) sulfated in position 2 and 6 with single stubs of β-1,2-xylose | Matulewicz, 1978 |
| *Agardhiella tenera* | Galactan sulfate | antiviral | galactose | 1,3-linked D- and L-galactose with 3,6-anhydro-D- and L-galactose with half ester sulfate | Rees, 1965 |
| *Ecklonica kurome* | Fucoidan | anti coagulant | fucose | α-1,2-linked units of L-fucose-4-sulfate with branching or second sulfate unit in position 3 | Nishino, 1989 |
| *Saccharomyces cerevisia* | Glucan (Zymosan) | anti tumor | glucose | β-1,3-D-glucose with β-1,6-D-glucose branches | Konis, 1976; Misaki, 1968 |
| *Mycobacterium bovis* | LAM | evoking TNF and other cytokines | arabinose-mannose | α-1,6-D-mannose core with α-1,2-D-mannose branches elongate with linear α-1,5-D-arabinose chain | Chatterjee, 1998; Nigou, 1997 |
| *Alcaligenes faecalis* var. | Crudlan | anti tumor | glucose | Linear β-1,3-D-glucose | Sasaki, 1978 |
| Chemical synthesis | Ara-Crudlan | anti tumor | arabinose-glucose | β-1,3-D-glucose with α-1,5-D-arabinose linked at position 4 or 6 | Matuzaki, 1986 |

TABLE 14-continued

| EM | First immobilized monosaccharide | ERs sequence (ERs details describe in Table 7) |
|---|---|---|
| 26 | D-Man-α-(1,0)-S | C8, H8, H9, C7 |
| 27 | D-Man-α-(1,0)-S | C8, H8, D7, H9 |
| 28 | D-Man-α-(1,0)-S | C8, H8, D7, C7 |
| 29 | GlcpNac-S | H17, C1, C7, B3 |
| 30 | GlcpNac-S | H17, C1, C4, B3 |
| 31 | D-Man-α-(1,0)-S | C8, H8, H9, D7 |
| 32 | D-Man-α-(1,0)-S | C8, H8, H9, C7, H10 |
| 33 | D-Man-α-(1,0)-S | C8, H8, D7, H9, C7 |
| 34 | D-Man-α-(1,0)-S | C8, H8, D7, C7, H10 |
| 35 | GlcpNac-S | H17, C1, C4, H8, B3 |
| 36 | GlcpNac-S | H17, C1, C7, H10, B3 |
| 37 | GlcpNac-S | H17, C1, C8, H9, B3 |
| 38 | GlcpNac-S | H17, C1, C4, H8, B3, D7 |
| 39 | GlcpNac-S | H17, C1, C7, H10, B3, D7 |
| 40 | GlcpNac-S | H17, C1, C8, H9, B3, D7 |
| 41 | D-Man-α-(1,0)-S | C8, H8, H9, C7, D7 |
| 42 | D-Man-α-(1,0)-S | C7, H10, D7, H8, H9 |
| 43 | D-Man-α-(1,0)-S | C8, H8, D7, H9, C7, H10 |
| 44 | D-GlcpNac-β-(1,0)-S | C9, C10, H8, H9, D7 |
| 45 | D-Man-α-(1,0)-S | C7, H8, C8, H10, D7 |
| 46 | D-Man-α-(1,0)-S | C7, H8, H9, D7, C8, H10 |
| 47 | D-Man-α-(1,0)-S | C7, H9, C8, H10, D7, C8 |
| 48 | D-Man-α-(1,0)-S | C7, H8, C8, H10, D7, H8 |
| 49 | D-GlcpNac-β-(1,0)-S | C9, C10, H8, C5, H10, D7 |
| 50 | D-Man-α-(1,0)-S | C7, H8, H9, C8, H10, D7 |

Viscosity studies as well as X-ray analysis suggested that possible helical and triple helical structures are responsible for the abovementioned activities (Misaki, 1997). However, further studies demonstrated that fragments derived from partial hydrolysis of these complex carbohydrates also posses some therapeutic activities (Misaki, 1980).

As such, the present invention can be utilized to screen combinatorial oligosaccharide libraries which include short oligomers derived from the complex carbohydrates listed above. Such fragments can, for example, include one or two repeating monosaccharide units attached therebetween through one or two types of glycosidic bonds. Such fragments can also include moderate branching, when required. Such combinatorial arrays of polysaccharides can be utilized for the isolation of new anti-viral, anti-coagulant, anti-thrombotic, anti-cardiovascular and anti-tumor agents.

Example 4

The following example represents synthesized complex carbohydrates including β(1,3)D-glucose and β(1,6)D-glucose branches. Each of the oligomers shown includes 7 monomers. It will be appreciated that an oligomer consisting of 2 to 30 units or more can also be synthesized by the method of the present invention as described herein.

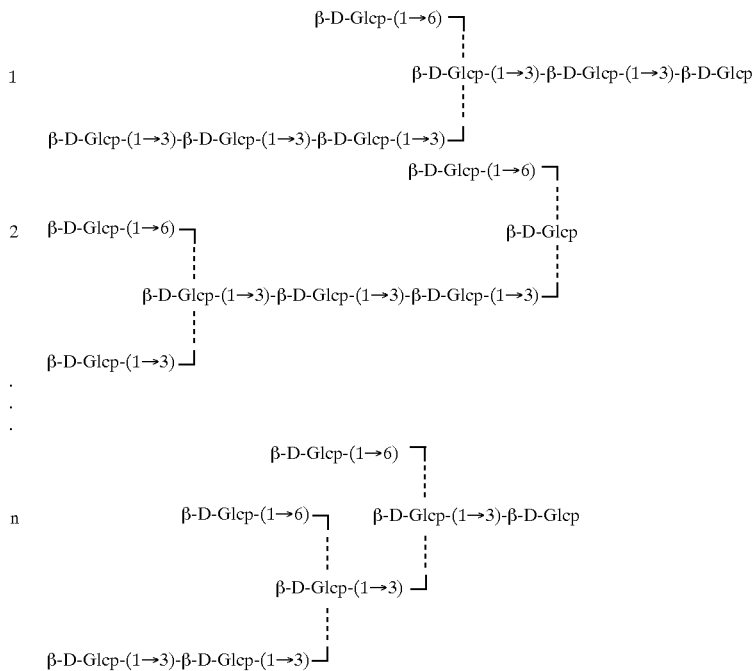

Example 5

The following example represents synthesized complex carbohydrates consisting of a backbone of β(1,3)D-glucose units and α(1,5)D-arabinose branches, which are positioned at any desired location along the backbone. Each of the oligomers shown below includes 12 monomers. It will be appreciated that an oligomer consisting of 2 to 40 units or more can also be synthesized by the method of the present invention.

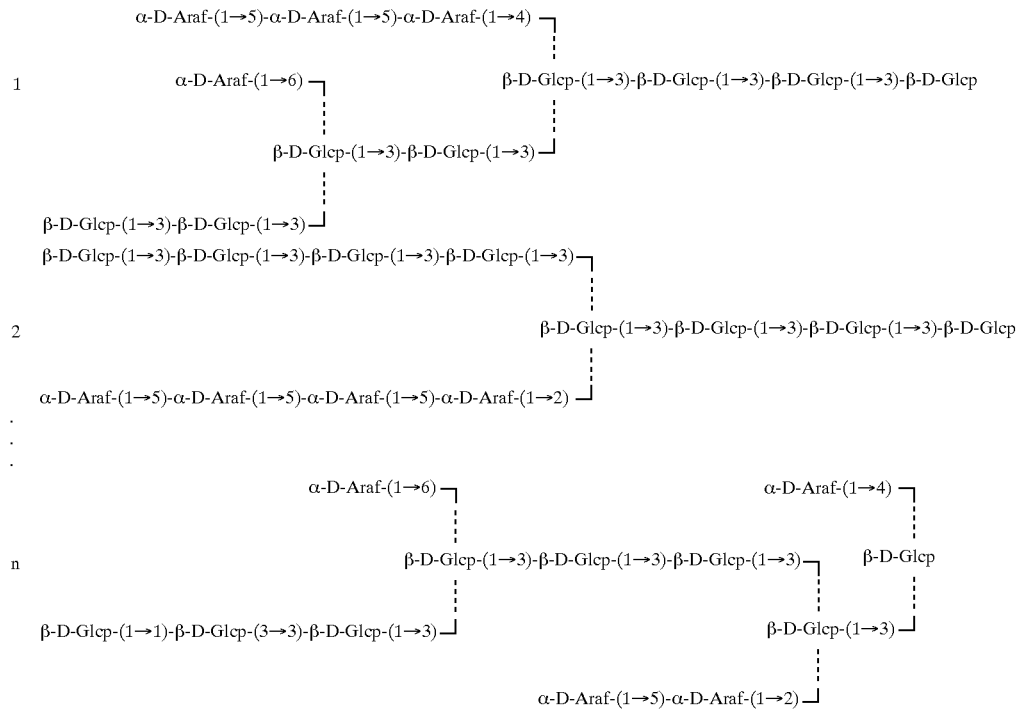

Example 6

The following example represents synthesized complex carbohydrates consisting of α(1,2)linked α-L-fucose or α-L-fucose-4-sulfate with branching or secondary sulfate units positioned at position 3. Each of the oligomers shown below includes 6 saccharide monomers. It will be appreciated that an oligomer consisting of 2 to 20 units or more can also be synthesized by the method of the present invention.

Example 7

The following example represents synthesized complex carbohydrates consisting of (1,3) linked α-D-mannose or α-D-mannose sulfated positioned at position 2 and/or 6, and including β(1,2)xylose stubs. Each of the oligomers shown below includes 5 saccharide monomers. It will be appreciated that an oligomer consisting of 3 to 20 units or more can also be synthesized by the method of the present invention.

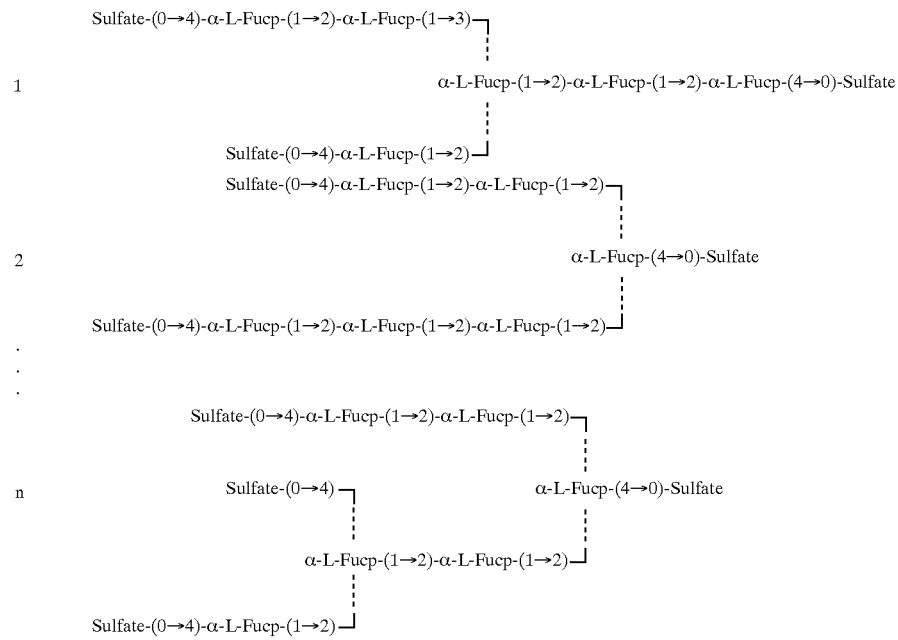

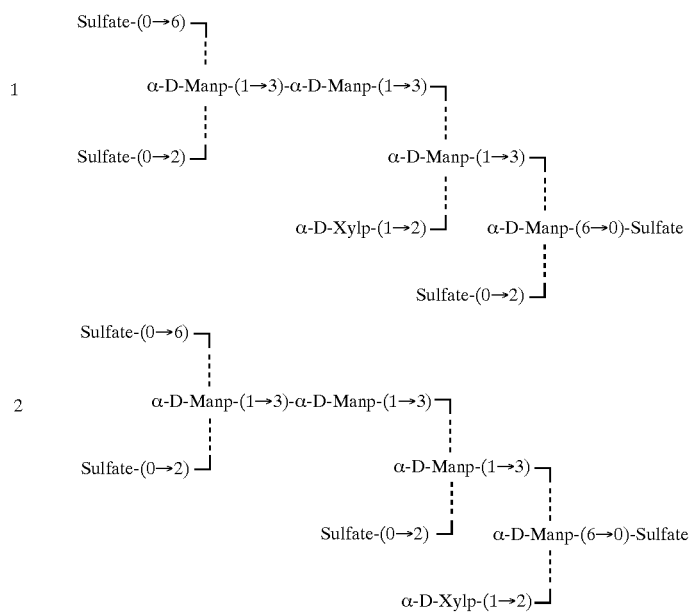

.
.
.

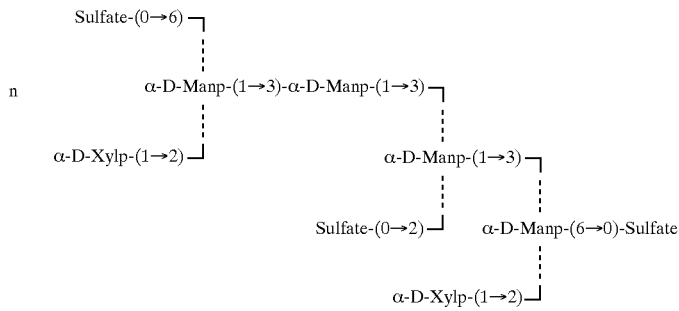

Example 8

The following example represents synthesized complex carbohydrates consisting of α(1,5)D-arabinose and α(1,2) D-mannose units with a core of α-D-arabinose unit connected to the α-D-arabinose unit at position 2 or to the α-D-mannose unit at any position. Each of the oligomers shown below includes 9 saccharide monomers. It will be appreciated that an oligomer consisting of 2 to 70 units or more can also be synthesized by the method of the present invention.

unit, which is connected to the α-D-arabinose unit at position 2 or to the α-D-mannose unit at any position. The complex carbohydrate also include a branched β-D-arabinose which is positioned at position 3. The branch antenna includes, as a major oligomer, a single core β-D-arabinose unit connected to α-D-arabinose at position 2 or to α-D-mannose at any position. Each of the oligomers shown below includes 14 saccharide monomers. It will be appreciated that an oligomer consisting of 2 to 70 units or more can also be synthesized by the method of the present invention.

1   α-D-Manp-(1→2)-α-D-Manp-(1→2)-β-D-Araf-(1→2)-α-D-Araf-(1→5)-α-D-Araf-(1→5)-α-D-Araf-(1→5)-α-D-Manp-(1→2)-α-D-Manp-(1→5)-α-D-Araf 2   α-D-Manp-(1→2)-α-D-Manp-(1→2)-β-D-Araf-(1→2)-α-D-Araf-(1→5)-α-D-Araf-(1→5)-α-D-Araf-(1→5)-α-D-Araf-(1→2)-α-D-Manp-(1→5)-α-D-Araf

.
.
.

n   α-D-Manp-(1→2)-α-D-Manp-(1→2)-β-D-Araf-(1→2)-α-D-Araf-(1→5)-α-D-Araf-(1→5)-α-D-Araf-(1→5)-α-D-Araf-(1→5)-α-D-Araf-(1→5)-α-D-Araf

Example 9

The following example represents synthesized complex carbohydrates consisting of α-1,5-D-arabinose and α-1,2-D-mannose units attached to a single core β-D-arabinose

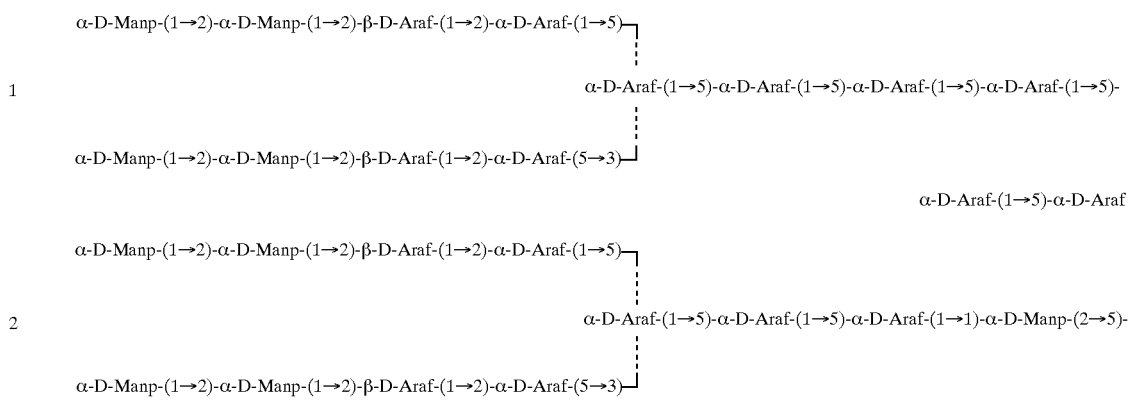

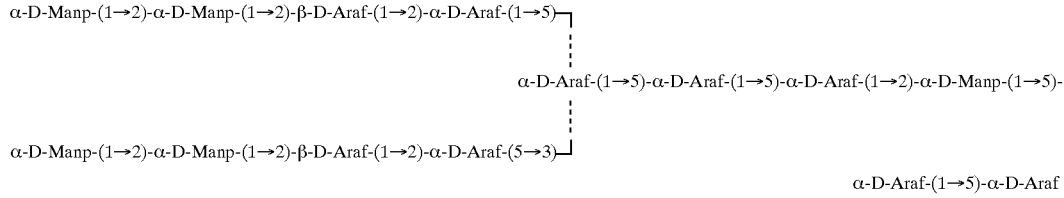

Complex Carbohydrate Library Synthesis

The following examples describe in detail experiments demonstrating sequential enzymatic synthesis of complex carbohydrates libraries according to the teachings of the present invention.

Materials and Methods

Abbreviations used below: BSA—Bovine Serum Albumin; GlcNAc—N-acetylglucoseamine; PNP-GlcNAc—p-nitrophenyl-N-acetyl-β-D-GlcNAc; GlcNAc-COOH—2-(2-carboxyethylthio)-ethyl 2-β-D-GlcNAc; NHS—N-hydroxysuccinimide; EDC—1-Ethyl-3-(3dimethylaminopropyl)-carbodiimide; O.D.—Optical Density; WGA—Wheat Germ Agglutinin; RCA120—lectin from *Ricinus communis*; BS-I—Lectin from *Bandeiraea Simplicifolia*; TGP—Lectin from *Tereagonolobus purpureas*; TML—Lectin from *Tritrichomonas mobilensis*; ECorA—Lectin from *Erythrina corallodendron*; FITC—Fluoresceine-iso-thio-cyanate.

General materials: PBS—0.1M phosphate buffer pH 7.5, 0.15M NaCl (Sigma S-7653); TBS—50 mM Tris/HCl pH 7.5 (Sigma T-6791), 0.15M NaCl; TBST—TBS, 0.05% Tween 20 (Sigma P-9416); High ionic strength washing buffer-PBS, 2M NaCl, 60 millimolar MgSO$_4$, 0.05% Tween 20. A peroxidase substrate solution was prepared by mixing in water O-Phenylenediamine Dihydrochloride, 0.4 mg/ml, Urea Hydrogen peroxide, 0.4 mg/ml, Phosphate-Citrate Buffer, 0.05M (prepared from SIGMA FAST peroxidase substrate kit P-9187). Covalink NH was obtained from NUNC (Cat. No. 478042). Optical density and fluorescence were measured using a multi-label counter VICTOR$^2$ (Wallac OY, Finland). All microtiter plate incubations were performed at controlled shaking speed and temperature using a microtiter plate incubator obtained from Anthos Thermostar Shaker/Incubator, Rosys Anthos GmbH Salzburg Austria (Cat. No. 8850001).

General enzymatic reaction mixes and conditions (ER's):

D7: 100 μl of 50 mM MOPS (SIGMA M-9027), 10 mg/ml BSA (SIGMA A-7030), 20 MM MnCl$_2$ (SIGMA M-9522), 0.5 mg/ml UDP-Gal (Calbiochem 670111) and 20 milliunits/ml of recombinant β 1,4 galactosyltransferase (Calbiochem 345650) at pH 7.4 were added to each well of a microtiter plate and the plate was shaken at 50 RPM at 37° C. for 3 hours. Following incubation, the reaction mixture was removed and the wells were washed three times with 200 μl of TBST, the last wash consisting of a 15 minutes soak. The TBST was replaced with TBS 0.2% NaN$_3$ (Sigma S-8032) and the plate was stored at 4° C. for subsequent enzymatic reactions.

A2: 100 μl of 50 mM MOPS (SIGMA M-9027), 10 mg/ml BSA (SIGMA A-7030), 0.5 mg/ml CMP-NeuAC (Calbiochem 233263), and 5 milliunits/ml of recombinant α2,3 (N)-sialyltransferase (Calbiochem 566218) at pH 7.4 were added to each well of a microtiter plate and the plate was shaken at 50 RPM at 37° C. for 4 hours. Following incubation, the reaction mixture was removed and the wells were washed three times with 200 μl of TBST, the last wash consisting of a 15 minutes soak. The TBST was replaced with TBS 0.2% NaN$_3$ (Sigma S-8032) and the plate was stored at 4° C. for subsequent enzymatic reactions.

B2: 100 μl of 50 mM MOPS (SIGMA M-9027), 10 mg/ml BSA (SIGMA A-7030), 20 mM MnCl$_2$ (SIGMA M-9522), 0.5 mg/ml GDP-Fuc (Calbiochem 371443) and 5 milliunits/ml of recombinant α1,3 fucosyltransferase (Calbiochem 344323) at pH 7.2 were added to each well of a microtiter plate and the plate was shaken at 50 RPM at 37° C. for 4 hours. Following incubation, the reaction mixture was removed and the wells were washed three times with 200 μl of TBST, the last wash consisting of a 15 minutes soak. The TBST was replaced with TBS 0.2% NaN$_3$ (Sigma S-8032) and the plate was stored at 4° C. for subsequent enzymatic reactions.

D3: 100 μl of 100 mM sodium cacodylate buffer (SIGMA C-4945), 10 mg/ml BSA (SIGMA A-7030), 20 mM MnCl$_2$ (SIGMA M-9522), 0.5 mg/ml UDP-Gal (Calbiochem 670111) and 5 milliunits/ml of recombinant α1,3 galactosyltransferase (Calbiochem 345648) at pH 6.5 were added to each well of a microtiter plate and the plate was shaken at 50 RPM at 37° C. for 4 hours. Following incubation, the reaction mixture was removed and the wells were washed three times with 200 μl of TBST, the last wash consisting of a 15 minutes soak. The TBST was replaced with TBS 0.2% NaN$_3$ (Sigma S-8032) and the plate was stored at 4° C. for subsequent enzymatic reactions.

A3: 100 μl of 50 mM sodium cacodylate buffer (SIGMA C-4945), 10 mg/ml BSA (SIGMA A-7030), 0.5 mg/ml CMP-NeuAC (Calbiochem 233263) and 5 milliunits/ml of Recombinant α2,6-(N)-sialyltransferase (Calbiochem 566222) at pH 6.0 were added to each well of a microtiter plate and the plate was shaken at 50 RPM at 37° C. for 4 hours. Following incubation, the reaction mixture was removed and the wells were washed three times with 200 μl of TBST, the last wash consisting of a 15 minutes soak. The TBST was replaced with TBS 0.2% NaN$_3$ (Sigma S-8032) and the plate was stored at 4° C. for subsequent enzymatic reactions.

H3: 100 μl of 50 mM sodium cacodylate buffer (SIGMA C-4945), 20 mM MnCl$_2$ (SIGMA M-9522) 10 mg/ml BSA (SIGMA A-7030), 5% dimethylsulfoxide, 0.5 millimolar UDP-GlcNAc (Calbiochem 670107), 0.75 millimolar adenosine three phosphate and 5 milliunits/ml of recombinant β1,3 N acetylglucoseaminyl-transferase (prepared as described in Zhou et al., *Proc. Natl. Acad. Sci.* USA Vol. 96 pp. 406–411) at pH 7.0 are added to each well of a microtiter plate and the plate is shaken at 50 RPM at 37° C. for 10 hours. Following incubation, the reaction mixture is removed and the wells are washed three times with 200 μl of TBST, the last wash consisting of a 15 minutes soak. The TBST is replaced with TBS 0.2% NaN$_3$ (Sigma S-8032) and the plate are stored at 4° C. for subsequent enzymatic reactions.

The BSA of the reaction mixture is omitted and the wash steps are performed using high ionic strength buffer instead of TBST when the enzymatic reactions are performed in Covalink NH plates including a covalently coupled monosaccharide.

Lectin/antibody binding assays:

WGA: 100 μl of 5 μl/ml WGA lectin conjugated to peroxidase (SIGMA L-3892, 150 peroxidase units per mg protein) was added to the plates and incubated for 1 hour at 25° C. in TBS containing 1% BSA and 10 millimolar of MnCl$_2$ and of CaCl$_2$. The wells were washed 3 times with 200 μl TBST, with a last wash consisting of a 15 minutes soak. To detect the peroxidase labeled WGA, 100 μl of fresh peroxidase substrate solution was added, and an hour later the O.D. of the solution (at 450 nm) was determined.

RCA120: 100 μl of 10 μg/ml RCA120 lectin conjugated to peroxidase (SIGMA L-2758, 11 peroxidase units per mg protein) was added to the plates and incubated for 1 hour at 25° C. in TBS containing 1% BSA and 10 millimolar each of MnCl$_2$ and CaCl$_2$. The wells were washed three times with 200 μl TBST with a last wash consisting of a 15 minutes soak. 100 μl of fresh peroxidase substrate solution was added, and an hour later the O.D. of the solution (at 450 nm) was determined.

TGP: 100 μl of 20 μg/ml TGP lectin conjugated to peroxidase (SIGMA L-1508, 10 peroxidase units per mg protein) was added to the plates and incubated for one hour at 25° C. in TBS containing 1% BSA and 10 millimolar of MnCl$_2$ and of CaCl$_2$. The wells were washed three times with 200 μl TBST with a last wash consisting of a 15 minutes soak. 100 μl of fresh peroxidase substrate solution was added, and an hour later the O.D. of the solution (at 450 nm) was determined.

BS-4: 100 μl of 20 μl/ml BS-I conjugated to biotin (SIGMA L-3759) was added to the plates and incubated for 1 hour at 25° C. in TBS containing 1% BSA and 10 millimolar of MnCl$_2$ and of CaCl$_2$. The wells were washed three times with 200 μl TBST with a last wash consisting of a 15 minutes soak, following which, 100 μl of TBS containing 1% BSA and 5 μg/ml avidin conjugated to peroxidase (SIGMA A-3151, 40 peroxidase units per mg protein) was added to the plates and incubated for 1 hour at 25° C. The wells were washed three times with 200 μl TBST with a last wash consisting of a 15 minutes soak. 100 μl of fresh peroxidase substrate solution was added, and an hour later the O.D. of the solution (at 450 nm) was determined.

TML: 100 μl of 20 μg/ml TML conjugated to biotin (Calbiochem 431803) was added to the plates and incubated for 1 hour at 25° C. in TBS containing 1% BSA. The wells were washed 3 times with 200 μl TBST with a last wash consisting of a 15 minutes soak, following which, 100 μl of TBS containing 1% BSA and 5 μl/ml avidin conjugated to peroxidase (SIGMA A-3151, 40 peroxidase units per mg protein) was added to the plates and incubated for 1 hour at 25° C. The wells were washed 3 times with 200 μl TBST with a last wash consisting of a 15 minutes soak. 100 μl of fresh peroxidase substrate solution was added, and an hour later the O.D. of the solution (at 450 nm) was determined.

Anti-Sialyl Lewis X: 100 μl of 10 μg/ml anti-Sialyl Lewis X IgM from mouse (Calbiochem 565953) was added to the plates and incubated for 1 hour at 25° C. in TBS containing 1% BSA. The wells were washed 3 times with 200 μl TBST with a last wash consisting of a 15 minutes soak, following which, a solution of TBS containing 1% BSA and 100 μl of 5 μg/ml goat anti-mouse IgM conjugated to biotin (SIGMA b-9265) was added to the plates and incubated for one hour at 25° C. The wells were washed 3 times with 200 ml TBST with a last wash consisting of a 15 minutes soak, followed by incubation with 100 ml of TBS containing 1% BSA and 5 μg/ml avidin conjugated to peroxidase (SIGMA A-3151, 40 peroxidase units per mg protein) for 1 hour at 25° C. The wells were washed three times with 200 μl TBST with a last wash consisting of a 15 minutes soak. 100 μl of fresh peroxidase substrate solution was added, and an hour later the O.D. of the solution (at 450 nm) was determined.

ECorA: 100 μl of 20 μg/ml ECorA conjugated to biotin (SIGMA L-0893) were added to the plates and incubated for 1 hour at 25° C. in TBS containing 1% BSA and 10 millimolar of MnCl$_2$ and of CaCl$_2$. The wells were washed three times with 200 μl TBST with a last wash consisting of a 15 minutes soak, following which, 100 μl of TBS containing 1% BSA and 5 μg/ml avidin conjugated to peroxidase (SIGMA A-3151, 40 peroxidase units per mg protein) was added to the plates and incubated for 1 hour at 25° C. The wells were washed three times with 200 μl TBST with a last wash consisting of a 15 minutes soak. 100 μl of fresh peroxidase substrate solution was added, and an hour later the O.D. of the solution (at 450 nm) was determined.

When the above described binding assays were performed on covalently coupled monosaccharide acceptors, such as the case with Covalink NH plates, the TBS incubation solution was replaced with TBST and the wash steps were performed using high ionic strength buffer instead of TBST.

Example 10

Acceptor Immobilization—the First Step

While reducing the present invention to practice several methods for monosaccharide acceptor immobilization to microtiter plates were perfected. The Monosaccharide acceptors were bound to a microtiter plate surface via a linker and lectins or antibodies directed against the complex carbohydrates synthesized were utilized to measure binding efficiency as is further described hereinabove.

Figure 6:
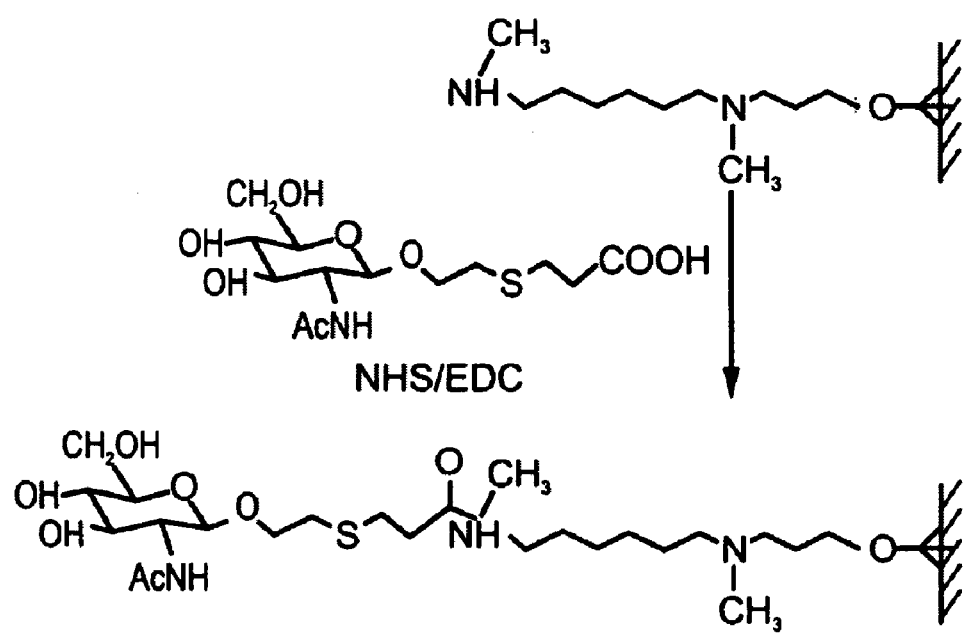
FIG. 6 depicts covalent immobilization of GlcNAc to NHS/EDC activated Covalink NH.
Figure 7A:
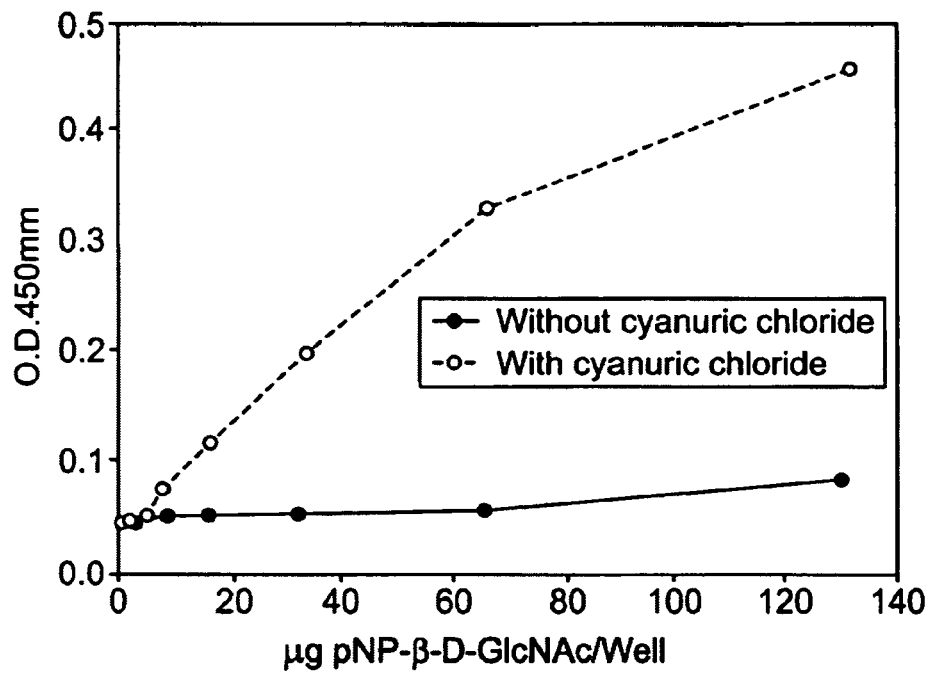
FIG. 7a is a graph depicting the binding of WGA to PNP-GlcNAc coupled to Covalink NH plates in the presence or absence of cyanuric chloride activation (one elongation cycle); binding was visualized via a WGA conjugated peroxidase as further described in the Examples section.
Figure 7B:
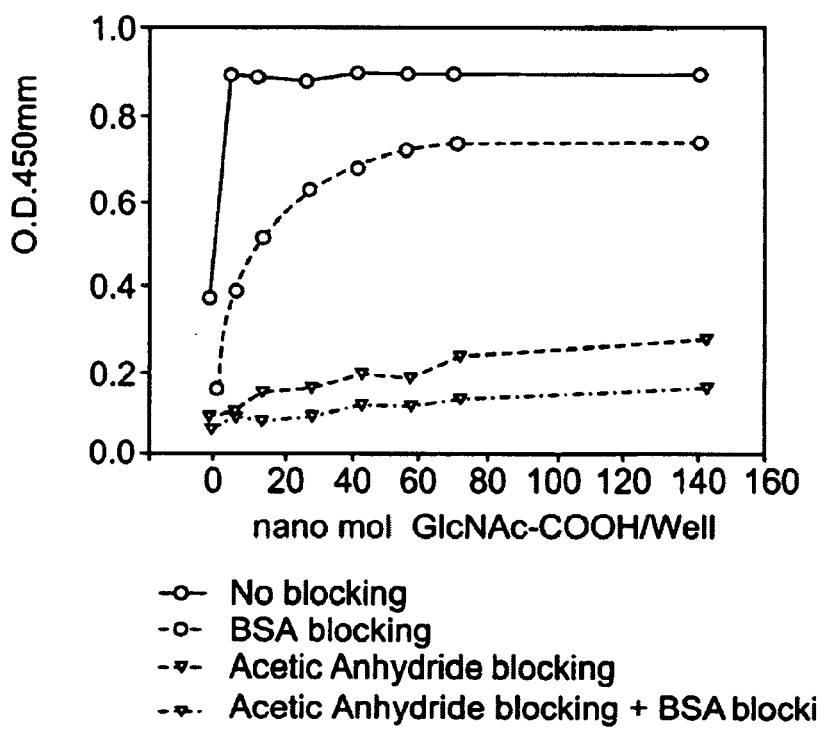
FIG. 7b is a graph depicting the effect of various blocking methods on the binding of WGA to GlcNAc-COOH coupled to Covalink NH plates; binding was visualized via a WGA conjugated peroxidase as further described in the Examples section.
Figure 7C:
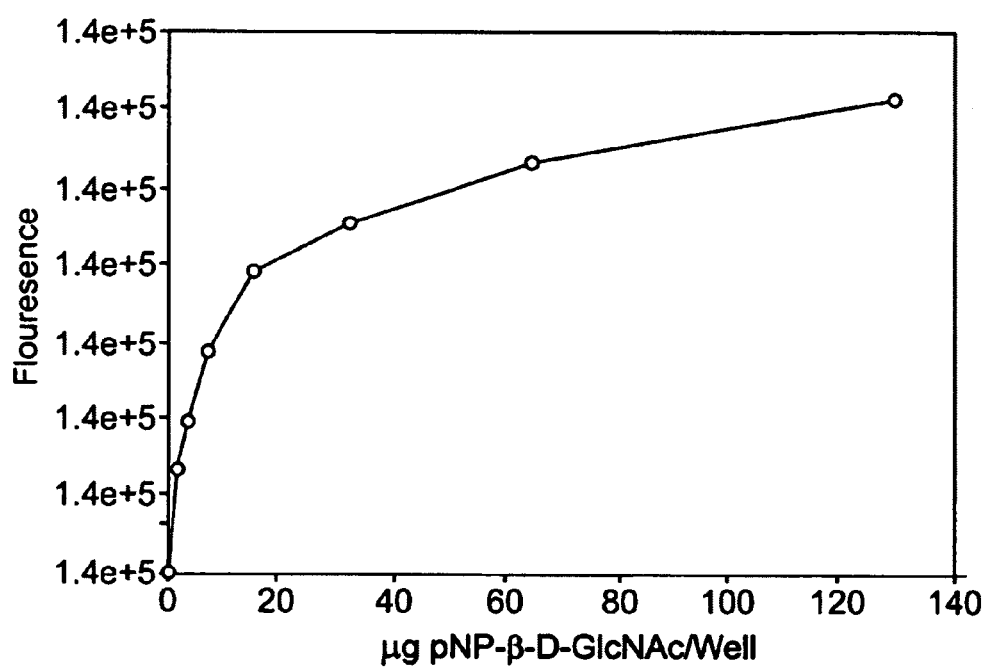
FIG. 7c is a graph depicting the binding of WGA to GlcNAc coupled to cyanuric chloride activated Covalink NH; binding was visualized via WGA conjugated FITC as further described in the Examples section.

Plate immobilization of the first monosaccharide acceptor building block was performed by either (i) adsorption of neoglycoprotein BSA-GlcNAc (β-D-GlcNAc conjugated to BSA) to the surface of a microtiter plate; or (ii) covalent immobilization using an appropriate linker. Covalent immobilization was performed using either cyanuric chloride activation (FIGS. 5a and 5b), or NHS/EDC activation (FIG. 6) of CovaLink NH plates. The use of cyanuric chloride activation enabled linker elongation of about 1.5 nanometer in each elongation cycle. The presence of the immobilized monosaccharide (GlcNAc) was measured according to lectin binding using WGA lectin conjugated to peroxidase or FITC. Binding was quantitated using either colorimetric or fluorescent signal detection as shown in FIGS. 7a–c.

Materials and Methods:

Adsorption of GlcNAc conjugated to BSA to Maxisorb plates:

A solution of 0.1 M Na$_2$CO$_3$ pH 9.6, including 0–3000 ng of BSA-GlcNAc (prepared as described by Monsigny et al., Biol. Cell, 51,187 1984) was aliquoted in 100 μl aliquots into wells of a Maxisorb microtiter plate (NUNC Cat. No. 469914) and the plate was incubated at 4° C. for 16 hours. Following incubation, the solution was removed and 200 μl of 0.1 M $Na_2CO_3$ pH 9.6 including 1% BSA was added to each well and the plate was incubated for an additional 2 hours in order to block nonspecific binding of proteins (such as enzymes or lectins) to the well surface. Following blocking, the BSA-GlcNAc solution was replaced with TBS buffer/0.2% $NaN_3$/BSA 1% and the plate was stored at 4° C.

The adsorption of BSA-GlcNAc was verified peroxidase conjugated WGA as described hereinabove.

Figure 8A:
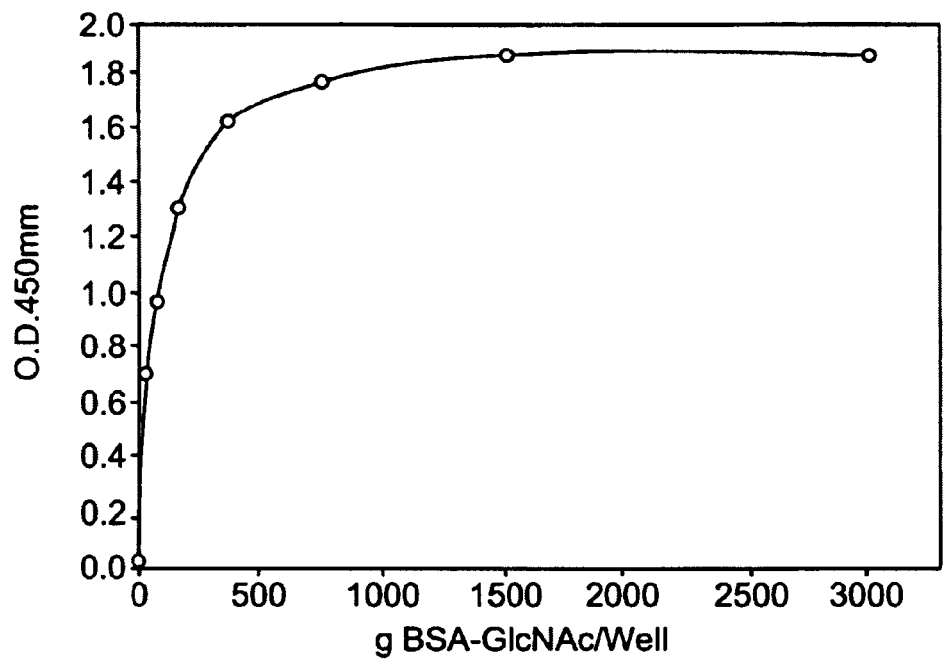
FIG. 8a is a graph depicting WGA binding to BSA-GlcNAc which coats the Maxisorb plates; binding was visualized via a WGA conjugated peroxidase as further described in the Examples section.

Results:

The surface area of a single 66 kDa BSA molecule (approximately 50 $nm^2$) is covered with approximately 25 GlcNAc groups. On a Maxisorb surface which is fully coated with BSA-GlcNAc, the average distance between adjacent GlcNAc groups is approximately 1.0 nm and the diameter of the lectin's carbohydrate recognition site is about 2 nm. Thus, in order to prevent steric interference between adjacently bound lectins or between bound lectin and other monosaccharides, the density of the immobilized monosaccharides should not exceed $10^{14}$ per $cm^2$. Since in this case, the immobilized monosaccharide forms a part of a bound protein molecule which is approximately 5 nm in diameter, the monosaccharide groups are positioned approximately 5 nanometers above the plate surface and thus are available for enzymatic elongation by the glycosyltransferase. FIG. 8a describes a saturation curve for BSA-GlcNAc bound to a Maxisorb microtiter plate.

Figure 8B:
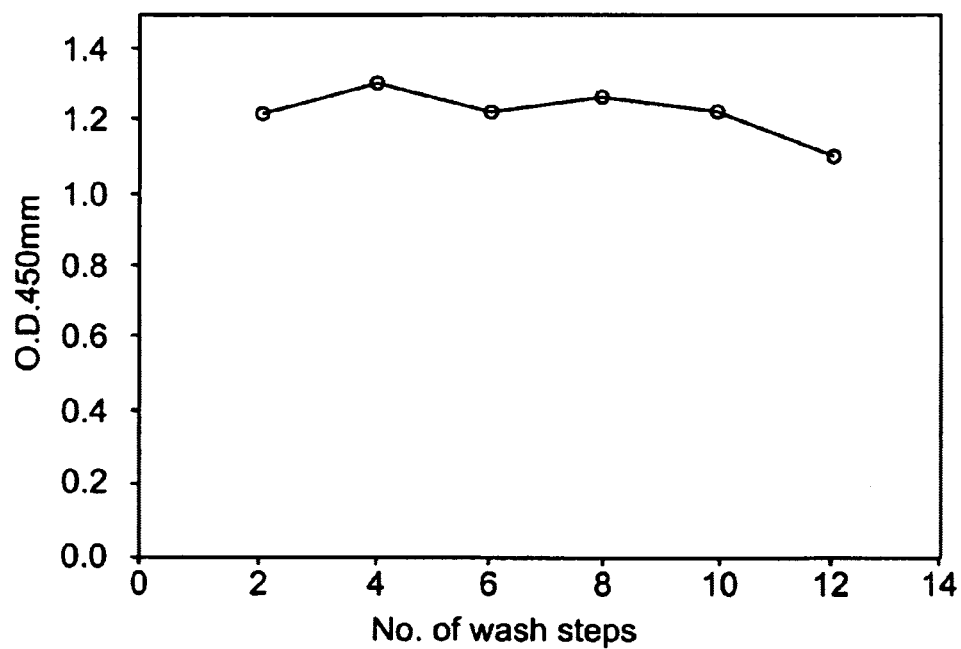
FIG. 8b is a graph depicting the binding described in FIG. 8a as a function of the number of wash steps employed.

Following BSA-GlcNAc binding, plates were washed with TBST, a buffer that contains a medium ionic strength detergent (0.15 M NaCl), in order to remove non-specifically bound lectins. This wash step does not remove the bound BSA and thus allows sequential enzymatic reactions. As shown in FIG. 8b, the bound BSA was stable throughout 12 extensive washing cycles. Following each wash step, the amount of BSA-GlcNAc (starting at 200 ng/well) was measured by WGA lectin binding as described above.

Figure 8C:
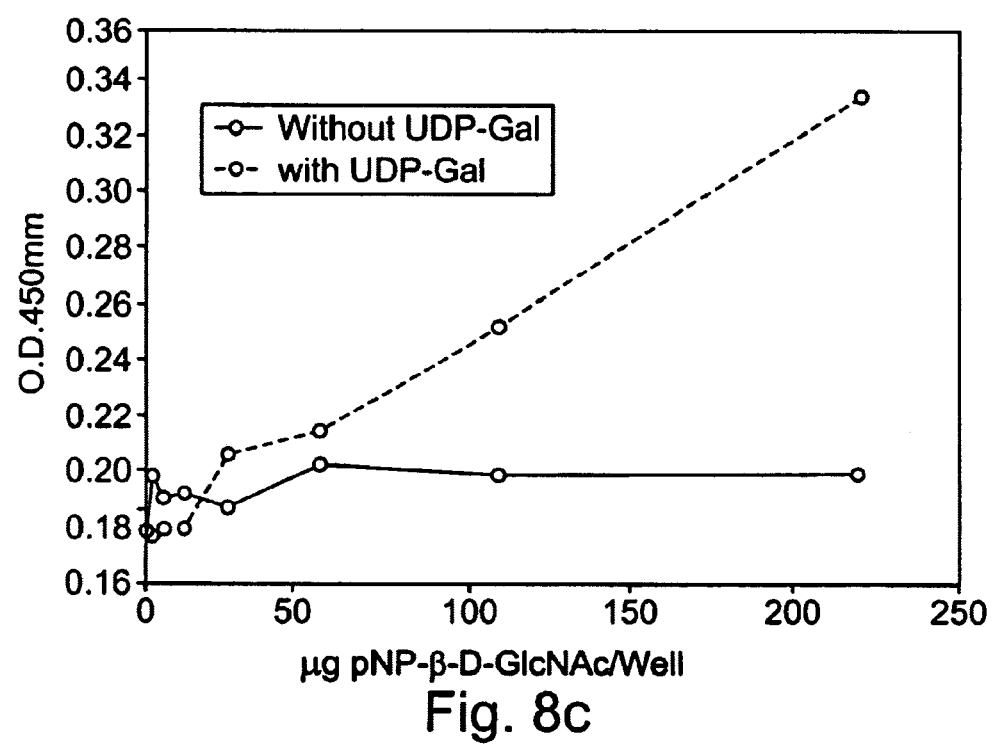
FIG. 8c is a graph depicting the transfer of β-D-Galactose to the plate immobilized phenyl-β-D-GlcNAc (22 atom linker) as verified using ECorA lectin binding.

Covalent immobilization of GlcNAc to Covalink NH, as well as the elongation of Covalink NH with 13 additional atoms in each subsequent elongation cycle was performed as shown in FIGS. 5a–b. Binding results for cyanuric chloride mediated immobilization of WGA to β-D-GlcNAc (with a single elongation cycle) or to NHS/EDC activated CovaLink NH are shown in FIGS. 7a–b. The density of the amino groups on the Covalink NH surface is $10^{14}$ per $cm^2$ and the average distance between the GlcNAc groups is 1 nm which is sufficient for lectin binding. Following incubation with reaction mixture D7 (β1,4 galactosyltransferase, described in FIG. 8c), the transfer of β-D-galactose to the plate immobilized phenyl-β-D-GlcNAc (22 atom linker) is verified using ECorA lectin binding assay as described above. The transfer of β-D-galactose to the plate immobilized β-D-GlcNAc (NHS/EDC activated plate with a 20 atom linker) was not detected. This might be due to differences in linker length.

The above described covalent immobilization methods enable the use of a very high ionic strength buffer (e.g., 6 M Guanidine HCl or 100 mM NaOH) in subsequent washing steps thus allowing accurate "in situ" verification of each enzymatic step utilized by the process.

The removal of nonspecifically bound molecules is crucial for accurate library synthesis. Since glycosyltransferases are glycoproteins with complex carbohydrates presented on their outer surface, nonspecific adsorption of the enzyme may interfere with, or generate errors in, the synthesis. Lectins and antibodies are also glycoproteins and as such non-specific binding thereof may lead to inaccurate structural prediction. The standard blocking agent commonly used in enzymatic reactions, is nonfat milk. Since nonfat milk contains many glycoconjugated proteins it is not suitable for enzymatic synthesis of complex carbohydrates. Instead, synthesis reactions performed according to the present invention utilized BSA as a blocking agent since it is non-glycosylated. As shown by FIG. 7b, while chemical blocking agents interfered with lectin binding, blocking with BSA enabled specific lectin binding while substantially reducing non-specific binding. During practice, it was realized that since cyanuric chloride activated amino groups hydrolyze spontaneously in water there is no need for further blocking when using this plate coupling procedure.

Example 11

Library Synthesis

High yield is critical to an iterative solid phase enzymatic synthesis. Since glycosyltransferases catalyze the transfer of a sugar moiety from an activated nucleotide phosphate sugar donor to an appropriate acceptor, degradation of the phosphodiester energetic bond of the nucleotide sugar is irreversible. As such, there is no theoretical obstacle hindering the completion of the synthesis reactions. Preferably, the nucleotide sugar concentration of the reaction should be approximately 10 to 20 fold higher than a $K_m$ value of the enzyme to the donor, which ranges from several to several hundred millimolars. In a single microtiter plate well which contains approximately 100 μl of solution, 0.2 nanomoles of well-bound saccharide groups are available for the enzymatic reaction. As such, a nucleotide sugar concentration equal to or greater than 1 millimolar is sufficient.

Materials and Methods:

NHS/EDC activation and coupling of β-D-GlcNAc: 50 μl aliquots of a 2-(2-carboxyethylthio)-ethyl 2-β-D-GlcNAc (NNI SS-01-003) solution were dispensed onto CovaLink NH strips and the strips were incubated in wells containing 50 μl of a solution including 3 mg/ml of 1-Ethyl-3-(3dimethylaminopropyl)-carbodiimide (EDC) (Sigma E-7750) and 3 mg/ml of N-hydroxysuccinimide (NHS) (Sigma H-7377). The wells were sealed and the plates were shaken at 50 RPM at 37° C. for 24 hours. The wells were washed three times with distilled water and the unreacted amino groups in the wells were blocked for 2 hours in 300 ml of a solution containing methanol/aceticanhydride/water (85/10/5 V/V/V, respectively). Following four washes with distilled water the plates were air dried and incubated for 12 hours with a blocking solution which included 1% BSA in PBS.

Synthesis of a Cleavable Linker, Coupling the First Monosaccharide thereto, and Cleaving the Linker:

Cyanuric chloride activation: A solution containing 48 mg of cyanuric chloride (Aldrich, Cat. No. C95501) dissolved in 3 ml of acetone was added, while stirring, to 45 ml of 0.1 M phosphate buffer. An aliquot (200 μl) of this solution was quickly added (within 2 minutes) to each well of a Covalink NH plate. The plate was incubated at room temperature for 5 minutes following which the solution was discarded and the plate washed three times with double distilled water and dried at 50° C. for 30 minutes.

Amino linker elongation cycle: 100 μl of a 1,8-diamino 3,6 (MERCK 818116) solution (3 ml in 50 ml 0.1 M carbonate buffer pH 9.6) or 1,8 diaminooctane (ALDRICH D2, 240-1) solution (100 mg per ml 0.1 M carbonate buffer pH 9.6) was added to each well of a cyanuric chloride activated plate. The wells were sealed and the plate was incubated at 25° C. for 12 hours. Following incubation, the wells were washed four times with water and the plate was cyanuric chloride activated as described above. Three elongation cycles of 1,8-diamino 3,6 dioxaoctane were executed until the desired linker length was achieved.

Coupling of p-nitrophenyl-β-D-GlcNAc (first monosaccharide building block): GlcNAc monosaccharide molecules were linked to the activated plates described above. The following procedure was utilized to effect linking: a solution containing 60 mg/ml sodium dithionite in 0.1 M sodium carbonate was added to each well of rows B–H of the plate. A 200 μl aliquot of a second solution containing 20 mg of p-nitrophenyl-N-acetyl-β-D-GlcNAc (Calbiochem Cat. No. 487052) and 200 mg of sodium dithionite (Fluka Cat. No. 71700) which were dissolved in 6 ml of double distilled water and titrated to a pH of 7.5 using 3 ml of 0.1 M sodium carbonate (pH 9.6) was serially diluted two folds from rows A to H. The wells were sealed and incubated at room temperature overnight. Following incubation, the wells were washed four times with double distilled water and then three with methanol (200 μl/well), the third wash including a 15 minutes soak at room temperature. The methanol was discarded, and the plates were air dried and stored at 4° C.

Coupling of Squaric acid derivative of β-D-GlcNAc (first monosaccharide building block): GlcNAc-Squaric acid derivative was prepared as follows: A solution of 100 mg D-GlcNAc (Calbiochem 346299), 31.25 mg ammonium bicarbonate (Merck 1.05426.1000) in 1.9 ml of ammonia was incubated at 35° C. for 24 hours. The solution was concentrated in a vacuum centrifuge, water was added and the solution re-concentrated to 0.45 ml. To this solution 72 μl of squaric acid (Across Orgencis 30508-0010), 1.6 ml ethanol, 1.6 ml of 0.1 M $Na_2CO_3$, pH 9.6, were added. The resulting solution was incubated for 3 hours at 25° C. and concentrated in a vacuum centrifuge to eliminate the ethanol. The coupling of GlcNAc-Squaric acid derivative was affected by incubation of 100 μl of GlcNAc-Squaric acid derivative (10 μmol) in 1 ml of 0.1M $Na_2CO_3$, pH 9.6, with an elongated amine linker (FIG. 5b) for 2 hours followed by washing with methanol. This was performed in each well of a microtiter plate. Following enzymatic synthesis of carbohydrates the linker can be cleaved by incubation with aqueous solution of bromine (0.3 mmol bromine in 4 ml water) for 30 minutes, and the removed glycan can be transformed to a reducing sugar by the addition of 15 μl of 0.2 M aquenuse sodium borate (see below).

Binding of WGA to covalently coupled β-D-GlcNAc: The presence of covalently bound β-D-GlcNAc was verified by binding of WGA conjugated to peroxidase or fluoresceine-iso-thio-cyanate (FITC). Detection was performed as follows: 100 μl of 5 μg/ml of peroxidase (SIGMA L-3892, 150 peroxidase units per mg protein) or FITC (SIGMA L-4895) conjugated WGA prepared in TBST including 10 millimolar of $MnCl_2$ and of $CaCl_2$ was incubated in each well at 25° C. for one hour. The wells were washed three times with 200 μl high ionic strength washing solution, with the last wash consisting of a 15 minutes soak. To develop the peroxidase labeled WGA, 100 μl of fresh peroxidase substrate solution was added and an hour later an O.D. at 450 nm was measured. The FITC conjugated WGA bound to the β-D-GlcNAc-white Covalink NH strips (NUNC 453690) was excited (485 nm) and the fluorescence emission therefrom was measured (520 nm).

Transferring of β1,4 galactose to covalently bound β-D-GlcNAc: 100 μl of 50 mM MOPS pH 7.4 (SIGMA M-9027), 0.2% Triton CF 32 (Sigma), 20 mM $MnCl_2$ (SIGMA M-9522), 0.5 mg/ml UDP-Gal (Calbiochem 670111) and 20 milliunits/ml of a recombinant β1,4-galactosyltransferase (Calbiochem 345650) were added to each well of a plate coupled with β-D-GlcNAc. The plate was shaken at 50 RPM at 37° C. for 12 hours. Following incubation the reaction mixture was removed and the wells were washed three times with 200 μl of high ionic strength washing buffer, the last wash consisting of a 15 minutes soak. The transfer of β1,4-galactose was detected via biotin conjugated lectin (*Erythourina corallodenron* ECorA) as follows: an aliquot including of 20 μg/ml ECorA conjugated to biotin (SIGMA L-0893, 5 moles of biotin per mole protein) prepared in TBST including 10 millimolar of $MnCl_2$ and of $CaCl_2$ was added to each well and the plate was incubated for one hour at 25° C. The wells were washed 3 times with 200 μl of high ionic strength washing buffer, the last wash consisting of a 15 minutes soak. Following incubation with 100 ml of avidin conjugated to peroxidase (5 μg/ml in TBST) the wells were washed 3 times with 200 μl of high ionic strength washing buffer, the last wash consisting of a 15 minutes soak. To detect binding, 100 μl of fresh peroxidase substrate solution was added and an hour later, an O.D. at 450 nm was measured.

Measuring the kinetics of β1,4 Galactosyltransferase (D7) in solid phase: The enzymatic reaction mixture is as described for D7 with the exception that in this case 3.9 milliunits/ml of β1,4-Galactosyltransferase were utilized. The solid phase consisted of Maxisorb plates coated with 3 μg/well of BSA-GlcNAc. The enzyme mixture was added to each well at 10 minutes intervals. The wells were then washed with TBST three times and the binding of $RCA_{120}$ was measured as described above.

Figure 13:
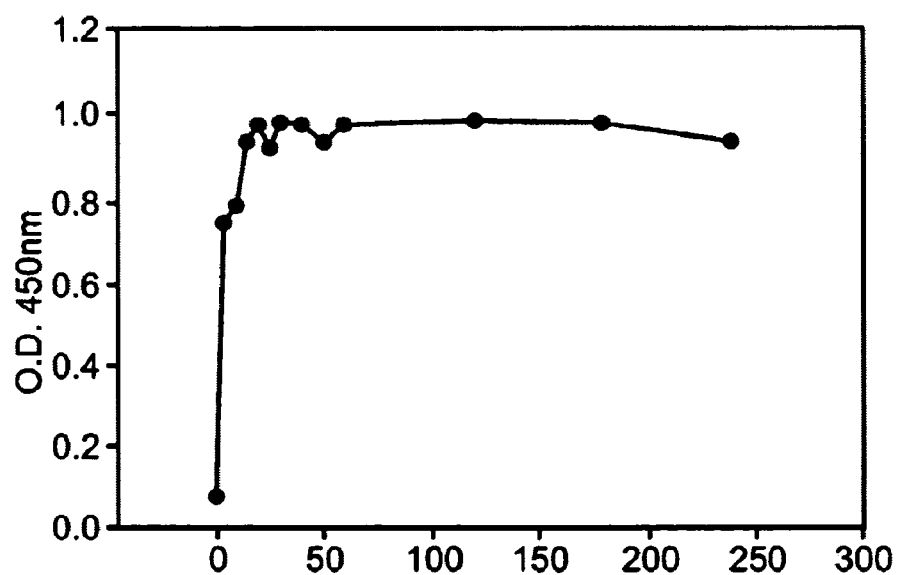
FIG. 13 is a graph depicting the reduction in binding of WGA/FITC to GlcNAc attached to wells of a microtiter plate following the cleavage of the linker.

Linker Cleavage: The above described linker is cleavable by bromine. Linker cleavage was therefore effected by the addition of 100 μl aqueous solution of bromine (0.3 mmol bromine in 4 ml water) into the wells and incubation for a time period of 60 minutes, followed by washing of the wells three times with TBST. To this end, 100 μl of 0.5 μg/ml WGA/FITC in TBST was added to each well. Following one hour incubation, the wells were washed three times with a high salt buffer and fluorescence was measured (Excitation—485 nm; Emission—520 nm). FIG. 13 shows the reduction in binding of WGA/FITC to GlcNAc following the above procedure.

Figure 12:
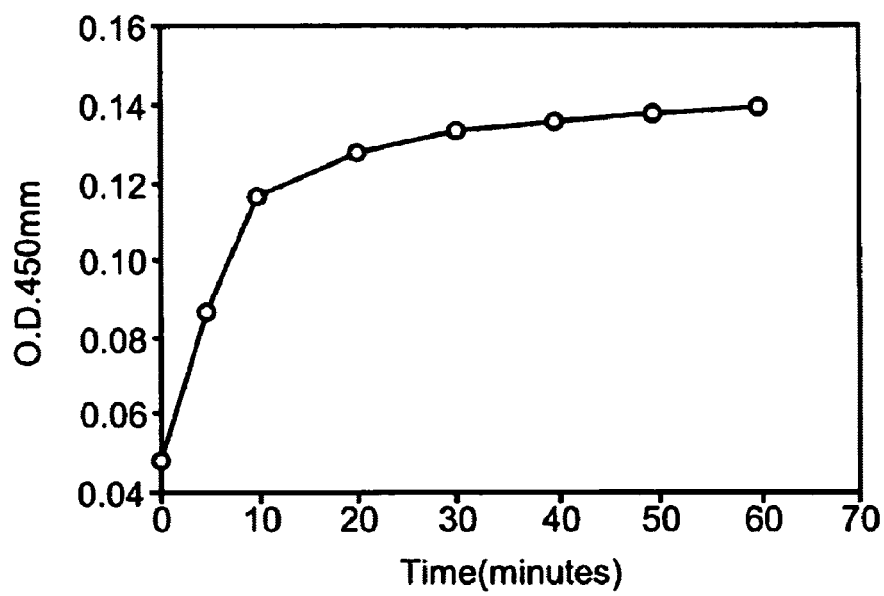
FIG. 12 is a graph depicting the binding of $RCA_{120}$ to BSA-GlcNAc bound to Maxisorb plates at various time points following incubation with a β1,4 galactosyltransferase reaction mixture (D7).

Results:

Results obtained while reducing the present invention to practice indicate that a solid phase reaction is slower than a liquid phase reaction. As shown in FIG. 12, enzymatic transfer of galactose to 0.5 nanomole of bound GlcNAc using 0.5 mU of β-1,4 galactosyltransferase takes approximately an hour to complete, as compared to approximately one minute it takes to complete the same reaction in solution. Therefore, to achieve maximum yield, 0.5 milliunits of each enzyme were employed for 3–4 hours.

Nucleotide phosphates (UDP, CMP, GDP) which result from the break down of nucleotide sugar are by-products of these enzymatic reactions. It was observed that these by-products inhibit glycosyltransferase activity. As such, an addition of a phosphatase to degrade the released nucleotide phosphate(s) can substantially increase the rate of the solid phase reaction.

Linker length, flexibility of the complex carbohydrate, immobilization of carbohydrate groups and steric hindrance are also important factors effecting synthesis efficiency. As uncovered by experimentation conducted as part of the present study, a neoglycoprotein coated Maxisorb surface can be efficiently utilized to immobilize the first monosaccharide, obtain the glycosyltransferase enzymatic reaction and avoid steric hindrance problems. An elongated covalent linker based on cyanuric acid and p-Nitro phenyl enables coupling of the first monosaccharide to a 2–8 nanometer linker thus avoiding steric hindrance when the first monosaccharide is covalently bound to the surface and obtain the glycosyltransferase enzymatic reaction.

The reduction in fluorescence following incubation with bromine indicates the cleavage of the linker. The ability to cleave the linker and remove the glycan after the sequential synthesis is crucial for structural analysis and verification of the synthesized oligosaccharide by, for example, mass spectroscopy or high performance liquid chromatography.

Example 12

Library 1

Figure 9:
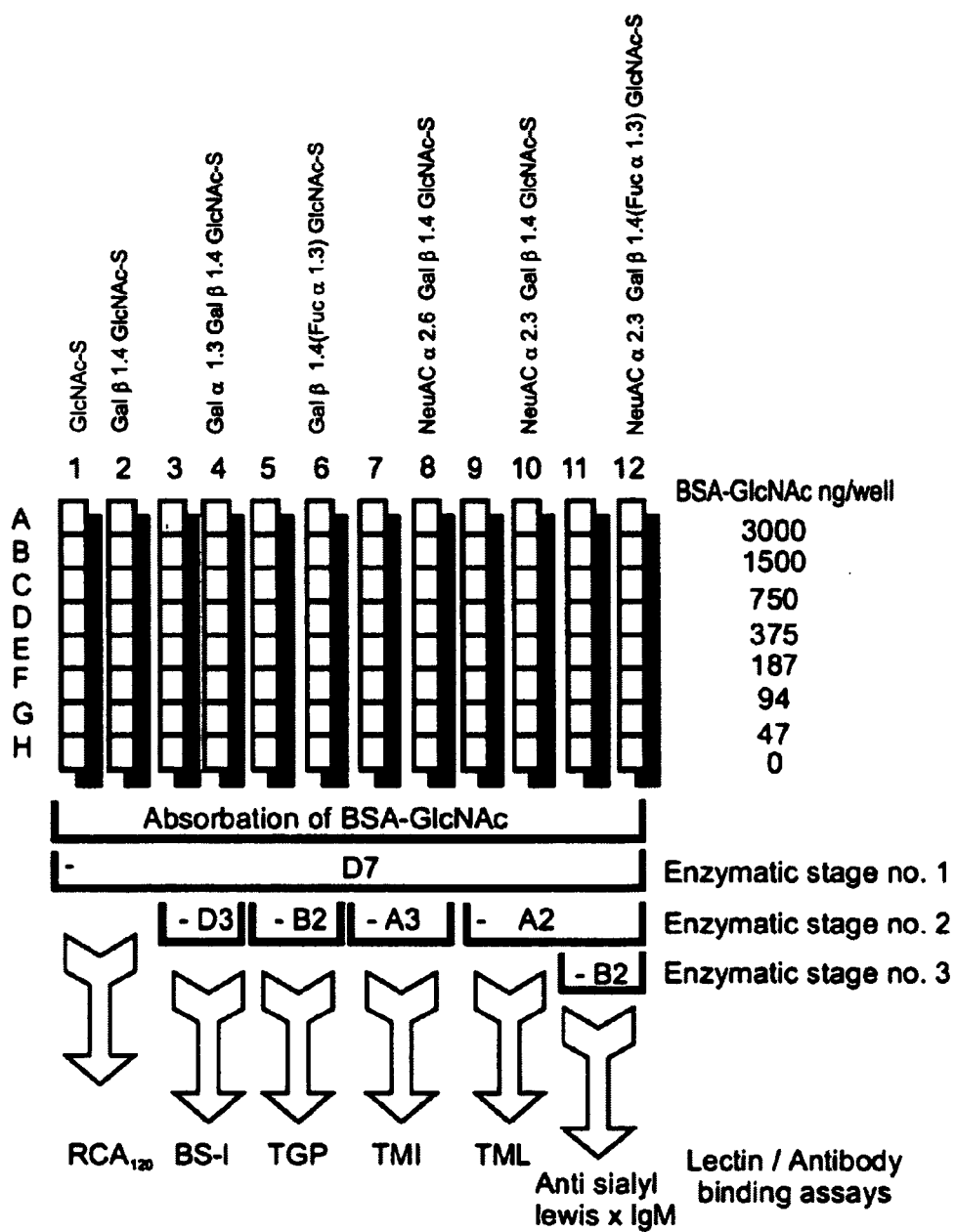
FIG. 9 depicts the enzymatic steps required for the synthesis of a library consisting of the structures described in Table 17 immobilized to a plate, outlining the organization of the microtiter plate, the enzymatic reactions performed at each step and the lectins/antibody binding assays.

FIG. 9 describes the enzymatic steps required for the synthesis of a library consisting of the structures described in Table 17 immobilized to a plate, outlining the organization of the microtiter plate, the enzymatic reactions performed at each step and the lectins/antibody binding assays. Each enzymatic step is verified against a control strip which does not contain the added nucleotide sugar.

A different set of enzymatic reactions (described in detail hereinabove) were performed in each strip in accordance with the procedures developed by the present invention. The Tables below describe in detail the various reactions and components utilized in order to generate this library. Table 16 summarizes the enzymatic reactions used to synthesize the first library, Table 17 describes the enzymatic modules (EM's, further described in Examples 1–9), the complex carbohydrate structures formed and the lectin/antibody binding assays performed for each strip, while Table 18 describes the lectins/antibodies binding assays that were used to verify the complex carbohydrate structure formed following each enzymatic step.

TABLE 16

Enzymatic reactions utilized in the synthesis of the first library (donors, acceptors and indexes)

| index | extension | α/β | Pos. | acceptor | donor | Enzyme Cat. No. | E.C. |
|---|---|---|---|---|---|---|---|
| A2 | | α | 3 | D-Gal-β(1,4)-D-GlcNAc-R | CMP-NeuAC | Calbiochem 56621 | 2.4.99.6 |
| A3 | | α | 6 | D-Gal-β(1,4)-D-GlcNAc-R | CMP-NeuAC | Calbiochem 56622 | 2.4.99.1 |
| B2 | D-Gal-β(1,4) | α | 3 | D-GlcNAc-R | GDP-L-Fuc | Calbiochem 34432 | 2.4.1.152 |
| D3 | | α | 3 | D-Gal-β(1,4)-D-GlcNAc-R | UDP-Gal | Calbiochem 34564 | 2.4.1.151 |
| D7 | | β | 4 | D-GlcNAc-R | UDP-Gal | Calbiochem 34565 | 2.4.1.38 |

TABLE 17

EMs List

| EM | First Immobilized Monosaccharide | ERs sequence | Structure Formula | Lectin/Antibody Binding Assays |
|---|---|---|---|---|
| 1 | GlcNAc-S | D7 | Gal β 1,4 GlcNAc-S | RCA120+ |
| 2 | GlcNAc-S | D7, A2 | NeuAC α 2,3 Gal β 1,4 GlcNAc-S | TML+, RCA120− |
| 3 | GlcNAc-S | D7, A3 | NeuAC α 2,6 Gal β 1,4 GlcNAc-S | TML+, RCA120− |
| 4 | GlcNAc-S | D7, D3 | Gal α 1,3 Gal β 1,4 GlcNAc-S | BS-I+, RCA120− |
| 5 | GlcNAc-S | D7. B2 | Gal β 1,4 (Fuc α 1,3)GlcNAc-S | TGP+ |
| 6 | GlcNAc-S | D7, A2, B2 | NeuAC α 2,3 Gal β 1,4 (Fuc α 1,3)GlcNAc | IgM Anti-Sialyl Lewis X+ |

TABLE 18

Lectin/Antibody binding assays

| Name | Type of Molecule | Specificity | Cat. No. | Source | Labeling |
|---|---|---|---|---|---|
| WGA | Lectin | GlcNAc | Sigma L-3892 | *Tritcum vulgaris* | Peroxidase/FITC |
| RCA120 | Lectin | β-Gal | Sigma L-2758 | *Ricinus communis* | Peroxidase |
| BS-I | Lectin | α-Gal, α-GalNAc | Sigma L-3759 | *Bandeiraea Simplicifolia* | Biotin |
| TGP | Lectin | α-Fuc | Sigma L-1508 | *Tereagonolobus purpureas* | Peroxidase |
| TML | Lectin | Sialic acid | Calbio. 431803 | *Tritrichomonas mobilensis* | Biotin |
| Anti-Sialyl Lewis X | IgM | Sialyl Lewis X | Calbio. 565953 | Mouse | Goat anti mouse/Peroxidase |

Figure 10A:
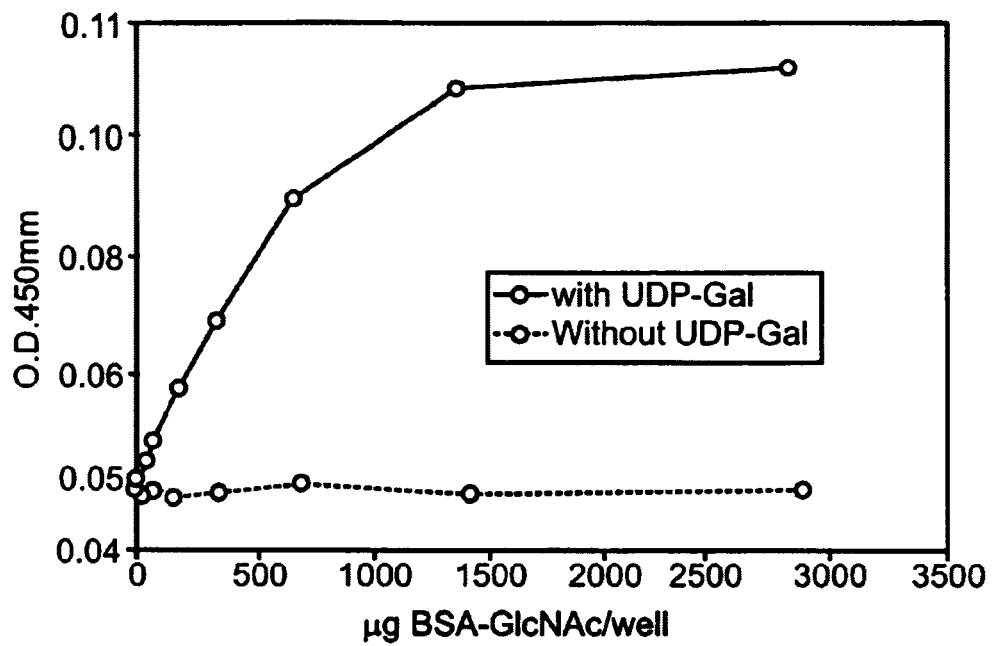
FIG. 10a is a graph depicting $RCA_{120}$ binding following incubation with αβ1,4 galactosyltransferase reaction mixture (D7) (solid line) or following a control reaction (hatched line).
Figure 10B:
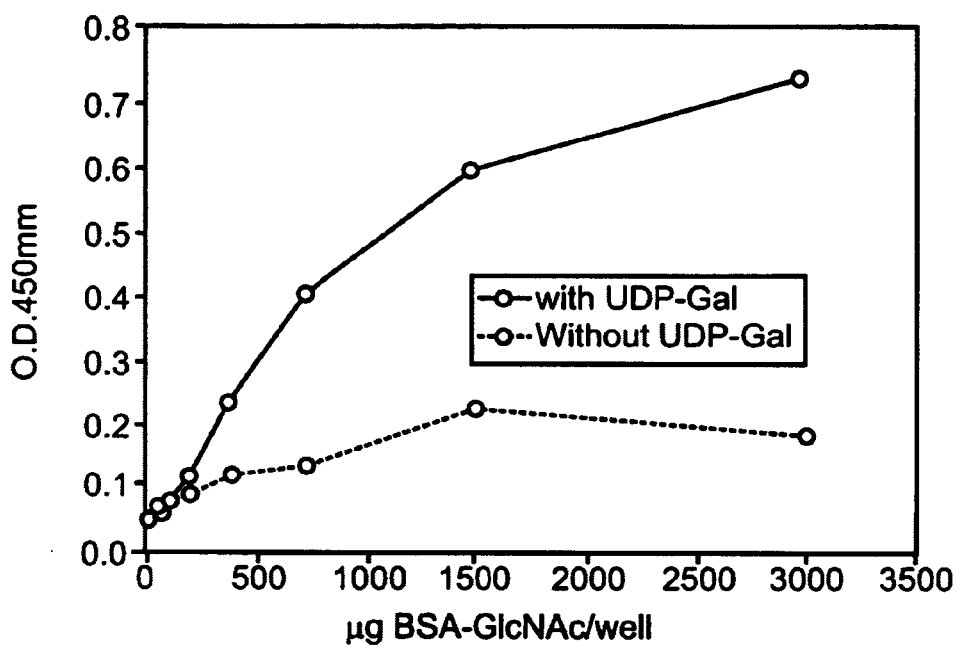
FIG. 10b is a graph depicting BS-1 binding following incubation with a α1,3 galactosyltransferase reaction mixture (D3) (solid line) or following a control reaction (hatched line).
Figure 10C:
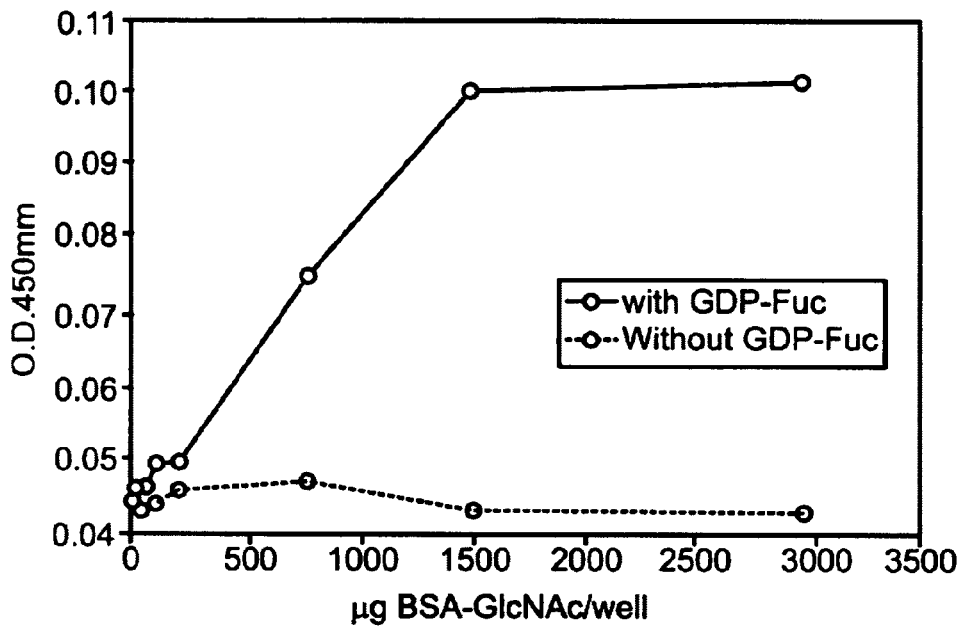
FIG. 10c is a graph depicting TGP binding following incubation with a α1,3 fucosyltransferase VI reaction mixture (B2) (solid line) or following a control reaction (hatched line).
Figure 10D:
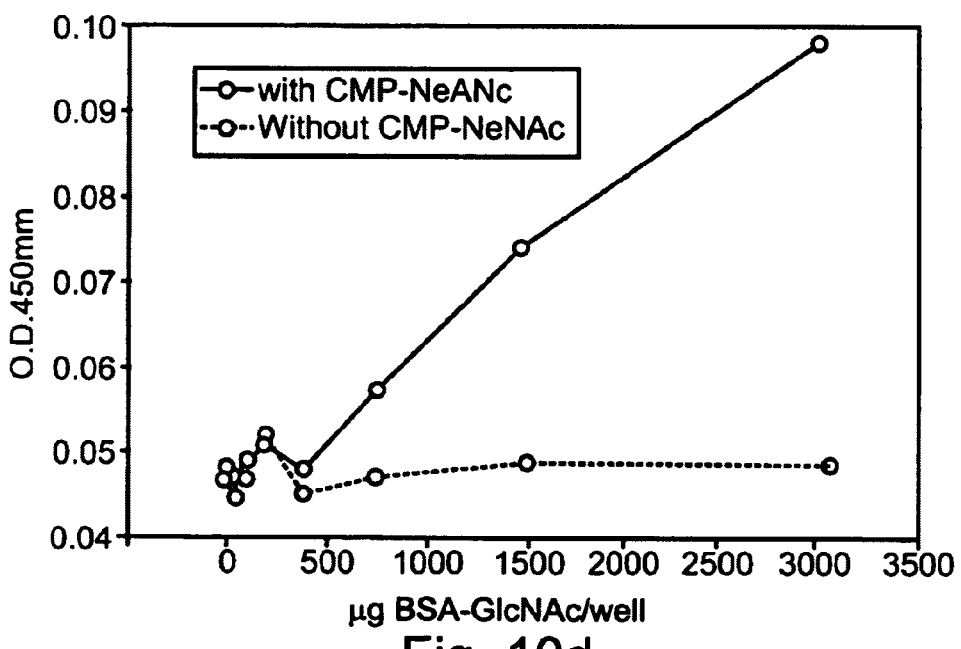
FIG. 10d is a graph depicting TML binding following incubation with an β2,6 sialyltransferase reaction mixture (A2) (solid line) or following a control reaction (hatched line).
Figure 10E:
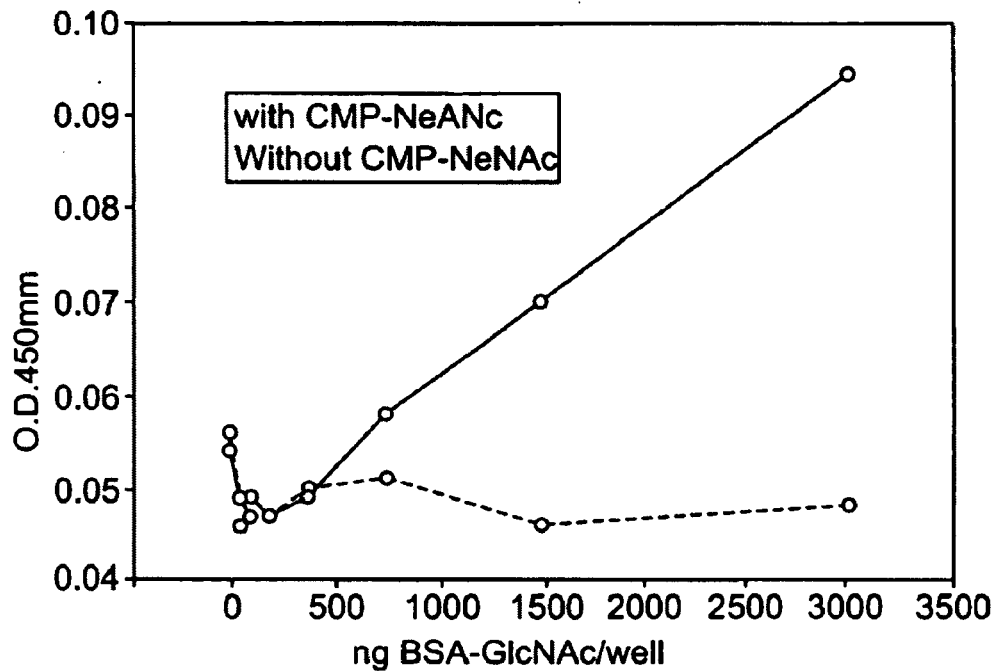
FIG. 10e is a graph depicting TML binding following incubation with a α2,3 sialyltransferase reaction mixture (A3) (solid line) or following a control reaction (hatched line).
Figure 10F:
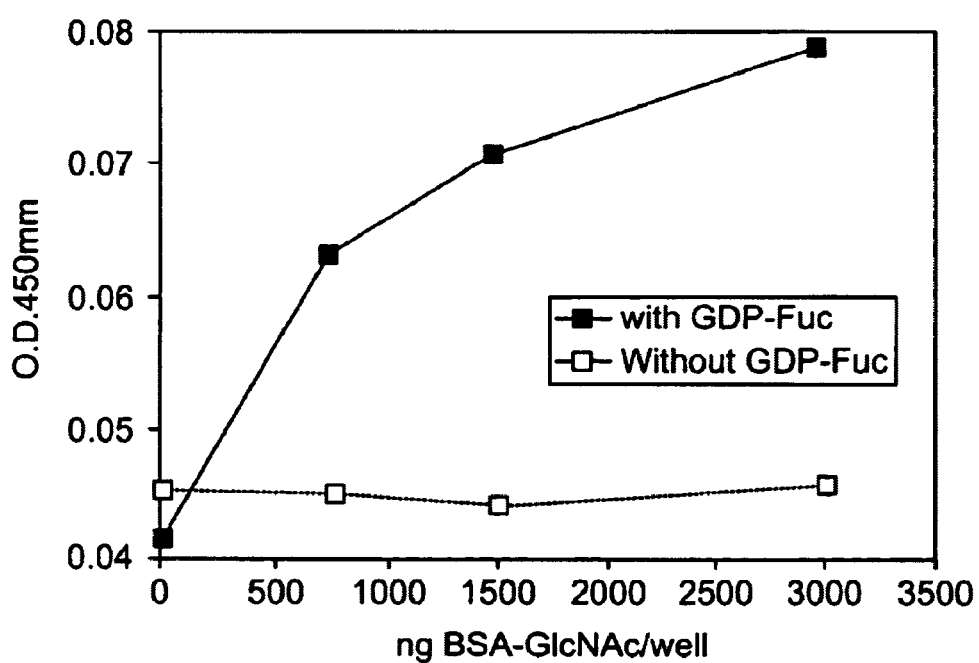
FIG. 10f is a graph depicting Anti-sialyl Lewis X mouse IgM binding following incubation with facosyltransferase VI reaction mixture (B2) (solid line) or following a control reaction (hatched line).

Results:

FIGS. 10a–f describe the lectins/antibodies binding assays performed on each strip following each enzymatic reaction. The increase in binding of $RCA_{120}$ (FIG. 10a) indicates transfer of β-D-Galactose to GlcNAc and formation of a stable β-1,4 glycosidic bond. The efficiency of the second enzymatic step was verified via an increase in BS-I binding (FIG. 10b) which is indicative of a transfer of α-D-Galactose to Gal β-1,4 GlcNAc and formation of stable α-1,3 glycosidic bond therebetween. The increase in TGP binding (FIG. 10c) is indicative of a transfer of α-L-fucose to Gal β-1,4 GlcNAc and formation of a stable α-1,3 glycosidic bond therebetween. The branched oligosaccharide formed by this reaction is a Lewis X antigen. As shown by FIGS. 10d–e an increase in TML binding indicates a transfer of α-D-NeuAC to Gal β-1,4 GlcNAc forming a stable α-2,6—2,3 glycosidic bond therebetween. The increase in anti sialyl Lewis X IgM binding (FIG. 10f) indicates a transfer of α-L-fucose to NeuAC α-2,3 Gal β-1,4 GlcNAc forming a stable α-1,3 glycosidic and generating Sialyl Lewis X antigen composed of four different monosaccharides.

Example 13

Library 2

Figure 11:
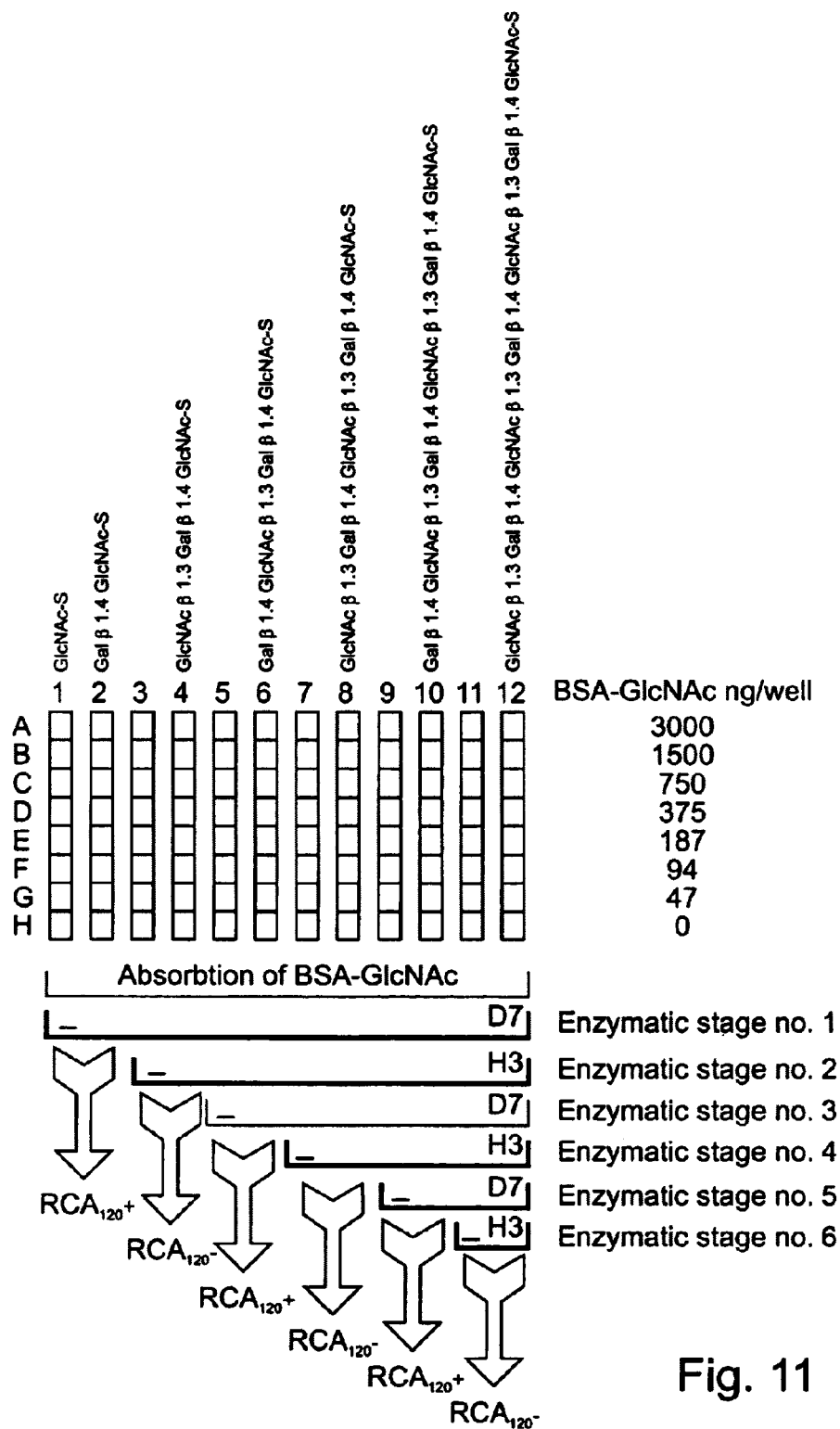
FIG. 11 depicts the enzymatic reactions performed in each step of a library (referred to as library 2) synthesis and the lectins binding assays that were used to verify the efficiency of the various enzymatic steps.

The following library exemplifies the ability of the synthesis method of the present invention to synthesize poly N-acetyllactose amine type II chain of different lengths. FIG. 11 describes the organization of the microtiter plate, the enzymatic reactions to be performed in each step and the lectins binding assays that can be used to verify the efficiency of the various enzymatic steps. Each enzymatic step is verified against a control strip which does not contain the added nucleotide sugar. Each strip is subjected to a different set of enzymatic reactions (Enzymatic Module-EM) which are performed according to the procedures developed by the present invention.

Table 19 describe the enzymatic reaction mixes and conditions (described in detail hereinabove) that are used for synthesis of Poly N-acetyllactoseamine library in accordance with the teachings of the present invention. Table 20 describes the Enzymatic Modules (EM's) and the complex carbohydrate structures. $RCA_{120}$ binding assay is performed after each enzymatic step as described above to evaluate the addition of Galactose ($RCA_{120}$ binding) or GlcNAc (disappearance of $RCA_{120}$ binding) to the elongating poly N-acetyllactoseaminide chain.

TABLE 19

A list of Enzymatic Reactions used for synthesis of Poly N-acetyllactoseaminide library (donors, acceptors and indexes)

| index | extension | α/β | Pos. | acceptor | donor | Enzymes Cat. No. | E.C. |
|---|---|---|---|---|---|---|---|
| D7 | | β | 4 | D-GlcNAc-R | UDP-Gal | Calbiochem 345650 | 2.4.1.38 |
| H3 | | β | 3 | D-Gal-β(1,4)-D-GlcNAc-R | UDP-GlcNAc | Zhou et al., Proc. Natl. Acad. Sci. U.S.A. Vol. 96 pp. 406–411 | |

TABLE 20

EM List

| EM | ERs sequence | Structure Formula | RCA120 Binding Assays |
|---|---|---|---|
| 1 | D7, H3 | GlcNAc β 1,3 Gal β 1,4 GlcNAc-S | RCA120− |
| 2 | D7, H3, D7 | Gal β 1,4 GlcNAc β 1,3 Gal β 1,4 GlcNAc-S | RCA120+ |
| 3 | D7, H3, D7, H3 | GlcNAc β 1,3 Gal β 1,4 GlcNAc β 1,3 Gal β 1,4 GlcNAc-S | RCA120− |
| 4 | D7, H3, D7, H3, D7 | Gal β 1,4 GlcNAc β 1,3 Gal β 1,4 GlcNAc β 1,3 Gal β 1,4 GlcNAc-S | RCA120+ |
| 5 | D7, H3, D7, H3, D7, H3 | GlcNAc β 1,3 Gal β 1,4 GlcNAc β 1,3 Gal β 1,4 GlcNAc β 1,3 Gal β 1,4 GlcNAc-S | RCA120− |
| 6 | D7, H3, D7, H3, D7, H3, D7 | Gal β 1,4 GlcNAc β 1,3 Gal β 1,4 GlcNAc β 1,3 Gal β 1,4 GlcNAc β 1,3 Gal β 1,4 GlcNAc-S | RCA120+ |

Example 14

Library 3

The following library exemplifies the ability of the synthesis method of the present invention to synthesize poly N-acetyllactose amine type II chain of different lengths and modifications. This library include oligosaccharide structures with two branches. The first monosaccharide is bound to the surface via BSA. Table 21 describes the enzymatic reactions that are utilized for the synthesis, while Table 22 describes the enzymatic modules (EM's) utilized and the complex carbohydrate structures formed thereby. To verify the accuracy of the sequential enzymatic synthesis, the oligosaccharide bound to the well is released using a protease and subjected to analysis using HPLC, methylation analysis or MALD-TOF-MS (Rudd, P. M. Dwek, R. A. (1997) Current Opinion in biotechnology 8 488–497).

TABLE 21

Enzymatic reactions utilized in the synthesis of library 3

| index | extension | α/β | Pos. | acceptor | donor | Enzymes Cat. No. | E.C. |
|---|---|---|---|---|---|---|---|
| D7 | | β | 4 | D-GlcNAc-R | UDP-Gal | Calbiochem 345650 | 2.4.1.38 |
| A2 | | α | 3 | D-Gal-β(1,4)-D-GlcNAc-R | CMP-NeuAC | Calbiochem 566218 | 2.4.99.6 |
| B2 | D-Gal-β(1,4) | α | 3 | D-GlcNAc-R | GDP-L-Fuc | Calbiochem 344323 | 2.4.1.152 |
| H3 | | β | 3 | D-Gal-β(1,4)-D-GlcNAc-R | UDP-GlcNAc | Zhou et al., Proc. Natl. Acad. Sci. U.S.A. Vol. 96 pp. 406–411 | |

TABLE 22

EM List

| EM | ERs sequence | Structure Formula |
|---|---|---|
| 1 | D7, H3, D7, B2 | Gal β 1,4 (Fuc α 1,3) GlcNAc β 1,3 Gal β 1,4 (Fuc α 1,3) GlcNAc-S |
| 2 | D7, H3, D7, A2, B2 | NeuAC α 2,3 Gal β 1,4 (Fuc α 1,3) GlcNAc β 1,3 Gal β 1,4 (Fuc α 1,3) GlcNAc-S |

Thus, the present invention provides an efficient and accurate method for a solid phase synthesis of complex carbohydrates of branched or unbranched structures.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

References

1. Arya, P. and Ben, R. N. (1997) *Angew. Chem. Int. Ed. Engl.* 36 1280–1282.
2. Ashardy, E., Atherton, E., Gait, M. J. Lee, K. and Sheppard, R. C. (1979) *J. Chem. Soc. Chem. Commun.* 423–425.
3. Atherton, E. and Sheppard, R. C. (1989) in *Solid phase peptide synthesis: A practical approach*, IRL: Oxford.
4. Bayer, E. (1991) *Angew. Chem. Int. Ed. Engl.* 30 113–129.
5. Bergh, M. L. and van den Eijnden, D. H. (1983) *Eur. J. Biochem.* 136 113–8.
6. Bierhuizen, M. F., Mattei, M. G. and Fukuda, M. (1993) *Genes Dev.* 7 468–478.
7. Bierhuizen, M. F. and Fukuda, M. (1992) *Proc. Natl. Acad. Sci. USA* 89 9326–9330.
8. Blondelle, S. E. and Houghten R. A. (1996) *TIBTECH* 14 60–65.
9. Boons, G. J., Heskamp, B. and Hout, F. (1995) *Angew. Chem. Int. Ed. Engl.* 35 2845–2847.
10. Borman, S. (1996) *C&EN* 12 29–54.
11. Bosio, A., Binczek, E., Le Beau, M. M., Fernald, A. A. and Stoffel, W. (1996) *Genomics* 34 69–75.
12. Brockhausen, I., Matta, K. L., Orr, J. and Schachter, H. (1985) *Biochemistry* 24 1866–1874.
13. Brockhausen, I., Rachaman, E. S., Matta, K. L. and Schachter, H. (1983) *Carbohydr. Res.* 120 3–16.
14. Brockhausen, I., Hull, E., Hindsgaul, O., Schachter, H., Shah, R. N., Michnick, S. W., and Carver, J. P. (1989) *J. Biol. Chem.* 264 11211–11221.
15. Burbaum, J. J. and Sigal, N. H. (1997) *Curr. Opin. Chem. Biol.* 1 72–78.
16. Cadwell, R. C. and Joyce, G. F. (1994) in *Mutagenic PCR* cold spring harbor laboratory.
17. Cargill, J. F. and Lebl, M. (1997) *Curr. Opin. Chem. Biol.* 1 67–71.
18. Chabala, J. C. (1995) *Curr. Opin. Biotechnol.* 6 632–639.
19. Chang, M. L., Eddy, R. L., Shows, T. B. and Lau, J. T. (1995) *Glycobiology* 5 319–325.
20. Chatterjee, D. and Khoo, K.-H. (1998) *Glycobiology* 8 113–120.
21. Cheng, J., Sheldon, E. L., Wu, L., Uribe, A., Gerrue, L. O., Carrino, J., Heller M. J. and O'Connell, J. P. (1998) *Nat. Biotechnol.* 16 541–546.
22. Cole, S. T., Brosch, R., Parkhill, J., Garnier, T., Churcher, C., Harris, D., Gordon, S. V., Eiglmeier, K., Gas, S., Barry, C. E. 3rd, Tekaia, F., Badcock, K., Basham, D., Brown, D., Chillingworth, T., Connor, R., Davies, R., Devlin, K., Feltwell, T., Gentles, S., Hamlin, N., Holroyd, S., Hornsby, T., Jagels, K. and Barrell, B. G. (1998) *Nature* 393 537–44.
23. Datta, A. K., Sinha, A. and Paulson, J. C. (1998) *JBC* 273 9608–9614.
24. David, S., Auge, C. and Gautheron, C. (1991) *Adv. Carbohydr. Chem. Biochem.* 49 175–237.
25. Douglas, R. H., Ballou, C. E. (1982) *Biochemistry* 21 1561–1570.
26. Drews, J. (1996) *Drug Infor. J.* 30 97–108.
27. Drews, J. (1996) *Nat. Biotechnol.* 14 1516–1518.
28. Dryland, A. and Sheppard, R. C. (1986) *J. Chem. Soc., Perkin Trans.* 1 125–137.
29. Endo, T., Nishimura, R., Kawano, T., M, M. and Kobata, A. (1987) *Cancer Res.* 47 5242–5245.
30. Faber, L. P. (1991) in *Clinical Oncocology*, Holleb, A. I., (eds), American cancer society, pp.195–210.
31. Fodor, S. P. A., Read, J. L., Pirrung, M. C., Stryer, Lu, A. T. L. and Solas, D. (1991) *Science* 251 767–773.
32. Frank, R. and Doring, R. (1988) *Tetrahedron Lett.* 19 6031–6040.
33. Frechest, J. M. and Schuerch, C. (1971) *JACS* 93 492–494.
34. Frechest, J. M. and Schuerch, C. (1972) *C. J. Am. Chem. Soc.* 9 604–605.
35. Frechest, J. M. and Schuerch, C. (1972) *Carbohydr. Res.* 22 399–402.
36. Furukawa, K. and Roth, S. (1985) *Biochem. J.* 227 573–582.
37. Gaasterland, T. (1998) *Nat. Biotechnol.* 16 625–627.
38. Gillespie, W., Kelm, S. and Paulson, J., C. (1992) *J. Biol. Chem.* 267 21004–21010.
39. Granellin, C. R. (1992) in *Medicinal Chemistry for the 21st Centuary*, eds. Wwrmuth, C. G., Koga, N., Koning, H. and Metcalf, B. W. (Blackwell, London), pp. 3–12.

40. Gleeson, P. A. (1988) *Current topics in microbiology and immunology* 139 1–34.
41. Grout, D. H G. And Vic, G. (1998) *Curr. Opin. Chem. Biol.* 2 98–111.
42. Grundmann, U., Nerlich, C., Rein, T. and Zettlmeissl G. (1990) *Nucleic Acids Res.* 18 667.
43. Guthrie, R. D., Jenkins, A. D. and Stehilcek, J. (1971) *J. Chem. Soc. C* 2690–2691.
44. Hagen, F. K., Van Wuyckhuyse, B. and Tabak, L. A. (1993) *JBC* 268 18960–18965.
45. Hakomori, S. (1989) *Adv. Cancer Res.* 52 257–331.
46. Halcomb, R. L., Huang, H. and Wong, C.-H. (1994) *JACS* 116 11315–11322.
47. Hamamoto T., Kawasaki M., Kurosawa N., Nakaoka T., Lee Y. C., Tsuji S. (1993) *Bioorg. Med. Chem.* 1 141–145.
48. Harris, J. L. and Craik, C. S. (1998) *Current Opinion in Chemical Biology* 2 127–132.
49. Hassid, W. Z. and Doudoroff, M. (1950) *Adv. Carbohydr. Chem. Biochem.* 5 29–48.
50. Hendrickson, W. (1991) *Science* 25 51–58.
51. Herrmann, G. H., Ichikawa, Y., Wandrey, C., Gaeta, F. C. A., Paulson, J. C. and Wong, C.-H. (1993) *Tetrahedron lett.* 34 3091–3094.
52. Hidari, J. K., Ichikawa, S., Furukawa, K., Yamasaki, M. and Hirabayashi, Y. (1994) *Biochem. J.* 303 957–965.
53. Hitoshi, S., Kusunoki, S., Kanazawa, I. and Tsuji, S. (1995) *JBC* 270 8844–8850.
54. Hogan Jr., J. C. (1997) *Nat. Biotechnol.* 15 328–330.
55. Hoheisel, J. D. (1997) *TIBTECH* 15 465–469.
56. Hosomi, O., Takeya, A. and Kogure, T. (1984) *J. Biochem.* 95 1655–16.
57. Hsiau, L. T., Lee, W. C. and Wang, F. S. (1997) *Appl. Biochem. Biotechnol.* 62 303–315.
58. Nunez, H. A. and Barker, R. (1980) *Biochemistry* 19 485–489.
59. Ichikawa, Y., Look, G. C. and Wong, C.-H. (1992) *Anal. Biochem.* 202 215–238.
60. Ichikawa, Y. (1997) in *Glycopeptides and Related Compounds*, eds. Large, D. G. and Warren, C. D. PP. 79–205.
61. Ichikawa, Y., Look, G. C. and Wong, C.-H. (1992) *Anal. Biochem.* 202 215–238.
62. Ichikawa, S., Sakiyama, H., Suzuki, G., Hidari, K., I. and Hirabayashi, Y. (1996) *Proc. Natl. Acad. Sci. USA* 93 4638–4643.
63. Jacobs, J. W. and Fodor S. P. A. (1994) *TIBTECH* 12 19–26.
64. Janda, K. D. (1994) *Proc. Natl. Acad. Sci. USA* 91 10779–10785.
65. Joziasse, D. H., Shaper, J. H., Van den Eijnden, D. H., Van Tunen, A. J. and Shaper N. L. (1989) *JBC* 264 14290–14297.
66. Kahne, D. (1997) *Curr. Opin. Chem. Biol.* 1 130–135.
67. Kanie, O., Barresi, F., Ding, Y., Labbe, J., Otter A., Foesberg L. S., Ernst, B. and Hindsgaul, O. (1995) *Angew. Chem. Int. Ed. Engl.* 34 2720–2722.
68. Kaushal, G. P. and Elbein, A. D. (1986) *Arch. Biochem. Biophys.* 250 38–47.
69. Kaushal, G. P. and Elbein, A. D. (1987) *Biochemistry* 26 7953–7960.
70. Kawashima, H., Yamamoto, K., Osawa, T. and Irimura T. (1993) *JBC* 268 27118–27126.
71. Kenan, D. J., Tsai, D. E. and Keene, J. D. (1994) *TIBS* 19 57–64.
72. Kitagawa, H. and Paulson, J. C. (1993) *Biochem. Biophys. Res. Commun.* 194 375–382.
73. Kitagawa H., Tone Y., Tamura J., Neumann K. W., Ogawa T., Oka S., Kawasaki T., Sugahara K. (1998) *J. Biol. Chem.* 273 6615–6618
74. Kobata, A. (1998) *Glycoconjug. J.* 15 323–331.
75. Konishi, Y. and Misaki, A. (1976) *Abstr. Paper of Jap. Agric. Chem. Soc.*
76. Kornfeld, R. and Kornfeld, S. (1985) *Ann. Rev Biochem.* 54 631–664.
77. Kuchner, O. and Arnold, F., H. (1997) *TIBTECH* 15 523–530.
78. Kudo, T., Ikehara, Y., Togayachi, A., Kaneko, M., Hiraga, T., Sasaki, K. and Narimatsu H. (1998) *JBC* 273 26729–26738.
79. Kurosawa, N., Hamamoto, T., Inoue, M. and Tsuji S. (1995) *Biochim. Biophys. Acta* 1244 216–222.
80. Laine, R. A. (1994) *Glycobiology* 4 759–767.
81. Larsen, R. D., Ernst, L. K., Nair, R. P. and Lowe J. B. (1990) *Proc. Natl. Acad. Sci. USA* 87 6674–6678.
82. Larsen, R. D., Rajan, V. P., Ruff, M. M., Kukowska-Latallo, J., Cummings, R. D., Lowe, J. B. (1989) *Proc Natl Acad Sci USA* 86 8227–8231.
83. Leloir, L. F. (1971) *Science* 172 1299–1303.
84. Leong, P. and Schachter, H. (1995) *Eur. J. Biochem.* 231 317–328.
85. Liang, R., Loebach, J., Horan, N., Ge, M., Thompson, C., Yan, L. and Kahne, D. (1997) *Proc. Natl. Acad. Sci. USA* 94 10554–10559.
86. Liang, R., Yan, L., Loebach, J., Ge, M., Uozumi, Y., Sekanina, K., Horan, N., Gildersleeve, J., Thompson, C. Smith, A., Biswas, K., Still W. C. and Kahne, D. (1996) *Science* 274 1520–1522.
87. Lockney, M. W. and Sweely, C. S. (1982) *Biochim. Biophys. Acta* 712 234–241.
88. Mackenzie, P. I., Owens, I. S., Burchell, B., Bock, K. W., Bairoch, A., Belanger, A., Fournel-Gigleux, S., Green, M., Hum, D. W., lyanagi, T., Lancet, D., Louisot, P., Magdalou, J., Chowdhury, J. R., Ritter, J. K., Schachter, H., Tephly, T. R., Tipton, K. F. and Nebert, D. W. (1997) *Pharmacogenetics* 7 255–69.
89. Martensson, S., Due, C., Pahlsson, P., Nilsson, B., Eriksson, H., Zopf, D., Olsson, L. and Lundblad, A. (1988) *Cancer Res.* 48 2125–2131.
90. Masibay, A. S. and Qasba, P. K. (1989) *Proc. Natl. Acad. Sci. USA* 86 5733–5737.
91. Matulewich, M. C. and Cerezo, A. S. (1978) *Carbohydrate Pol.* 7 121–132.
92. Matuzaki, K., Sato, T., Enomoto, K., Yamamoto, I., Oshima, R., Hatanaka, K., Uryu, T., Kahu, H., Sone, Y. and Misaki, A. (1986) *Carbohydr. Res.* 157 171–183.
93. McDevitt, J. P. and Lansbury Jr, P. T. (1996) *JACS* 118 3818–3828.
94. Meldal, M., Auzanneau, F. I., Hindsgaul, O. and Palcic, M., M. (1994) *J. Chem. Soc. Commun.* 1849–1850.
95. Mendicino, J., Sivakami, S., Davila, M. and Chandrasekaran, E. V. (1982) *JBC* 257 3987–3994.
96. Mengling, B. J. and Turco S. J. (1998) *Current opinion in structural biology* 8 572–577.
97. Merrifield, R. B. J. (1963) *JACS* 85 2149–2154.
98. Meurer, J. A., Naylor, J. M., Baker, C. A., Thomsen, D. R., Homa, F. L. and Elhammer, A. P. (1995) *J. Biochem.* 118568–574.
99. Michels, P. C., Khmelnitsky, Y. L., Dordick, J. S. ans Clark, D. S. (1998) *TIBTECH* 16 210–215.
100. Minamida, S., Aoki, K., Natsuka, S., Omichi, K., Fukase, K., Kusumoto, S. and Hase S. (1996) *J. Biochem.* 120 1002–1006.
101. Minowa, M. T., Oguri, S., Yoshida, A., Hara, T., Iwamatsu, A., Ikenaga and H., Takeuchi, M. (1998) *JBC* 273 11556–11562.
102. Misaki, A., Kakuta, M., Sasaki, T. and Miyaji, H. (1980) *Carbohydr. Res.* 92 115–129.

103. Misaki, A., Johnson, J., Kirkwood, S., Scaletti, J. V. ans Smith F. (1968) *Carbohydr. Res.* 6 150–164.
104. Mizuochi, T., Nishimura, R., Derappe, C., Taniguchi, T., Hamamoto, T., Mochizuki, M. and Kobata, A. (1983) *JBC* 258 14126–14129.
105. Moore, J. C. and Arnold, F. H. (1996) *Nat. Biotechnol.* 14 458–467.
106. Nagata Y, Yamashiro S, Yodoi J, Lloyd K O, Shiku H, Furukawa K (1992) *JBC* 267 12082–12089.
107. Nara K., Watanabe Y., Maruyama K., Kasahara K., Nagaiy Y., Sanai Y. (1994) *Proc. Natl. Acad. Sci. U.S.A.* 91 7952–7956
108. Nicholls, A., Sharp, K. and Honig, B. (1991) *Proteins Struct. Funct. Genet.* 11 281–296.
109. Nicolaou, K. C., Florke, H., Egan, M. G., Barth, T. and Estevez, V. A. (1995) *Tetrahedron Lett.* 36 1775–1778.
110. Nigou, J., Gilleron, M., Cahuzac, B., Bounery, J.-D., Herold, M., Thurnher, M. and Puzo, G. (1997) *JBC* 272 23094–23103.
111. Nilsson, K. G. L. (1988) *TIBTECH* 6 256–264.
112. Nilsson, K. G. L. (1996) in *Modern Methods in Carbohydrate Synthesis*, eds. Khan, S. H. and O'Neill R. A. p. 518–546.
113. Nishikar A., Ihara Y., Hatakeyama M., Kangawa K., Taniguchi N. (1992) *JBC* 267 18199–18204.
114. Nishino, T., Yokoyama, G., Dobashi, K., Fujihara, M. and Nagumo, T. (1989) *Carbohydr. Res.* 186 119–129.
115. Omichi, K., Aoki, K., Minamida, S. and Hase, S. (1997) *Eur. J. Biochem.* 245 143–146.
116. Orlean, P., Albright, C. and Robbins, P., W. (1988) *JBC* 263 17499–17507
117. Orntoft, T. F. and Bech, E. (1995) *Glycoconjug. J.* 12 200–205.
118. Oths, P. J., Hayer, R. M. and Floss, H. G. (1990) *Carbohydr. Res.* 198 91–99.
119. Palcic, M. M. (1994) *Methods in enzymology* 230 300–316.
120. Palcic, M. M., Heerze, L. D., Pierce, M. and Hinsgaul, O. (1988) *Glycocon. J.* 5 49–63.
121. Palcic, M., Venot, A. P., Ratcliffe, R. M. and Hinsgaul, O. (1989) *Carbohydr. Res.* 190 1–11.
122. Pease, A., Solas, D., Sullivan, E J., Cornin, M. T., Holmes, C. P. and Fodor, S. P. A. (1994) *Proc. Natl. Acad. Sci. USA* 91 5022–5026.
123. Prieto, P. A., Mukerji, P., Kelder, B., Erney, R., Gonzales, D., Yun, J. S., Smith, D. F., Moremen, K. W., Nardelli, C., Pierce, M., Li, Y., Chen, X., Wagner, T. E, Cummings, R. D. and Kopchick, J. J. (1995) *JBC* 270 295115–29519.
124. Rademann, J. and Schmidt, R. R. (1996) *Tetrahedron Lett.* 37 3989–3990.
125. Ramsay, G. (1998) *Nat. Biotechnol.* 16 40–44.
126. Rees, D. A. (1965) *Ann. Rep. Chem. Soc.* (London) 469–477.
127. Robinson, J. A., Robinson, H. C. (1985) *Biochem. J.* 227 805–814
128. Rodebaugh, R., Joshi, S., Fraser-Reid, B. and Geysen, H. M. (1997) *J. Org. Chem.* 62 5660–5661.
129. Romero, P. A., Lussier, M., Sdicu, A. M., Bussey, H. and Herscovics, A. (1997) *Biochem. J.* 321 289–295.
130. Ronin, C. (1998) *Clin. Chem. Lab. Med.* 36 373–378.
131. Saito, H., Gu, J., Nishikawa, A., Ihara, Y., Fujii, J., Kohgo, Y. and Taniguchi, N. (1995) *Eur. J. Biochem.* 233 18–26.
132. Sanson, C. (1997) *Nat. Biotechnol.* 15 1253–1256.
133. Sasaki, T., Abiki, N., Nitta, K., Takatsuka, N. and Sugino, Y (1978) CancerRes. 38 379–383.
134. Schachter, H., Brockhausen, I. and Hull, E. (1989) *Methods Enzymol.* 179 351–397.
135. Schachter, H. (1994) in *Molecular Glycobiology*, Fukuda, M. and Hindsagul, O. (eds) Oxford University Press, NY pp. 88–149.
136. Schaeper, R. J., Das, K. K., Zhixiong, L. and Basu, S. (1992) *Carbohydr. Res.* 236 227–244.
137. Schawrtz, N. (1976) *JBC* 251 285–291.
138. Schenkman, S., Jiang, M.-S., Hart, G. W. and Nussenzweing, A. (1991) *Cell* 65 1117–1125.
139. Schullek, J. R., Butler, J. H., Ni, Z.-J., Chen, D. and Yuan, Z. (1997) *Ana. Biochem.* 246 20–29.
140. Schulte, S. and Stoffel W. (1993) *Proc. Natl. Acad. Sci. USA* 90 10265–10269.
141. Schuster, M., Wang P., Paulson C. and Wong C., H. (1994) *JACS* 116 1135.
142. Schwartz, N. B. and Rodn, L. (1975) *JBC* 250 5200–5207.
143. Seitz, O. and Wong, C.-H. (1997) *JACS* 119 8766–8776.
144. Shah, K., Liu, Y., Deirmengian, C. and Shkat, K. M. (1997) *Proc. Natl. Acad. Sci. U.S.A.* 94 3565–3570.
145. Shoreibah, M., Perng, G. S., Adler, B., Weinstein, J., Basu, R., Cupples, R., Wen, D., Browne, J. K., Buckhaults, P. and Fregien, N. (1993) *JBC* 268 15381–15385.
146. Simon, P. M. (1996) *Drug Discovery Today* 1 552–528.
147. Sittampalam, G. S., Kahl, S. D. and Janzen, W. P. (1997) *Curr. Opin. Chem. Biol.* 1 384–391.
148. Smith, T. K., Cottaz, S., Brimacombe, J. S. and Ferguson (1996) *JBC* 271 6476.
149. Sosnowski, R. G., Tu, G., Butler, W. F., and Heller, M. J. (1997) *Proc. Natl. Acad. Sci. USA* 94 1119–1123.
150. Spaller, M. R., Burger, M. T., Fardis, M. and Bartlett, P. A. (1997) *Curr. Opin. Chem. Biol.* 1 47–53.
151. Stinson, S. C. (1998) *C&EN* 16 42–46.
152. Strahan, K. M., Gu, F., Preece, A. F., Gustavsson, I., Andersson, L. and Gustafsson K. (1995) *Immunogenetics* 41 101–105.
153. Stults, C. L. M. and Macher, B. A., (1990) *Arch. Biochem. Biophys.* 280 20–26.
154. Tan, J., D'Agostaro, A. F., Bendiak, B., Reck, F., Sarkar, M., Squire, J. A., Leong, P. and Schachter, H. (1995) *Eur. J. Biochem.* 231 317–328.
155. Toki D., Sarkar M., Yip B., Reck F., Joziasse D., Fukuda M., Schachter H., Brockhausen I. (1997) *Biochem. J.* 325 63–69
156. Toone, E. J., Simon, M. D., Bednarski, G. M. and Whitesides, G. M. (1989) *Tetrahedron* 45 5365–5422.
157. Unverzagt, C. (1996) *Anew Chem Int Ed.* 35 2350–2352.
158. Uozumi, N., Yanagidani, S., Miyoshi, E., Ihara, Y., Sakuma, T., Gao, C. X., Teshima, T., Fujii, S., Shiba, T. and Taniguchi, N. (1996) *JBC* 271 27810–27817.
159. Van den Eijnden, D. H., Koenderman, A. H. L. and Schiphorst, W. E. C. M. (1988) *JBC* 263 12461–12471.
160. Voynow, J. A., Kaiser, R. S., Scanlin, T. F. and Glick, M., C. (1991) *JBC* 266 21572–21577.
161. Watt, G. M., Lowdsen, P. A. S. and Filtsch, S. L. (1997) *Curr. Opin. Struc. Biol.* 1 652–660.
162. Wen, D. X., Livingston, B. D., Medzihradszky, K. F., Kelm, S., Burlingame, A. L. and Paulson, J. C. (1992) *JBC* 267 21011–21019.
163. Witczak, Z. J. and Nieforth, K. A. (1997) in: *Carbohydrates in drug design* (eds.) Marcel Dekker, N.Y.
164. Wong, C.-H. (1996) in *Modern Methods in Carbohydrate Synthesis*, eds. Khan, S. H. and O'Neill R. A. pp. 467–491.

165. Wong, C. H., Ye, X. S. and Zhang, Z. (1998) *JACS* 120 7137–7138
166. Yamamoto, F., Marken, J., Tsuji, T., White, T., Clausen, H. and Hakomori, S. (1990) *JBC* 265 1146–1151.
167. Yan, L. Y., Smith, D. F. and Cummings, R. D., (1994) *Anal. Biochem.* 223 111–118.
168. Yanagidani, S., Uozumi, N., Ihara, Y., Miyoshi, E., Yamaguchi, N. and Taniguchi N. (1997) *J. Biochem.* 121 626–632.
169. Yip, C. L., Welch, S. K., Klebl, F., Gilbert, T., Seide, I. P., Grant, F. J., Ohara, P. J. and MacKay, V. L. (1994) *Proc. Natl. Acad. Sci. USA* 91 2723–2727.
170. Zehavi, U. and Herchman, M. (1984) *Carbohydr. Res.* 128 160.
171. Zehavi, U., Sadeh, S. and Herchman, M. (1983) *Carbohydr. Res.* 124 23.
172. Zeng, Y., Bannon, G., Thomas, V. H., Rice, K., Drake, R. and Elbein, A. (1997) *JBC* 272 31340–31347.
173. Zhang, J. H., Dawes, G. and Stemmer, W. P. C. (1997)) *Proc. Natl. Acad. Sci. U.S.A.* 94 4504–4509.

What is claimed is:

1. A method of identifying a carbohydrate capable of binding an entity, the method comprising the steps of:
   (a) enzymatically synthesizing an addressable carbohydrate library including a plurality of carbohydrate structures each being attached at a specific and addressable location of an array, wherein each of said plurality of carbohydrate structures is composed of naturally occurring monosaccharides, such that a stereo-specificity of each bond interconnecting said monosaccharide units of said plurality of carbohydrate structures is defined by said addressable location thereof on said array and wherein each of said plurality of carbohydrate structures is composed of at least 2 and no more than 20 monosaccharide units each being naturally occurring; wherein each of said plurality of carbohydrate structures is attached to said array via a linker, said linker including at least one ethylenglycol derivative, at least two cyanuric chloride derivatives and an anilino group and
   (b) screening said addressable carbohydrate library with the entity thereby identifying the carbohydrate capable of binding the entity.

2. The method of claim 1, wherein said addressable location of said carbohydrate also defines a stereo-specificity thereof.

3. The method of claim 1, wherein said entity is selected from the group consisting of a polypeptide encoded by a polynucleotide and a protein extracted from a natural source.

4. A method of identifying a carbohydrate capable of binding an entity, the method comprising the steps of:
   (a) enzymatically synthesizing an addressable carbohydrate library including a plurality of carbohydrate structures each being attached at a specific and addressable location of an array, wherein each of said plurality of carbohydrate structures is composed of at least 2 and no more than 20 monosaccharide units each being naturally occurring and whereas each of said plurality of carbohydrate structures is attached to said array via a linker, said linker including at least one ethylenglycol derivative, at least two cyanuric chloride derivatives and an anilino group; and
   (b) screening said addressable carbohydrate library with the entity thereby identifying the carbohydrate capable of binding the entity.

5. The method of claim 4, wherein said linker includes three ethylenglycol derivatives, four cyanuric chloride derivatives and an anilino group.

6. The method of claim 4, wherein at least one carbohydrate structure of said plurality of carbohydrate structures is a branched carbohydrate having a single structure defined by said addressable location thereof on said array.

7. The method of claim 4, wherein said addressable location of each of said carbohydrate structures defines a stereo-specificity thereof.

8. The method of claim 4, wherein said entity is selected from the group consisting of a polypeptide encoded by a polynucleotide and a protein extracted from a natural source.

9. A method of identifying a carbohydrate capable of binding an entity, the method comprising the steps of:
   (a) enzymatically synthesizing an addressable carbohydrate library including a plurality of carbohydrate structures each being attached at a specific and addressable location of an array, wherein each of said plurality of carbohydrate structures is composed of at least 2 and no more than 20 monosaccharide units each being naturally occurring and whereas a stereo-specificity of all carbohydrate structures in given addressable locations on said array is identical; and
   (b) screening said addressable carbohydrate library with the entity thereby identifying the carbohydrate capable of binding the entity; and
   wherein each of said plurality of carbohydrate structures is attached to said array via a linker, said linker including at least one ethylenglycol derivative, at least two cyanuric chloride derivatives and an anilino group.

10. The method of claim 9, wherein at least one carbohydrate structure of said plurality of carbohydrate structures is a branched carbohydrate having a single structure defined by said addressable location thereof on said array.

11. The method of claim 9, wherein said entity is selected from the group consisting of a polypeptide encoded by a polynucleotide and a protein extracted from a natural source.

12. The method of claim 1, wherein said monosaccharide units are each independently selected from the group consisting of D-Glucose, D-Galactose, D-Mannose, L-Fucose, D-Xylose, D-N-Acetylglucoseamine, D-N-Acetylgalactoseamine, D-Glucuronic acid, D-Galacturonic acid, L-Rhamnose, L-Arabinose, D-Fructose, D-Apiose, (3-C-(Hydroxymethyl)-D-glycero-tetrose), L-Aceric acid (3-C-Carboxy-5dexoyl-xylose) Sialic Acid, and 2-sulfo-D-Mannose, 4-sulfo-L-Fucose, 2,6di-sulfo-D-Mannose and 6-sulfa-D-Mannose.

13. The method of claim 4, wherein said monosaccharide units are each independently selected from the group consisting of D-Glucose, D-Galactose, D-Mannose, L-Fucose, D-Xylose, D-N-Acetylglucoseamine, D-N-Acetylgalactoseamine, D-Glucuronic acid, D-Galacturonic acid, L-Rhamnose, L-Arabinose, D-Fructose, D-Apiose, (3-C-(Hydroxymethyl)-D-glycero-tetrose), L-Aceric acid (3-C-Carboxy-5dexoyl-xylose) Sialic Acid, and 2-sulfo-D-Mannose, 4-sulfo-L-Fucose, 2,6di-sulfo-D-Mannose and 6-sulfo-D-Mannose.

14. The method of claim 9, wherein said monosaccharide units are each independently selected from the group consisting of D-Glucose, D-Galactose, D-Mannose, L-Fucose, D-Xylose, D-N-Acetylglucoseamine, D-N-Acetylgalactoseamine, D-Glucuronic acid, D-Galacturonic acid, L-Rhamnose, L-Arabinose, D-Fructose, D-Apiose, (3-C-(Hydroxymethyl)-D-glycero-tetrose), L-Aceric acid (3-C-Carboxy-5dexoyl-xylose) Sialic Acid, and 2-sulfo-D-Mannose, 4-sulfo-L-Fucose, 2,6di-sulfo-D-Mannose and 6-sulfo-D-Mannose.

15. The method of claim 1, wherein said monosaccharide units are in alpha or beta configurations.

16. The method of claim 4, wherein said monosaccharide units are in alpha or beta configurations.

17. The method of claim 9, wherein said monosaccharide units are in alpha or beta configurations.

18. The method of claim 1, wherein said monosaccharide units are sulfated.

19. The method of claim 4, wherein said monosaccharide units are sulfated.

20. The method of claim 9, wherein said monosaccharide units are sulfated.

* * * * *